US006924300B2

(12) United States Patent
Momose et al.

(10) Patent No.: US 6,924,300 B2
(45) Date of Patent: Aug. 2, 2005

(54) OXYIMINOALKANOIC ACID DERIVATIVES

(75) Inventors: Yu Momose, Takarazuka (JP); Hiroyuki Odaka, Kobe (JP); Hiroshi Imoto, Kusatsu (JP); Hiroyuki Kimura, Sakai (JP); Junichi Sakamoto, Toyonaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/331,056

(22) Filed: Dec. 27, 2002

(65) Prior Publication Data

US 2003/0186985 A1 Oct. 2, 2003

Related U.S. Application Data

(62) Division of application No. 09/714,699, filed on Nov. 16, 2000, now Pat. No. 6,495,581, which is a division of application No. 09/423,854, filed as application No. PCT/JP99/02407 on May 10, 1999, now Pat. No. 6,251,926.

(30) Foreign Application Priority Data

May 11, 1998 (JP) ............................................ 10-127921
May 11, 1998 (JP) ............................................ 10-127922

(51) Int. Cl.$^7$ .................... A61K 31/426; A61K 31/421; C07D 277/20; C07D 271/06; C07D 263/30
(52) U.S. Cl. ...................... 514/365; 548/131; 548/194; 548/200; 548/204; 548/233; 548/236; 514/370; 514/374
(58) Field of Search ................................ 514/364, 365, 514/374, 370; 548/131, 204, 236, 194, 233

(56) References Cited

U.S. PATENT DOCUMENTS

| | | | |
|---|---|---|---|
| 5,563,168 A | 10/1996 | Brand | |
| 5,750,532 A | 5/1998 | Girijavallabhan | |
| 5,902,726 A | 5/1999 | Kliewer et al. | |
| 6,251,926 B1 * | 6/2001 | Momose et al. | 514/364 |
| 6,495,581 B1 * | 12/2002 | Momose et al. | 514/365 |

FOREIGN PATENT DOCUMENTS

| EP | 0 075 805 | 4/1983 |
|---|---|---|
| EP | 0 075 805 A | 4/1983 |
| EP | 0 233 780 A | 8/1987 |
| EP | 0 233 780 | 8/1987 |
| EP | 0 370 629 A | 5/1990 |
| EP | 0 370 629 | 5/1990 |
| EP | 0 400 805 A | 12/1990 |
| EP | 0 400 805 | 12/1990 |
| EP | 0 506 149 | 9/1992 |
| EP | 0 506 149 A | 9/1992 |
| EP | 0 581 187 A | 2/1994 |
| EP | 0 708 098 | 4/1996 |
| EP | 0 708 098 A | 4/1996 |
| EP | 0 916 651 | 5/1999 |
| EP | 0 916 651 A | 5/1999 |

(Continued)

OTHER PUBLICATIONS

B. Forman et al., "15–Deoxy–$\Delta^{12,14}$–Prostaglandin $J_2$ ... " *Cell*, vol. 83, pp. 803–812 (Dec. 1, 1995).
J. Lehmann et al., "An Antidiabetic Thiazolidinedione Is a High ... " *J. Biol. Chem.*, vol. 270, 12953–12956 (Jun. 2, 1995).
T. Willson et al., "The Structure–Activity Relationship between ... " *J. Med. Chem.*, vol. 39, pp. 665–668 (1996).
P. Tontonoz et al., "Terminal Differentiation of human liposarcom cells ... " *Proc. Natl. Acad. Sci. USA*, vol. 94, pp. 237–241 (Jan., 1997).
J. Lehmann et al., "Peroxisome Proliferator–activated Receptors ... " *J. Biol. Chem.*, vol. 272, No. 6, pp. 3406–3410 (Feb. 7, 1997).

(Continued)

*Primary Examiner*—Golam M M Shameem
(74) *Attorney, Agent, or Firm*—Elaine M. Ramesh; Mark Chao

(57) ABSTRACT

To provide a novel oxyiminoalkanoic acid derivative which has excellent hypoglycemic and hypolipidemic actions and which is used for the prevention or treatment of diabetes mellitus, hyperlipemia, insulin insensitivity, insulin resistance and impaired glucose tolerance.

A compound represented by the formula:

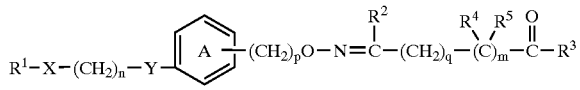

wherein $R^1$ is an optionally substituted hydrocarbon group or an optionally substituted heterocyclic group; X is a bond, —CO—, —CH(OH)— or a group represented by —NR$^6$— wherein R$^6$ is a hydrogen atom or an optionally substituted alkyl group; n is an integer of 1 to 3; Y is an oxygen atom, a sulfur atom, —SO—, —SO$_2$— or a group represented by —NR$^7$— wherein R$^7$ is a hydrogen atom or an optionally alkyl group; ring A is a benzene ring optionally having additional one to three substituents; p is an integer of 1 to 8; $R^2$ is a hydrogen atom, an optionally substituted hydrocarbon group or an optionally substituted heterocyclic group; q is an integer of 0 to 6; m is 0 or 1; $R^3$ is a hydroxy group, OR$^8$ (R$^8$ is an optionally substituted hydrocarbon group.) or NR$^9$R$^{10}$ (R$^9$ and R$^{10}$ are the same or different groups which are selected from a hydrogen atom, an optionally substituted hydrocarbon group, an optionally substituted heterocyclic group or an optionally substituted acyl group or R$^9$ and R$^{10}$ combine together to form a ring); R$^4$ and R$^5$ are the same or different groups which are selected from a hydrogen atom or an optionally substituted hydrocarbon group wherein R$^4$ may form a ring with R$^2$; provided that when R$^1$ is a ethoxymethyl, a $C_{1-3}$ alkyl, phenyl or p-methoxyphenyl and q=m=0, R$^3$ is NR$^9$R$^{10}$; and provided that O-[2-chloro-4-(2-quinolylmethoxy)phenylmethyl]oxime and a methyl pyruvate of [2-chloro-4-(2-quinolylmethoxy)phenylmethyl]-2-iminoxypropionic acid are excluded; or a salt thereof.

19 Claims, No Drawings

FOREIGN PATENT DOCUMENTS

| | | |
|---|---|---|
| GB | 1582029 | 12/1980 |
| JP | 59-167576 | 3/1983 |
| JP | 59-167576 | 9/1984 |
| JP | 62-77391 | 12/1984 |
| JP | 9-323929 | 4/1996 |
| JP | 9-323929 | 12/1997 |
| JP | 62-2077391 | 4/1998 |
| JP | 11-193272 | 7/1999 |
| WO | WO 96 02507 A | 2/1996 |
| WO | WO 96/11183 | 4/1996 |
| WO | WO 96/33724 | 10/1996 |
| WO | WO 96 38427 A | 12/1996 |
| WO | WO 96/40128 | 12/1996 |
| WO | WO 97 25042 A | 7/1997 |
| WO | WO 97/25042 | 7/1997 |
| WO | WO 97 31907 A | 9/1997 |
| WO | WO 98/05331 | 2/1998 |
| WO | WO 99/04815 | 2/1999 |

OTHER PUBLICATIONS

M. Ricote et al., "The peroxisome proliferator–activated . . . " *Nature*, vol. 391, pp. 79–82 (Jan. 1, 1998).

C. Jiang et al., "PPAR–γ agonists inyhibit production . . . " *Nature*, vol. 391, pp. 82–86 (Jan. 1, 1998).

Jiang, et al. "PPAR–γ agonists inhibit production of monocyte inflammatory cytokines" *Nature 391:82–6* (Jan. 1998).

Ricote, et al. "The peroxisome proliferator–activated receptorγ is a negative regulator of macrophage activation" *Nature* 391: 79–82 (Jan. 1998).

Lehmann, et al. "Peroxisome Proliferator–activated Receptors α and γAre Activated by Indomethacin and Other Non–steroidal Anti–inflammatory Drugs" *The Journal of Biological Chemistry* 272(6) 3406–10 (Feb. 7, 1997).

Tontonoz, et al. "Terminal differentiation of human liposarcoma cells induced by ligands for peroxisome proliferator–activated receptor γ and the retinoid X receptor" *The National Academy of Sciences of the USA* 94: 237–241 (Jan. 1997).

Willson, et al. "The Structure–Activity Relationship between Peroxisome Proliferator–Activated Receptor γ Agonism and the Antihyperglycemic Activity of Thiazolidinediones" *Journal of Medicinal Chemistry* 39(3): 665–68 ((1996).

Lehmann, et al. "An Antidiabetic Thiazolidinedione Is a High Affinity Ligand for Peroxisome Proliferator–activated Receptor γ (PPAR γ)" *The Journal of Biological Chemistry* 270(22): 12953–56 (Jun. 2, 1995).

Forman, et al. "15–Deoxy–$\Delta^{12,-14}$–Prostaglandin $J_2$ Is a Ligand for the Adipocyte Determination Factor PPARγ" *Cell* 83: 803–12 (Dec. 1, 1995).

* cited by examiner

OXYIMINOALKANOIC ACID DERIVATIVES

This application is a divisional of Ser. No. 09/714,699 filed Nov. 16, 2000, now U.S. Pat. No. 6,495,581 which is divisional of Ser. No. 09/423,854, filed on Nov. 15, 1999, now U.S. Pat. No. 6,251,926, which is a 371 of PCT/JP99/02407, filed May 10, 1999.

TECHNICAL FIELD

The present invention relates to novel oxyiminoalkanoic acid derivatives having hypoglycemic effect and hypolipidemic effect, a novel pharmaceutical composition and a retinoid-related receptor function adjuster comprising an oxyiminoalkanoic acid. Such novel oxyiminoalkanoic acid derivatives, pharmaceutical compositions and retinoid-related receptor function adjusters are useful as agents for prevention and/or treatment of diabetes mellitus, hyperlipemia, impaired glucose tolerance, inflammatory disease, arteriosclerosis and the like.

BACKGROUND ART

Examples of known oxyiminoalkanoic acid derivatives are the intermediates used in the production of β-lactam compounds (Japanese Patent Application KOKAI No.49382/1983, 167576/1984, 77391/1987, 192387/1987, 47186/1991) and a compound having a leukotriene biosynthesis inhibiting effect (e.g., WO96/02507).

However, these compounds have not been reported to have hypoglycemic, hypolipidemic effects and retinoid-related receptor function adjuster activity yet.

On the other hand, oxime derivatives were reported as a prophylactic and/or therapeutic agent against hyperlipemia and hyperglycemia (e.g., Japanese Patent Application KOKAI No.48779/1997, 323929/1997), but these derivatives are not an oxyiminoalkanoic acid derivative.

Moreover, while a phenylalkanoyl acid derivative having a substituted hydroxyl group on its 4-position is reported (e.g. in WO97/31907, WO97/25042) as a peroxisome proliferator-activated receptor gamma (abbreviated occasionally as PPARγ in this specification) agonist which is one of retinoid-related receptor function adjusters, this derivative is not an oxyiminoalkanoic acid derivative.

The peroxisome proliferator-activated receptor gamma (PPARγ) is a member of an intranuclear hormone receptor superfamily, representatives of which are a steroid hormone receptor and a thyroidal hormone receptor, and induced to be expressed at a very early stage of the fat cell differentiation, and plays an important role as a master regulator in the fat cell differentiation. PPARγ is bound to a function adjuster to form a dimer with a retinoid X receptor (RXR), and is also bound to the responding site of a target gene in a nucleus, whereby regulating (activating) the transcription efficiency directly. Recently, a metabolite of prostaglandin $D_2$, namely, 15-deoxy-$\Delta^{12,14}$prostaglandin $J_2$, was proved to be an endogenous agonist of PPARγ, and some insulin sensitivity enhancing agent, such as a thiazolidinedione derivative, was proved to have a PPARγ agonistic activity, with its potency being in parallel with its blood sugar reducing effect and fat cell differentiation promoting effect [Cell, Vol. 83, page 803 (1995); The Journal of Biological Chemistry, Vol. 270, page 12953 (1995); Journal of Medicinal Chemistry, Vol. 39, page 655 (1996)]. More recently, it has been shown that: 1) PPARγ is expressed in a cultured, human fat sarcoma-derived cell, and its growth is terminated by addition of PPARγ agonist [Proceedings of the National Academy of Science of The United States of America, Vol. 94, page 237 (1997)], 2) a non-steroid antiinflammatory agent such as indomethacin and phenoprofen has a PPARγ agonistic activity [The Journal of Biological Chemistry, Vol. 272, page 3406 (1997)], 3) PPARγ is highly expressed in an activated macrophage, and the addition of its agonist serves to inhibit the transcription of a gene concerned in an inflammation [Nature, Vol. 391, p.79 (1998)], and 4) a PPARγ agonist inhibits the production of inflammatory cytokines (TNF α, IL-1 β, IL-6) by a monocyte [Nature, Vol. 391, page 82 (1998)].

DISCLOSURE OF THE INVENTION

The object of the present invention is to provide a novel oxyiminoalkanoic acid derivative and retinoid-related receptor function adjuster which has excellent hypoglycemic effect and hypolipidemic effect and which is useful as an agent for prevention and/or treatment of diabetes mellitus, hyperlipemia, impaired glucose tolerance, inflammatory disease and arteriosclerosis.

The present invention relates to:

1) a compound represented by Formula (I-1):

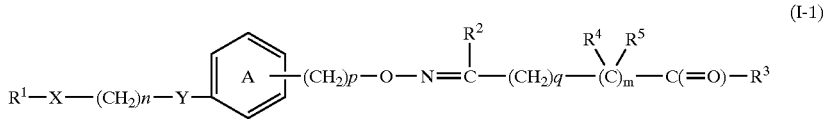

(I-1)

wherein $R^1$ is an optionally substituted hydrocarbon group or an optionally substituted heterocyclic group; X is a bond, —CO—, —CH(OH)— or a group represented by —$NR^6$— wherein $R^6$ is a hydrogen atom or an optionally substituted alkyl group; n is an integer of 1 to 3; Y is an oxygen atom, a sulfur atom, —SO—, —$SO_2$— or a group represented by —$NR^7$— wherein $R^7$ is a hydrogen atom or an optionally substituted alkyl group; ring A is a benzene ring optionally having an additional one to three substituents; p is an integer of 1 to 8; $R^2$ is a hydrogen atom, an optionally substituted hydrocarbon group or an optionally substituted heterocyclic group; q is an integer of 0 to 6; m is 0 or 1; $R^3$ is a hydroxy group, $OR^8$ ($R^8$ is an optionally substituted hydrocarbon group) or $NR^9R^{10}$ ($R^9$ and $R^{10}$ are the same or different groups which are selected from a hydrogen atom, an optionally substituted hydrocarbon group, an optionally substituted heterocyclic group or an optionally substituted acyl group or $R^9$ and $R^{10}$ combine together to form a ring); $R^4$ and $R^5$ are the same or different groups which are selected from a hydrogen atom or an optionally substituted hydrocarbon group wherein $R^4$ may form a ring with $R^2$; provided that when $R^1$ is a ethoxymethyl, a $C_{1-3}$ alkyl, phenyl or p-methoxyphenyl and q=m=0, $R^3$ is $NR^9R^{10}$; and provided that O-[2-chloro-4-(2-quinolylmethoxy)phenylmethyl] oxime of methyl pyruvate and [2-chloro-4-(2-quinolylmethoxy)phenylmethyl]-2-iminoxypropionic acid are excluded; or a salt thereof;

2) A compound of the above 1) wherein $R^1$ is an optionally substituted heterocyclic group or an optionally substituted cyclic hydrocarbon group;

3) A compound of the above 1) wherein X is a bond or a group represented by —NR$^6$— wherein R$^6$ is an optionally substituted alkyl group;
4) A compound of the above 1) wherein n is 1 or 2;
5) A compound of the above 1) wherein Y is an oxygen atom;
6) A compound of the above 1) wherein p is an integer of 1 to 3;
7) A compound of the above 1) wherein R$^3$ is a hydroxy group or —OR$^8$ or —NR$^{9'}$R$^{10'}$, wherein R$^8$ is an optionally substituted hydrocarbon group and R$^{9'}$ and R$^{10'}$ are the same or different groups which are selected from a hydrogen atom, an optionally substituted hydrocarbon group, or R$^{9'}$ and R$^{10'}$ combine together to form a ring;
8) A compound of the above 1) wherein q is an integer of 0 to 4;
9) A compound of the above 1) wherein R$^2$ is an optionally substituted hydrocarbon group;
10) A compound of E-4-[4-(5-methyl-2-phenyl-4-oxazolylmethoxy)benzyloxyimino]-4-phenylbutyric acid or its salt;
11) A compound which is selected from a group of E-4-[4-(5-methyl-2-phenyl-4-oxazolylmethoxy) benzyloxyimino]-4-phenylbutyramide and E-8-[4-(5-methyl-2-phenyl-4-oxazolylmethoxy)benzyloxyimino)-8-phenyloctanoic acid;
12) A compound of the above 2) wherein a ring of an optionally substituted heterocyclic group or an optionally substituted cyclic hydrocarbon group of R$^1$ is selected from the group represented by formulae of

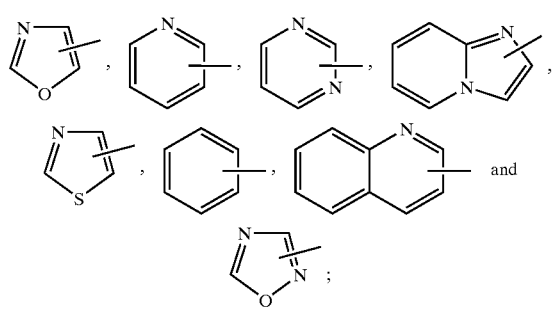

13) A compound of the above 12) wherein the ring optionally has one or two substituents which is selected from the group of an optionally substituted phenyl, an optionally substituted furyl, an optionally substituted thienyl and an optionally substituted C$_{1-4}$ alkyl;

14) A compound of the above 12) wherein the ring is

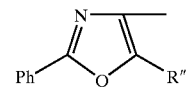

wherein Ph is an optionally substituted phenyl group, and R″ is a hydrogen or an optionally substituted C$_{1-6}$ alkyl group;

15) A compound represented by Formula (I-2) of

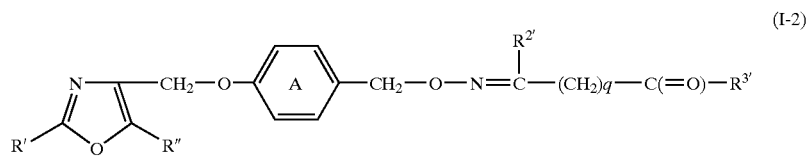

wherein R' is an optionally substituted phenyl, furyl or thienyl group; R″ is a hydrogen or a C$_{1-6}$ alkyl which is optionally substituted by at least one selected from a group of a C$_{1-6}$ alkoxy and a halogen; R$^{2'}$ is a phenyl which is optionally substituted by at least one selected from a group of a hydrogen, an alkyl, an alkoxy and a halogen; q is an integer of 1 to 6; and R$^{3'}$ is a hydroxy, a C$_{1-6}$ alkoxy or —NR$^9$R$^{10}$ in which R$^9$ and R$^{10}$ are independently selected from the group of a hydrogen atom, an optionally substituted hydrocarbon group, an optionally substituted heterocyclic group or an optionally substituted acyl group, or R$^9$ and R$^{10}$ combine together to form a ring; a ring A is a benzene ring optionally having additional one to three substituents; or a salt thereof;

16) A pharmaceutical composition comprising a compound represented by Formula (II)

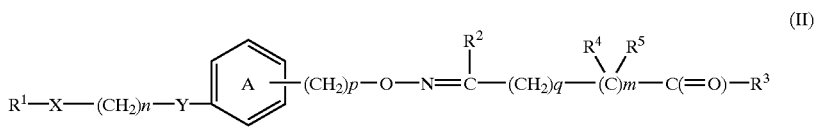

wherein R$^1$ is an optionally substituted hydrocarbon group or an optionally substituted heterocyclic group; X is a bond, —CO—, —CH(OH)— or a group represented by —NR$^6$— wherein R$^6$ is a hydrogen atom or an optionally substituted alkyl group; n is an integer of 1 to 3; Y is an oxygen atom, a sulfur atom, —SO—, —SO$_2$— or a group represented by —NR$^7$— wherein R$^7$ is a hydrogen atom or an optionally substituted alkyl group; ring A is a benzene ring optionally having additional one to three substituents; p is an integer of 1 to 8; R$^2$ is a hydrogen atom, an optionally substituted hydrocarbon group or an optionally substituted heterocyclic group; q is an integer of 0 to 6; m is 0 or 1; R$^3$ is a hydroxy group, OR$^8$ (R$^8$ is an optionally substituted hydrocarbon group.) or NR$^9$R$^{10}$ (R$^9$ and R$^{10}$ are the same or different groups which are selected from a hydrogen atom, an optionally substituted hydrocarbon group, an optionally substituted heterocyclic group or an optionally substituted acyl group or R$^9$ and R$^{10}$ combine together to form a ring); R$^4$ and R$^5$ are the same or different groups which are selected from a hydrogen atom or an optionally substituted hydrocarbon group wherein R$^4$ may form a ring with R$^2$; or a salt thereof;

17) A pharmaceutical composition of the above 16) which is a composition for prevention or treatment of diabetes mellitus;
18) A pharmaceutical composition of the above 16) which is a composition for prevention or treatment of hyperlipemia;
19) A pharmaceutical composition of the above 16) which is a composition for prevention or treatment of impaired glucose tolerance;
20) A pharmaceutical composition of the above 16) which is a composition for prevention or treatment of an inflammatory disease; and
21) A pharmaceutical composition of the above 16) which is a composition for prevention or treatment of an arteriosclerosis.
22) An agent for controlling or adjusting retinoid-related receptor comprising a compound represented by Formula (II) of

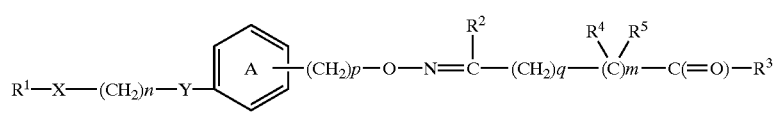

wherein $R^1$ is an optionally substituted hydrocarbon group or an optionally substituted heterocyclic group; X is a bond, —CO—, —CH(OH)— or a group represented by —$NR^6$— wherein $R^6$ is a hydrogen atom or an optionally substituted alkyl group; n is an integer of 1 to 3; Y is an oxygen atom, a sulfur atom, —SO—, —$SO_2$— or a group represented by —$NR^7$— wherein $R^7$ is a hydrogen atom or an optionally substituted alkyl group; ring A is a benzene ring optionally having additional one to three substituents; p is an integer of 1 to 8; $R^2$ is a hydrogen atom, an optionally substituted hydrocarbon group or an optionally substituted heterocyclic group; q is an integer of 0 to 6; m is 0 or 1; $R^3$ is a hydroxy group, $OR^8$ ($R^8$ is an optionally substituted hydrocarbon group.) or $NR^9R^{10}$ ($R^9$ and $R^{10}$ are the same or different groups which are selected from a hydrogen atom, an optionally substituted hydrocarbon group, an optionally substituted heterocyclic group or an optionally substituted acyl group or $R^9$ and $R^{10}$ combine together to form a ring); $R^4$ and $R^5$ are the same or different groups which are selected from a hydrogen atom or an optionally substituted hydrocarbon group wherein $R^4$ may form a ring with $R^2$; or a salt thereof;
23) An agent of the above 22) which is a ligand of a peroxisome proliferator-activated receptors;
24) An agent of the above 22) which is a retinoid X receptor ligand;
25) An agent of the above 22) which is an insulin sensitivity enhancing agent;
26) An agent of the above 22) which is an insulin resistance improving agent;

(1) Definition of $R^1$

A hydrocarbon group in "an optionally substituted hydrocarbon group" represented by $R^1$ in Formulae (I-1) and (II) includes an aliphatic hydrocarbon group, an alicyclic hydrocarbon group, an alicyclic-aliphatic hydrocarbon group, an aromatic-aliphatic hydrocarbon group and an aromatic hydrocarbon group. The number of the carbon atoms in each of these hydrocarbon group is preferably 1 to 14.

(1-1) Definition of Hydrocarbon Group for $R^1$

As the aliphatic hydrocarbon group, an aliphatic hydrocarbon group having 1 to 8 carbon atoms is preferred. Such aliphatic hydrocarbon group includes a saturated aliphatic hydrocarbon group having 1 to 8 carbon atoms (e.g., an alkyl group) such as methyl, ethyl, propyl, isopropyl, butyl, isobutyl, sec-butyl, t-butyl, pentyl, isopentyl, neopentyl, hexyl, isohexyl, heptyl, octyl and the like; an unsaturated aliphatic hydrocarbon group having 2 to 8 carbon atoms (e.g., an alkenyl group, an alkadienyl group, an alkynyl group, an alkadiynyl group and the like) such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like.

As the alicyclic hydrocarbon group, an alicyclic hydrocarbon group having 3 to 7 carbon atoms is preferred. Such alicyclic hydrocarbon group includes a saturated alicyclic hydrocarbon group (e.g., a cycloalkyl group and the like) such as cyclopropyl, cyclobutyl, cyclopentyl, cyclohexyl, cycloheptyl and the like; an unsaturated alicyclic hydrocarbon group (e.g., cycloalkenyl group, cycloalkadienyl group and the like) such as 1-cyclopentenyl, 2-cyclopentenyl, 3-cyclpentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like.

As the alicyclic-aliphatic hydrocarbon group, an alicyclic hydrocarbon group listed above attached to an aliphatic hydrocarbon group listed above (e.g., a cycloalkyl-alkyl group, a cycloalkenyl-alkyl group and the like) are exemplified, and an alicyclic-aliphatic hydrocarbon group having 4 to 9 carbon atom is preferred. Such alicyclic-aliphatic hydrocarbon group includes cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, and the like.

As the aromatic-aliphatic hydrocarbon group, an aromatic-aliphatic hydrocarbon group having 7 to 13 carbon atoms (e.g., an aralkyl group, an arylalkenyl group and the like) is preferred. Such aromatic-aliphatic hydrocarbon group includes a phenylalkyl having 7 to 9 carbon atoms such as benzyl, phenethyl, 1-phenylethyl, 1-phenylpropyl, 2-phenylpropyl, 3-phenylpropyl and the like; a naphthylalkyl having 11 to 13 carbon atoms such as α-naphthylmethyl, α-naphthylethyl, β-naphthylmethyl, β-naphthylethyl and the like; a phenylalkenyl having 8 to 10 carbon atoms such as styryl and the like; a naphthylalkenyl having 12 to 13 carbon atoms such as 2-(2-naphthylvinyl) and the like.

As the aromatic hydrocarbon group, an aromatic hydrocarbon group having 6 to 14 carbon atoms (e.g., an aryl group and the like) is preferred. Such aromatic hydrocarbon group includes phenyl, naphthyl, anthryl, phenanthryl, acenaphthylenyl, biphenylyl and the like, and, among these, those preferred are phenyl, 1-naphthyl, 2-naphthyl and the like.

(1-2) Definition of Heterocyclic Group for $R^1$

A heterocyclic group in "an optionally substituted heterocyclic group" represented by $R^1$ in Formulae (I-1) and (II) includes a 5- to 7-membered monocyclic or condensed heterocyclic group having as its constituent atoms 1 to 4 hetero atoms selected from the group consisting of an oxygen atom, a sulfur atom and a nitrogen atom in addition to carbon atoms. As the condensed heterocyclic ring, a 5- to 7-membered monocyclic heterocyclic ring condensed with a 6-membered ring containing 1 to 2 nitrogen atoms, with a benzene group, or with a 5-membered ring containing one sulfur atom may be exemplified.

Examples of the heterocyclic group are an aromatic heterocyclic group such as 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,3,4-oxadiazol-2-yl, 1,3,4-thiaziazol-2-yl, 1,2,4-triazol-1-yl, 1,2,4-triazol-3-yl, 1,2,3-triazol-1-yl, 1,2,3-triazol-2-yl, 1,2,3-triazol-4-yl, tetrazol-1-yl, tetrazol-5-yl, 2-quinolyl, 3-quinolyl, 4-quinolyl, 2-quinazolyl, 4-quinazolyl, 2-quinoxalyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like as well as a non-aromatic heterocyclic group such as 1-pyrrolidinyl, piperidino, morpholino, thiomorpholino, 1-piperazinyl, 1-hexamethyleneiminyl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl and the like.

A heterocyclic group is preferably pyridyl, oxazolyl, thiazolyl, benzoxazolyl or benzothiazolyl.

(1-3) Definition of Substituents of Hydrocarbon and/or Heterocyclic Group for $R^1$ Each of the hydrocarbon group and the heterocyclic group represented by $R^1$ in Formulae (I-1) and (II) optionally have 1 to 5, preferably 1 to 3 substituents on its possible positions. Such substituents include an optionally substituted aliphatic hydrocarbon group, an optionally substituted alicyclic hydrocarbon group, an optionally substituted aromatic hydrocarbon group, an optionally substituted aromatic heterocyclic group, an optionally substituted non-aromatic heterocyclic group, a halogen atom, a nitro group, an optionally substituted amino group, an optionally substituted acyl group, an optionally substituted hydroxy group, an optionally substituted thiol group, an optionally esterified or amide-derivatized carboxyl group. The substituents represented by "optionally substituted" are a $C_{1-6}$ alkyl group, a $C_{1-6}$ alkoxy group, a halogen (e.g., fluorine, chlorine, bromine, iodine and the like), nitro group, a $C_{1-6}$ halo-alkyl group, a $C_{1-6}$ halo-alkoxy group.

Examples of the aliphatic hydrocarbon group are a straight or branched aliphatic hydrocarbon group having 1 to 15 carbon atoms, such as an alkyl group, an alkenyl group, an alkynyl group and the like.

A preferred alkyl group includes an alkyl group having 1 to 10 carbon atoms such as methyl, ethyl, propyl, isopropyl, butyl, isobutyl, sec-butyl, t-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

A preferred alkenyl group includes an alkenyl group having 2 to 10 carbon atoms, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

A preferred alkynyl group includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

As the alicyclic hydrocarbon group, a saturated or unsaturated alicyclic hydrocarbon group having 3 to 12 carbon atoms, such as a cycloalkyl group, a cycloalkenyl group, a cycloalkadienyl group, may be exemplified.

Preferred examples of the cycloalkyl group are a cycloalkyl group having 3 to 10 carbon atoms, such as cyclopropyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.1.1]nonyl, bicyclo[4.2.1]nonyl, bicyclo[4.3.1]decyl and the like.

Preferred examples of the cycloalkenyl group are a cycloalkenyl group having 3 to 10 carbon atoms, such as 2-cyclopenten-1-yl, 3-cyclopenten-1-yl, 2-cyclohexen-1-yl, 3-cyclohexen-1-yl and the like.

Preferred examples of the cycloalkanedienyl group are a cycloalkanedienyl group having 4 to 10 carbon atoms, such as 2,4-cyclopentadien-1-yl, 2,4-cyclohexadien-1-yl, 2,5-cyclohexadien-1-yl and the like.

Preferred examples of the aromatic hydrocarbon group are an aromatic hydrocarbon group having 6 to 14 carbon atoms (e.g., an aryl group and the like) such as phenyl, naphthyl, anthryl, phenanthryl, acenaphthylenyl, biphenylyl and the like, and, among these, those preferred are phenyl, 1-naphthyl, 2-naphthyl and the like.

Preferred examples of the aromatic heterocyclic group are a 5- to 7-membered aromatic monocyclic group having as its constituent atoms 1 to 4 hetero atoms selected from the group consisting of an oxygen atom, a sulfur atom and a nitrogen atom in addition to carbon atoms, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl and the like; a bicyclic or tricyclic aromatic condensed heterocyclic ring having as its constituent atoms 1 to 5 hetero atoms selected from the group consisting of an oxygen atom, a sulfur atom and a nitrogen atom in addition to carbon atoms, such as benzofuranyl, isobenzofuranyl, benzo[b]thienyl, indolyl, isoindolyl, 1H-indazolyl, benziniidazolyl, benzooxazolyl, benzothiazolyl, 1H-benzotriazolyl, quinolyl, isoquinolyl, cinnolyl, quinazolyl, quinoxalinyl, phthalazinyl, naphthylidinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Preferred examples of the non-aromatic heterocyclic group are oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidinyl, morpholino, thiomorpholino and the like.

Examples of the halogen atom are fluorine, chlorine, bromine and iodine, with fluorine and chlorine being preferred.

An optionally substituted amino group is an amino group optionally mono- or di-substituted with, for example, an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms, an acyl group having 3 to 10 carbon atoms (e.g., an alkanoyl group having 2 to 10 carbon atoms, an arylcarbonyl group having 7 to 13 carbon atoms and the like), or an aryl group having 6 to 12 carbon atoms. The acyl group has the same definition mentioned below for the acyl group in an optionally substituted acyl group.

The substituted amino group includes methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like.

The acyl group in an optionally substituted acyl group is an acyl group having 1 to 13 carbon atoms, such as formyl, as well as a carbonyl group bound to an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms, an aryl group having 6 to 12 carbon atoms and an aromatic heterocyclic group (e.g., thienyl, furyl, pyridyl and the like).

Preferred examples of the acyl group are acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, isonicotinoyl and the like.

The acyl group optionally has one to three substituents on its possible positions, and such substituents include an alkyl group having 1 to 3 carbon atoms, an alkoxy group having 1 to 3 carbon atoms, halogen (e.g., fluorine, chlorine, iodine and the like), nitro, hydroxy, amino and the like.

Other types of acyl groups are represented by a group of the formula: $-COR^{11}$, $-SO_2R^{14}$, $-SOR^{15}$ or $-PO_3R^{16}R^{17}$ wherein $R^{11}$, $R^{14}$, $R^{15}$, $R^{16}$ and $R^{17}$ are independently an optionally substituted hydrocarbon group.

Examples of the "optionally substituted hydrocarbon group" represented by $R^{11}$, $R^{14}$, $R^{15}$, $R^{16}$ and $R^{17}$ are an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms, an aryl group having 6 to 12 carbon atoms.

The optionally substituted hydroxy group includes a hydroxy group, an alkoxy group, an alkenyloxy group, an aralkyloxy group, an acyloxy group, an aryloxy group and the like, each of which may optionally be substituted.

Preferred examples of the alkoxy group are an alkoxy group having 1 to 10 carbon atoms, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy, cyclobutoxy, cyclopentyloxy, cyclohexyloxy and the like.

Preferred examples of the alkenyloxy group are an alkenyloxy group having 2 to 10 carbon atoms, such as allyloxy, crotyloxy, 2-pentenyloxy, 3-hexenyloxy, 2-cyclopentenylmethoxy, 2-cyclohexenylmethoxy and the like.

Preferred examples of the aralkyloxy group are an aralkyloxy group having 7 to 10 carbon atoms such as phenyl-$C_{1-4}$ alkyloxy (e.g., benzyloxy, phenethyloxy and the like) and the like.

Preferred examples of the acyloxy group are an acyloxy group having 2 to 13 carbon atoms, preferably an alkanoyloxy having 2 to 4 carbon atoms (e.g., acetyloxy, propionyloxy, butyryloxy, isobutyryloxy and the like) and the like.

Preferred examples of the aryloxy group are an aryloxy group having 6 to 14 carbon atoms such as phenoxy, naphthyloxy and the like.

Each of an alkoxy group, an alkenyloxy group, an aralkyloxy group, an acyloxy group and an aryloxy group described above may have 1 to 2 substituents on its possible positions, and such substituents include a halogen (e.g., fluorine, chlorine, bromine and the like), or an alkoxy group having 1 to 3 carbon atoms. For example, a substituted aryloxy group may be 4-chlorophenoxy, 2-methoxyphenoxy and the like.

The optionally substituted thiol group includes a thiol, an alkylthio, a cycloalkylthio, an aralkylthio, an acylthio, an arylthio, a heteroarylthio and the like.

Preferred examples of the alkylthio group are an alkylthio group having 1 to 19 carbon atoms such as methylthio, ethylthio, propylthio, isopropylthio, butylthio, isobutylthio, sec-butylthio, t-butylthio, pentylthio, isopentylthio, neopentylthio, hexylthio, heptylthio, nonylthio and the like.

Preferred examples of the cycloalkylthio group are a cycloalkylthio group having 3 to 10 carbon atoms such as cyclobutylthio, cyclopentylthio, cyclohexylthio and the like.

Preferred examples of the aralkylthio group are an aralkylthio group having 7 to 10 carbon atoms such as phenyl-$C_{1-4}$ alkylthio (e.g., benzylthio, phenethylthio and the like) and the like.

Preferred examples of the acylthio group are an acylthio group having 2 to 13 carbon atoms, preferably an alkanoylthio group having 2 to 4 carbon atoms (e.g., acetylthio, propionylthio, butyrylthio, isobutyrylthio and the like) and the like.

Preferred examples of the arylthio group are an arylthio group having 6 to 14 carbon atoms, such as phenylthio, naphthylthio and the like.

Preferred examples of the heteroarylthio group are 2-pyridylthio, 3-pyridylthio as well as 2-imidazolylthio, 1,2,4-triazol-5-ylthio and the like.

The optionally esterified carboxyl group includes a carboxyl group, an alkoxycarbonyl group having 2 to 5 carbon atoms (e.g., methoxycarbonyl, ethoxycarbonyl, propoxycarbonyl, butoxycarbonyl and the like), an aralkyloxycarbonyl group having 8 to 10 carbon atoms (e.g., benzyolxycarbonyl and the like), an aryloxycarbonyl group having 7 to 15 carbon atoms optionally substituted with one or two alkyl groups having 1 to 3 carbon atoms (e.g., phenoxycarbonyl, p-tolyloxycarbonyl and the like) and the like.

The optionally substituted amide-derived carboxyl group includes a group represented by Formula: $-CON(R^{12})(R^{13})$ wherein $R^{12}$ and $R^{13}$ may be same or different and is hydrogen, an optionally substituted hydrocarbon group or an optionally substituted heterocyclic group.

The hydrocarbon group and the heterocyclic group in "an optionally substituted hydrocarbon group" and "an optionally substituted heterocyclic group" represented by $R^{12}$ and $R^{13}$ includes an aliphatic hydrocarbon group, an alicyclic hydrocarbon group and an aromatic hydrocarbon group and heterocyclic group exemplified as the same described in the above (1-1) and (1-2), respectively. Such hydrocarbon groups and heterocyclic groups optionally have 1 to 3 substituents on possible positions, and such substituents include a halogen (e.g., fluorine, chlorine, bromine, iodine and the like), an alkyl group having 1 to 4 carbon atoms, an alkoxy group having 1 to 4 carbon atoms and the like.

A substituent in the hydrocarbon group and the heterocyclic group represented by $R^1$ in Formulae (I-1) and (II) is preferably an alkyl group having 1 to 10 carbon atoms, a cycloalkyl group having 1 to 10 carbon atoms, an aromatic heterocyclic group, an aryl group having 6 to 14 carbon atoms, more preferably an alkyl group having 1 to 3 carbon atoms, a cycloalkyl group having 3 to 7 carbon atoms, furyl, thienyl, phenyl and naphthyl.

The substituent in the hydrocarbon group and the heterocyclic group represented by $R^1$, when it is an alicyclic hydrocarbon group, an aromatic hydrocarbon group, an aromatic heterocyclic group or a non-aromatic heterocyclic group, optionally have one or more, preferably 1 to 3 appropriate substituents, and such substituents include an alkyl group having 1 to 6 carbon atoms, an alkenyl group having 2 to 6 carbon atoms, a cycloalkyl group having 3 to 10 carbon atoms, an aryl group having 6 to 14 carbon atoms (e.g., phenyl, naphthyl and the like), an aromatic heterocyclic group (e.g., thienyl, furyl, pyridyl, oxazolyl, thiazolyl and the like), a non-aromatic heterocyclic group (e.g., tetrahydrofuryl, morpholino, thiomorpholino, piperidino, pyrrolidinyl, piperazinyl and the like), an aralkyl group having 7 to 9 carbon atoms, amino group, an amino group mono- or di-substituted with an alkyl group having 1 to 4 carbon atoms or with an acyl group having 2 to 8 carbon atoms (e.g., an alkanoyl group and the like), an amidino group, an acyl group having 2 to 8 carbon atoms (e.g., alkanoyl group and the like), carbamoyl group, a carbamoyl group mono- or di-substituted with an alkyl group having 1 to 4 carbon atoms, sulfamoyl group, a sulfamoyl group mono- or di-substituted with an alkyl group having 1 to 4 carbon atoms, carboxyl group, an alkoxycarbonyl group having 2 to 8 carbon atoms, hydroxy group, an alkoxy group having 1 to 6 carbon atoms, an alkenyloxy group having 2 to 5 carbon atoms, a cycloalkyloxy group having 3 to 7 carbon atoms, an aralkyldxy group having 7 to 9 carbon atoms, an aryloxy group having 6 to 14 carbon atoms (e.g., phenyloxy, naphthyloxy and the like), thiol group, an alkylthio group having 1 to 6 carbon atoms, an aralkylthio group having 7 to 9 carbon atoms, an arylthio group having 6 to 14 carbon atoms (e.g., phenylthio, naphthylthio and the like), sulfonyl group, cyano group, azide group, nitro group, nitroso group, a halogen atom (e.g., fluorine chlorine, bromine, iodine) and the like.

(1-4) Preferred Examples of $R^1$ $R^1$ in Formulae (I-1) and (II) is preferably an optionally substituted heterocyclic group, and more preferably pyridyl, oxazolyl, thiazolyl or triazolyl each of which is optionally substituted. A particularly preferable $R^1$ is pyridyl, oxazolyl, thiazolyl or triazolyl which optionally have 1 to 2 substituents selected from the group consisting of an alkyl having 1 to 3 carbon atoms, a cycloalkyl having 3 to 7 carbon atoms, furyl, thienyl, phenyl and naphthyl. The furyl, thienyl, phenyl and naphthyl optionally have substituents selected from an alkyl having 1 to 3 carbon atoms, an alkoxy having 1 to 3 carbon atoms, a halogen (e.g., fluorine, chlorine, bromine, iodine and the like) and halo-alkyl having 1 to 3 carbon atoms.

Such preferred ring of an optionally substituted heterocyclic group or an optionally substituted cyclic hydrocarbon group of $R^1$ is selected from the group represented by the formulae of

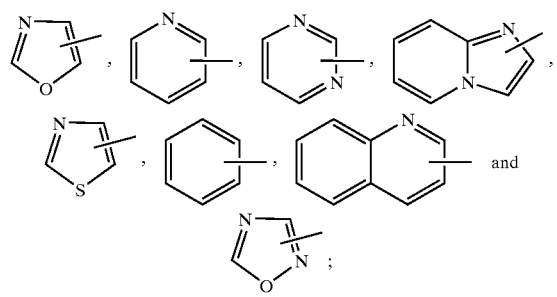

The ring optionally has one or two substituents which are selected from the group of a phenyl, a furyl, a thienyl and a $C_{1-4}$ alkyl. The group of a phenyl, a furyl and a thienyl optionally have substituents selected from $C_{1-6}$ alkyl group, $C_{1-6}$ alkoxy group, a halogen (e.g., fluorine, chlorine, bromine, iodine and the like), nitro group, $C_{1-6}$ halo-alkyl group, or $C_{1-6}$ halo-alkoxy group.

Further preferred one for $R^1$ is a formula of

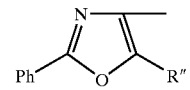

wherein Ph is an optionally substituted phenyl group, and R" is a hydrogen or an optionally substituted $C_{1-6}$ alkyl group.

The substituents of Ph and the $C_{1-6}$ alkyl group of R" are a $C_{1-6}$ alkoxy group, a halogen (e.g., fluorine, chlorine, bromine, iodine and the like), a nitro group, a $C_{1-6}$ halo-alkyl group or a $C_{1-6}$ halo-alkoxy group.

(2) Definition of X

In Formulae (I-1), (I-2) and (II), X is a bond, —CO—, —CH(OH)— or a group represented by —NR$^6$— wherein $R^6$ is hydrogen, an optionally substituted alkyl group, with a bond, —CH(OH)— or —NR$^6$— being preferred and a bond or —NR$^6$— being more preferred.

An alkyl group in "an optionally substituted alkyl group" represented by $R^6$ includes an alkyl group having 1 to 4 carbon atoms, such as methyl, ethyl, propyl, isopropyl, butyl, isobutyl, sec-butyl, t-butyl and the like. Such alkyl group optionally have 1 to 3 substituents on its possible positions, and such substituents include a halogen (fluorine, chlorine, bromine, iodine), an alkoxy group having 1 to 4 carbon atoms (e.g., methoxy, ethoxy, propoxy, isopropoxy, butoxy, isobutoxy, sec-butoxy, t-butoxy and the like), hydroxy group, nitro group, an acyl group having 1 to 4 carbon atoms (e.g., an alkanoyl group having 1 to 4 carbon atoms such as formyl, acetyl, propionyl and the like).

(3) Definition of n & Y

In Formulae (I-1), (I-2) and (II), n is an integer of 1 to 3, preferably 1 to 2.

In Formulae (I-1), (I-2) and (II), Y is —O—, —S—, —SO—, —SO$_2$— or —NR$^7$— wherein $R^7$ is hydrogen, an optionally substituted alkyl group, with —O—, —S— or —NR$^7$— being preferred. "An optionally substituted alkyl group" represented by $R^7$ includes those exemplified as "an optionally substituted alkyl group" represented by $R^6$ described above.

(4) Definition of Ring A

Ring A in Formulae (I-1), (I-2) and (II) represents a benzene ring, and optionally has an additional 1 to 3 substituents on its possible positions. Such substituents include an alkyl group, an optionally substituted hydroxy group, a halogen atom, an optionally substituted acyl group, nitro group, and an optionally substituted amino group, each of which is exemplified as a substituent on a hydrocarbon group and a heterocyclic group represented by $R^1$.

Such substituent is preferably an alkyl group having 1 to 4 carbon atoms, an alkoxy group having 1 to 4 carbon atoms or a halogen atom. The ring A is preferably a non-substituted benzene ring.

In Formulae (I-1) and (II), moiety:

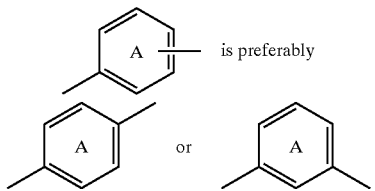

is preferably (5) Definition of P

In Formulae (I-1), (I-2) and (II), p is an integer of 1 to 8, preferably an integer of 1 to 3.

(6) Definition of $R^2$

In Formulae (I-1), (I-2) and (II), "an optionally substituted hydrocarbon group" represented by $R^2$ may be one exemplified as "an optionally substituted hydrocarbon group" represented by $R^1$.

"An optionally substituted heterocyclic group" represented by $R^2$ may be one exemplified as "an optionally substituted heterocyclic group" represented by $R^1$.

In Formulae (I-1), (I-2) and (II), $R^2$ is preferably an optionally substituted hydrocarbon group. More preferably, $R^2$ is an aliphatic hydrocarbon group, an alicyclic hydrocarbon group, an aromatic-aliphatic hydrocarbon group or an aromatic hydrocarbon group each of which is optionally substituted, and particularly preferred is an alkyl group having 1 to 4 carbon atoms, a phenylalkyl group having 8 to 10 carbon atoms, an aryl group having 6 to 14 carbon atoms, each of which is optionally substituted.

A substituent which is optionally present on each of the hydrocarbon groups described above is preferably a halogen atom, an alkoxy group having 1 to 4 carbon atoms, an aryloxy group having 6 to 14 carbon atoms and an aromatic heterocyclic group (e.g., furyl, thienyl).

(7) Definition of q and m

In Formulae (I-1) and (I-2), q is an integer of 0 to 6, preferably 0 to 4. m is 0 or 1. In Formula (I-1) where $R^1$ is ethoxymethyl, a $C_{1-3}$ alkyl, phenyl or p-methoxyphenyl, q is an integer of 1 to 6.

In Formula (II), q is an integer of 0 to 6, preferably 0 to 4. m is 0 or 1.

(8) Definition of $R^3$ $R^3$ is a hydroxy group, $OR^8$ ($R^8$ is an optionally substituted hydrocarbon group.) or $NR^9R^{10}$ ($R^9$ and $R^{10}$ are the same or different groups which are selected from a hydrogen atom, an optionally substituted hydrocarbon group, an optionally substituted heterocyclic group or an optionally substituted acyl group or $R^9$ and $R^{10}$ combine together to form a ring).

In Formulae (I-1), (I-2) and (II), "an optionally substituted hydrocarbon group" represented by $R^8$ includes one exemplified as "an optionally substituted hydrocarbon group" represented by $R^1$. A particularly preferred $R^3$ is hydroxy group.

In Formulae (I-1), (I-2) and (II), "an optionally substituted hydrocarbon group" represented by $R^9$ and $R^{10}$ includes one exemplified as "an optionally substituted hydrocarbon group" represented by $R^1$.

In Formulae (I-1), (I-2) and (II), "an optionally substituted heterocyclic group" represented by $R^9$ and $R^{10}$ includes one exemplified as "an optionally substituted heterocyclic group" represented by $R^1$.

In Formulae (I-1), (I-2) and (II), "an optionally substituted acyl group" represented by $R^9$ and $R^{10}$ includes one exemplified as "an optionally substituted acyl group" represented by $R^1$.

In Formulae (I-1), (I-2) and (II), $R^9$ and $R^{10}$ optionally combine together to form a ring such as 1-pyrrolidinyl, 1-piperidinyl, 1-hexamethyleneiminyl, 4-morpholino, or 4-thiomorpholino.

(9) Definition of $R^4$ & $R^5$

"An optionally substituted alkyl group" represented by $R^4$ and $R^5$ in Formulae (I-1) and (II) includes the same as "an optionally substituted alkyl group" represented by $R^6$ described above.

"An optionally substituted hydrocarbon group" and "an optionally substituted heterocyclic group" represented by $R^9$ and $R^{10}$ in Formulae (I-1), (I-2) and (II) includes the same as "an optionally substituted hydrocarbon group" and "an optionally substituted heterocyclic group" represented by $R^{12}$ and $R^{13}$, respectively, described above.

"An optionally substituted hydrocarbon group" represented by $R^{11}$ in Formulae (I-1), (1-2) and (II) includes an alkyl group having 1 to 4 carbon atoms, an aryl group having 6 to 10 carbon atoms optionally substituted with an alkyl group having 1 to 4 carbon atoms or with a halogen atom. Such alkyl group having 1 to 4 carbon atoms in "an alkyl group having 1 to 4 carbon atoms" and "an aryl group having 6 to 10 carbon atoms optionally substituted with an alkyl group having 1 to 4 carbon atoms or with a halogen atom" represented by $R^8$ includes methyl, ethyl, propyl, butyl, isobutyl, sec-butyl, t-butyl and the like, with methyl and ethyl being preferred. A halogen in "an aryl group having 6 to 10 carbon atoms optionally substituted with an alkyl group having 1 to 4 carbon atoms or with a halogen atom" includes fluorine, chlorine, bromine, iodine and the like, with chlorine being preferred, and an aryl group having 6 to 10 carbon atoms may include phenyl and naphthyl, with phenyl being preferred.

(10) E-Form and/or Z-Form Compound

A compound represented by Formulae (I-1), (I-2) and (II) is present in E- and Z-isomers with regard to the imino bond. Said compound may be either single one of E- or Z-form, or may be the mixture of the two.

O-[2-chloro-4-(2-quinolylmethoxy)phenylmethyl]oxime of methyl pyruvate and [2-chloro-4-(2-quinolylmethoxy)phenylmethyl]-2-iminoxy propionic acid are known compounds disclosed in WO96/02507, and excluded from Formula (I-1).

(11) Preferred Embodiments

Among the compounds of Formula (I-1), one of the preferred embodiments of the present invention is a compound represented by the formula of

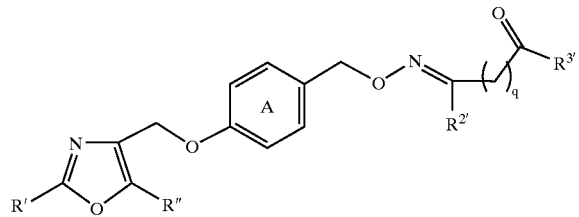

wherein R' is a phenyl, furyl or thienyl which optionally has substituents selected from a $C_{1-6}$ alkyl group, a $C_{1-6}$ alkoxy group, a halogen (e.g., fluorine, chlorine, bromine, iodine and the like), nitro group, a $C_{1-6}$ halo-alkyl group, a $C_{1-6}$ halo-alkoxy group; R″ is a hydrogen or an optionally substituted $C_{1-6}$ alkyl (more preferably a hydrogen, methyl or ethyl); $R^{2'}$ is a phenyl which is optionally substituted by at least one substituent selected from a group of a hydrogen, a $C_{1-6}$ alkyl, a $C_{1-6}$ alkoxy and a halogen; q is an integer of 1 to 6; and $R^{3'}$ is a hydroxy, a $C_{1-6}$ alkoxy or —$NR^9R^{10}$ in which $R^9$ and $R^{10}$ are independently selected from the group of a hydrogen atom, an optionally substituted hydrocarbon group, an optionally substituted heterocyclic group or an optionally substituted acyl group, or $R^9$ and $R^{10}$ combine together to form a ring; ring A is an optionally substituted benzene ring; or a salt thereof.

Another preferred embodiment of the present invention is a compound represented by a formula of

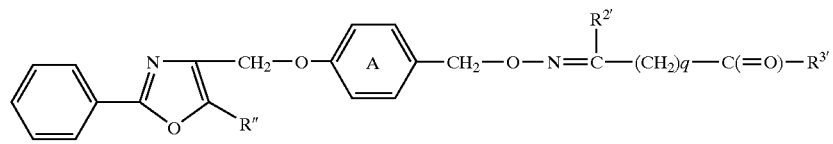

wherein each symbol has the same definition mentioned above; or a salt thereof.

Preferred specific examples of the compound represented by Formulae (I-1), (I-2) and (II) are Compound (1) to (10) listed below.

(1) Z-2-[4-(5-methyl-2-phenyl-4-oxazolylmethoxy) benzyloxyimino-2-phenylacetic acid
(2) Z-4-[4-(5-methyl-2-phenyl-4-oxazolylmethoxy) benzyloxyimino]-4-phenylbutyric acid
(3) Z-2-(4-bromophenyl)-2-[4-(5-methyl-2-phenyl-4-oxazolylmethoxy)benzyloxyimino]acetic acid
(4) Z-2-[4-(5-methyl-2-phenyl-4-oxazolylmethoxy) benzyloxyimino]-2-(4-phenoxyphenyl)acetic acid
(5) Z-4-(4-fluorophenyl)-4-[4-(5-methyl-2-phenyl-4-oxazolylmethoxy)benzyloxyimino]butyric acid
(6) Z-3-methyl-2-[4-(5-methyl-2-phenyl-4-oxazolylmethoxy)benzyloxyimino]butyric acid
(7) E-4-[4-(5-methyl-2-phenyl-4-oxazolylmethoxy) benzyloxyimino]-4-phenylbutyric acid
(8) E-4-(4-fluorophenyl)-4-[4-(5-methyl-2-phenyl-4-oxazolylmethoxy)benzyloxyimino]butyric acid
(9) E-4-[4-(5-methyl-2-phenyl-4-oxazolylmethoxy) benzyloxyimino]-4-phenylbutyramide
(10) E-8-[4-(5-methyl-2-phenyl-4-oxazolylmethoxy) benzyloxyimino]-8-phenyloctanoic acid These compounds may hereinafter be abbreviated as Compound (1), Compound (2) or the like.

(12) Examples of Salts

A salt of a compound represented by Formula (I-1), (I-2) or (II) (which may hereinafter be abbreviated as Compound (I-1), (I-2) or (II)) is preferably a pharmacologically acceptable salt, such as a salt with an inorganic base, a salt with an organic base, a salt with an inorganic acid, a salt with an organic salt, a salt with a basic or acidic amino acid and the like.

Preferred examples of the salt with an inorganic base are an alkali metal salt such as a sodium salt and a potassium salt; an alkaline earth metal salt such as a magnesium salt; as well as an aluminum salt and an ammonium salt and the like.

Preferred examples of the salt with an organic base are salts with trimethylamine, triethylamine, pyridine, picoline, ethanolamine, diethanolamine, triethanolamine, dicyclohexylamine, N,N-dibenzylethylenediamine and the like.

Preferred examples of the salt with an inorganic acid are salts with hydrochloric acid, hydrobromic acid, nitric acid, sulfuric acid, phosphoric acid and the like.

Preferred examples of the salt with an organic acid are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferred examples of the salt with a basic amino acid are salts with arginine, lysine, ornithine and the like, while preferred examples of a salt with an acidic amino acid are salts with aspartic acid, glutamic acid and the like.

Among the salts described above, those preferred are sodium salts, potassium salts, hydrochlorides and the like.

(13) Formulation

A compound represented by Formula (I-1), (I-2) or (II) and a salt thereof (which may hereinafter be abbreviated as a compound according to the present invention) has a low toxicity, and can be formulated together with a pharmacologically acceptable carrier into a pharmaceutical composition, which may be used as an agent for prevention and/or treatment of various diseases discussed below in mammals (e.g., human, mouse, rat, rabbit, dog, cat, cattle, horse, swine, monkey and the like).

The pharmacologically acceptable carrier employed here is selected from various customary organic or inorganic materials used as materials for pharmaceutical formulations, and may be incorporated as excipients, glidants, binders and disintegrants in a solid formulation; vehicles, solubilizers, suspending agents, tonicity agents, buffer, analgesic agents in a liquid formulation. If necessary, pharmaceutical additives such as preservatives, antioxidants, colorants, sweeteners may also be added.

Preferred examples of the excipients are lactose, sugar, D-mannitol, D-sorbitol, starch, α-starch, dextrin, crystalline cellulose, low-substituted hydroxypropyl cellulose, sodium carboxymethylcellulose, gum arabic, pullulan, light silicic anhydride, synthetic aluminum silicate, magnesium aluminate metasilicate and the like.

Preferred examples of the glidants are magnesium stearate, calcium stearate, talc, colloidal silica and the like.

Preferred examples of the binders are α-starch, sucrose, gelatin, gum arabic, methylcellulose, carboxymethylcellulose, sodium carboxymethylcellulose, crystalline cellulose, sugar, D-mannitol, trehalose, dextrin, pullulan, hydroxypropylcellulose, hydroxypropylmethylcellulose, polyvinylpyrrolidone and the like.

Preferred examples of the disintegrants are sugar, starch, carboxymethylcellulose, potassium carboxymethylcellulose, croscarmellose sodium, sodium carboxymethyl starch, light silicic anhydride, low-substituted hydroxypropylcellulose and the like.

Preferred examples of the vehicles are water for injection, physiological saline, Ringer's solution, alcohols, propylene glycol, polyethylene glycol, sesame oil, corn oil, olive oil, cotton seed oil and the like.

Preferred examples of the solubilizers are polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agents are a surfactant such as stearyltriethanolamine, sodium laurylsulfate, laurylaminopropionic acid, lecithin, benzalkonium chloride, benzethonium chloride, glycerin monostearate and the like; a hydrophilic polymer such as polyvinylalcohol, polyvinylpyrrolidone, sodium carboxymethylcellulose, methylcellulose, hydroxymethylcellulose, hydroxyethylcellulose, hydroxypropylcellulose and the like; and polysorbates, polyoxyethylene hydrogenated castor oil and the like.

Preferred examples of the tonicity agents are sodium chloride, glycerin, D-mannitol, D-sorbitol, glucose and the like.

Preferred examples of the buffer solution are the solutions of phosphates, acetates, carbonates, citrates and the like.

Preferred examples of the analgesic agents includes benzylalcohol and the like.

Preferred examples of the preservatives are p-oxybenzoates, chlorobutanol, benzylalcohol, phenethylalcohol, dehydroacetic acid, sorbic acid and the like.

Preferred examples of the antioxidants are sulfites, ascorbates and the like.

Preferred examples of the colorants are a water soluble tar pigments (e.g., edible pigments such as edible color Red No.2 and No.3, edible color Yellow No.4 and No.5, edible color Blue No.1 and No.2), a water-insoluble lake pigments (e.g., aluminum salts of the water soluble edible tar pigments listed above and the like), a natural pigment (e.g., β-carotene, chlorophyll, iron oxide red and the like) and the like.

Preferred examples of the sweeteners are saccharin sodium, potassium glycyrrhizinate, Aspartame, steviocides and the like.

(14) Dosage Form

A dosage form of a pharmaceutical composition includes an oral formulation such as a capsule (including a soft capsule and a microcapsule), a granule, a powder, a syrup, an emulsion, a suspension and the like; a non-oral formulation such as a formulation for injection (e.g., subcutaneous injection formulation, intravenous injection formulation, intramuscular injection formulation, intraperitoneal injection formulation and the like), a formulation for drip infusion, a formulation for external application (e.g., nasal formulation, percutaneous formulation, ointments and the like), a suppository (e.g., rectal suppository, vaginal suppository and the like), a pellet, a formulation for drip infusion and the like, all of which can safely be given via an oral or a non-oral route.

The pharmaceutical composition may be produced by a conventional method in the field of pharmaceutical technology, for example, a method described in Japanese Pharmacopoeia. A method for producing a formulation is described in detail below.

An oral formulation is, for example, prepared by admixing an active ingredient with an excipient (e.g., lactose, sugar, starch, D-mannitol and the like), a disintegrant (e.g., calcium carboxymethylcellulose and the like), a binder (e.g., α starch, gum arabic, carboxymethylcellulose, hydroxypropylcellulose, polyvinylpyrrolidone and the like), or a glidant (e.g., talc, magnesium stearate, polyethylene glycol 6000 and the like), followed by compaction molding, further followed, if necessary, by coating with a coating base by a known method for the purpose of masking a taste, obtaining an enteric dissolution or a sustained release.

Such coating base includes a sugar coating base, a water soluble film coating base, an enteric coating base, a sustained release film coating base and the like.

A sugar coating base includes a sugar, which may be used in combination with one or more materials selected from the group consisting of talc, sedimentation calcium carbonate, gelatin, gum arabic, pullulan, carnauba wax and the like.

A water soluble film coating base includes a cellulose-based polymer such as hydroxypropylcellulose, hydroxypropylmethylcellulose, methylhydroxyethylcellulose and the like; a synthetic polymer such as polyvinylacetal diethylaminoacetate, aminoalkylmethacrylate copolymer E [Eudragit E (trade name), Röhm Pharma], polyvinylpyrrolidone and the like; and a polysaccharide such as pullulan.

An enteric film coating base includes a cellulose-based polymer such as hydroxypropylmethylcellulose phthalate, hydroxypropylmethylcellulose acetate succinate, carboxymethylethylcellulose, cellulose acetate phthalate and the like; an acrylic acid-based polymer such as methacrylic acid copolymer L [Eudragit L (trade name), Röhm Pharma], methacrylic acid copolymer LD [Eudragit L-30D55 (trade name), Röhm Pharma], methacrylic acid copolymer S [Eudragit S (trade name), Röhm Pharma]and the like; a naturally-occurring material such as shellac.

A sustained release film coating base includes a cellulose-based polymer such as ethylcellulose; an acrylic acid-based polymer such as aminoalkylmethacrylate copolymer RS [Eudragit RS (trade name), Röhm Pharma], ethylacrylate-methylmethacrylate copolymer suspension [Eudragit NE (trade name), Röhm Pharma] and the like.

A mixture of two or more coating bases described above may also be employed in a certain appropriate ratio. A light-shielding material such as titanium oxide and iron dioxide or trioxide may also be employed in the coating.

An injection formulation may be prepared by dissolving, suspending or emulsifying an active ingredient together with a dispersant (e.g., polysorbate 80, polyoxyethylene hydrogenated castor oil 60 and the like), polyethylene glycol, carboxymethylcellulose, sodium alginate and the like, a preservative (e.g., methylparaben, propylparaben, benzylalcohol, chlorobutanol, phenol and the like), a tonicity agent (e.g., sodium chloride, glycerin, D-mannitol, D-sorbitol, glucose and the like) and the like, in an aqueous solvent (e.g., distilled water, physiological saline, Ringer's solution and the like) or a lipophilic solvent (e.g., a vegetable oil such as olive oil, sesame oil, cotton seed oil, corn oil and the like or propylene glycol). In this procedure, an additive such as a solubilizer (e.g. sodium salicylate, sodium acetate and the like), a stabilizer (e.g., human serum albumin and the like), an analgesic agent (e.g., benzylalcohol and the like) may also be employed if necessary.

(15) Composition

The other aspect of the present invention is a pharmaceutical composition comprising a compound represented by Formula (II)

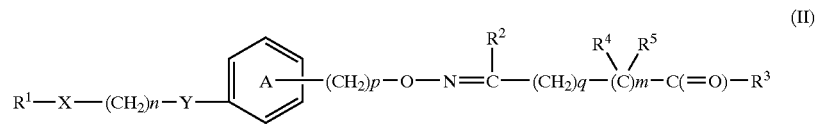

(II)

wherein R¹ is an optionally substituted hydrocarbon group or an optionally substituted heterocyclic group; X is a bond, —CO—, —CH(OH)— or a group represented by —NR⁶— wherein R⁶ is a hydrogen atom or an optionally substituted alkyl group; n is an integer of 1 to 3; Y is an oxygen atom, a sulfur atom, —SO—, —SO₂— or a group represented by —NR⁷— wherein R⁷ is a hydrogen atom or an optionally substituted alkyl group; ring A is a benzene ring optionally having additional one to three substituents; p is an integer of 1 to 8; R² is a hydrogen atom, an optionally substituted hydrocarbon group or an optionally substituted heterocyclic group; q is an integer of 0 to 6; m is 0 or 1; R³ is a hydroxy group, OR⁸ (R⁸ is an optionally substituted hydrocarbon group.) or NR⁹R¹⁰ (R⁹ and R¹⁰ are the same or different groups which are selected from a hydrogen atom, an optionally substituted hydrocarbon group, an optionally substituted heterocyclic group or an optionally substituted acyl group or R⁹ and R¹⁰ combine together to form a ring); R⁴ and R⁵ are the same or different groups which are selected from a hydrogen atom or an optionally substituted hydrocarbon group wherein R⁴ may form a ring with R²; or a salt thereof. Each above-mentioned substituent has the same detailed definition of the corresponding one defined for Formula (I-1).

Especially, the pharmaceutical composition can be used for prevention or treatment of diseases such as diabetes mellitus, hyperlipemia, impaired glucose tolerance, an inflammatory disease, an arteriosclerosis and the like.

Among these compositions, a preferred one is a composition comprising a compound represented by a formula of

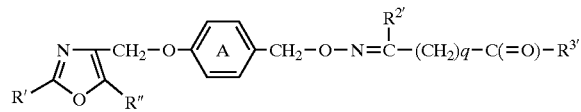

wherein R' is a phenyl, furyl or thienyl which optionally has substituents selected from a $C_{1-6}$ alkyl group, a $C_{1-6}$ alkoxy group, a halogen (e.g., fluorine, chlorine, bromine, iodine and the like), nitro group, a $C_{1-6}$ halo-alkyl group, a $C_{1-6}$ halo-alkoxy group; R" is a hydrogen or a $C_{1-6}$ alkyl (more preferably, a hydrogen, methyl or ethyl); R² is a phenyl which is optionally substituted by at least one substituent selected from a group of a hydrogen, a $C_{1-6}$ alkyl, a $C_{1-6}$ alkoxy and a halogen; q is an integer of 1 to 6; and R³' is a hydroxy, an alkoxy or —NR⁹R¹⁰ in which R⁹ and R¹⁰ are independently selected from the group of a hydrogen atom, an optionally substituted hydrocarbon group, an optionally substituted heterocyclic group or an optionally substituted acyl group, or R⁹ and R¹⁰ combine together to form a ring; a ring A is an optionally substituted benzene ring; or a salt thereof.

Another preferred composition of the present invention is a composition comprising a compound represented by a formula of

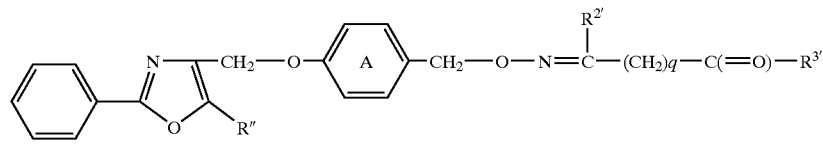

wherein each symbol has the same definition mentioned above; or a salt thereof.

(16) Agent

According to the useful function of the compound of the present invention, the compound can be used as an insulin sensitivity enhancing agent; an insulin resistance improving agent; an agent for controlling or adjusting retinoid-related receptor; a ligand of a peroxisome proliferator-activated receptors; a retinoid X receptor ligand; etc.

A compound according to the present invention has a blood sugar reducing effect, a blood lipid reducing effect, a blood insulin reducing effect, an insulin sensitivity enhancing effect, an insulin resistance improving effect and retinoid-related receptor function adjuster activities. A retinoid-related receptor used here is encompassed in nuclear receptors, and is a DNA-binding transcription factor having as a function adjuster a signal molecule such as an oil-soluble vitamin, and may be any of a monomer receptor, a homodimer receptor and a heterodimer receptor.

A monomer receptor is exemplified by retinoid O receptor (hereinafter abbreviated occasionally as ROR) α (GenBank Accession No.L14611), RORβ (GenBank Accession No.L14160), RORγ (GenBank Accession No.U16997); Rev-erbα (GenBank Accession No.M24898), Rev-erbβ (GenBank Accession No.L31785); ERRα (GenBank Accession No.X51416), ERRβ (GenBank Accession No.X51417); Ftz-FIα (GenBank Accession No.S65876), Ftz-FIβ (GenBank Accession No.M81385); TIx (GenBank Accession No.S77482); GCNF (GenBank Accession No.U14666) and the like.

A homodimer receptor may for example be a homodimer formed from retinoid X receptor (hereinafter abbreviated occasionally as RXR) α (GenBank Accession No.X52773), RXRβ (GenBank Accession No.M84820), RXRγ (GenBank Accession No.U38480); COUPα (GenBank Accession No.X12795), COUPβ (GenBank Accession No.M64497), COUPγ (GenBank Accession No.X12794); TR2α (GenBank Accession No.M29960), TR2β (GenBank Accession No.L27586); or, HNF4α (GenBank Accession No.X76930), HNF4γ (GenBank Accession No.Z49826) and the like.

A heterodimer receptor may for example be a heterodimer formed from retinoid receptor X (RXRα, RXRβ or RXRγ) described above together with one receptor selected from the group consisting of retinoid A receptor (hereinafter abbreviated occasionally as RAR) α (GenBank Accession No.X06614), RARβ (GenBank Accession No.Y00291), RARγ (GenBank Accession No.M24857); a thyroidal hormone receptor (hereinafter abbreviated occasionally as TR) α (GenBank Accession No.M24748), TRβ (GenBank Accession No.M26747); a vitamin D receptor (VDR) (GenBank Accession No.303258); a peroxisome proliferator-activated receptor (hereinafter abbreviated occasionally as PPAR) α (GenBank Accession No.L02932), PPARβ (PPAR δ) (GenBank Accession No.U10375), PPARγ (GenBank Accession No.L40904); LXRα (GenBank Accession No.U22662), LXRβ (GenBank Accession No.U14534); FXR (GenBank Accession No.U18374); MB67 (GenBank Accession No.L29263); ONR (GenBank Accession No.X75163); and NURα (GenBank Accession No.L13740), NURβ (GenBank Accession No.X75918), NURγ (GenBank Accession No.U12767).

Compound (I-1) and its salts exhibit excellent function adjuster activity especially toward retinoid X receptors (RXRα, RXRβ, RXRγ) and peroxisome proliferator-activated receptors (PPARα, PPARβ (PPAR δ), PPARγ) among those retinoid-related receptors listed above.

In addition, Compound (II) or its salts exhibit excellent ligand activity toward a heterodimer receptor formed from a retinoid X receptor and a peroxisome proliferator-activated receptor, preferably a peroxisome proliferator-activated receptor as in the heterodimer receptor formed from RXRα and PPARγ.

Accordingly, a retinoid-related receptor function adjuster according to the present invention is used advantageously as a peroxisome proliferator-activated receptor ligand or a retinoid X receptor ligand.

(17) Diseases to be Treated

Accordingly, a compound or a pharmaceutical composition according to the present invention can be used for the prevention or treatment of diabetes mellitus (e.g., insulin-dependent diabetes mellitus(type-1 diabetes mellitus), non-insulin-dependent diabetes mellitus (type-2 diabetes mellitus), pregnancy diabetes mellitus and the like), hyperlipemia (e.g., hypertriglycemia, hypercholesterolemia, hypoHDLemia and the like), insulin insensitivity, insulin resistance, and impaired glucose tolerance (IGT).

A compound or a pharmaceutical composition according to the present invention may also be used for the prevention or treatment of diabetic complications (e.g., neuropathy, nephropathy, retinopathy, cataract, large blood vessel disorders, osteopenia and the like), obesity, osteoporosis, cachexia (e.g., carcinomatous cachexia, tuberculous cachexia, diabetic cachexia, hemophathic cachexia, endocrinopathic cachexia, infectious cachexia or cachexia induced by acquired immunodeficiency syndrome), fatty liver, hypertension, polycystic ovary syndrome, renal disorders (e.g., glomerular nephritis, glomerulosclerosis, nephrotic syndrome, hypertensive nephrosclerosis, terminal renal disorders and the like), muscular dystrophy, myocardiac infarction, angina pectoris, cerebral infarction, insulin resistance syndrome, syndrome X, hyperinsulinemia-induced sensory disorder, tumors (e.g., leukemia, breast cancer, prostate cancer, skin cancer and the like), inflammatory diseases (e.g., rheumatoid arthritis, spondylitis deformans, osteoarthritis, lumbago, gout, surgical wound inflammation and swelling remedy, neuralgia, pharyngolaryngitis, cystitis, hepatitis, pneumonia, pancreatitis and the like), arterial sclerosis (e.g., atherosclerosis and the like).

A compound according to the invention may also be employed as a pharmaceutical for controlling appetite, food intake, diet and anorexia.

While the dose of a compound or a pharmaceutical composition according to the present invention varies depending on various factors such as the subject to be treated, the administration route, the disease or the condition to be treated, a compound according to the present invention as an active ingredient may for example be given orally to an adult at a single dose of about 0.05 to 100 mg/kg body weight, preferably about 0.1 to 10 mg/kg body weight, preferably one to three times a day.

(18) Combination Use of Drugs

A compound according to the present invention may be used in combination with a diabetes mellitus-treating agent, a diabetic complication-treating agent, an antihyperlipemic agent, a hypotensive agent, an anti-obesity agent, a diuretic, a chemotherapeutic agent, an immunotherapeutic agent and the like (hereinafter referred to as a concomitant agent). In such case, the periods of the treatments with a compound according to the present invention and with a concomitant agent are not limited particularly, and such agents may given to a patient simultaneously or at a certain time interval. The dose of a concomitant drug may appropriately be determined based on the customary clinical dose. The ratio between a compound according to the present invention and a concomitant agent may be appropriately determined based on various factors such as the subject to be treated, the administration route, the disease or the condition to be treated and the combination of the drugs. For example, when a human is treated, 1 part by weight of a compound according to the present invention is combined with 0.01 to 100 parts by weight of a concomitant agent.

Examples of an agent for treating diabetes mellitus are an insulin formulation (e.g., animal insulin formulations extracted from a pancreas of a cattle or a swine; a human insulin formulation synthesized by a gene engineering technology using colibacillus and yeasts), an insulin sensitivity enhancing agent (e.g., pioglitazone hydrochloride, troglitazone, rosiglitazone and the like), an α-glycosidase inhibitor (e.g., voglibose, acarbose, miglitol, emiglitate and the like), a Biguamide (e.g., phenformin, metoformin, buformin and the like), or a sulfonylurea (e.g., tolbutamide, glibenclamid, gliclazide, chlorpropamide, tolazamide, acetohexamide, glyclopyramide, glimepiride and the like) as well as other insulin secretion-promoting agents (e.g., repaglinide, senaglinide, nateglinide, mitiglinide, GLP-1 and the like), amyrin agonist (e.g. pramlintide and the like), phosphotyrosinphosphatase inhibitor (e.g. vanadic acid and the like) and the like.

Examples of an agent for treating diabetic complications are an aldose reductase inhibitor (e.g., tolrestat, epalrestat, zenarestat, zopolrestat, minalrestat, fidareatat, SK-860, CT-112 and the like), a neurotrophic factor (e.g., NGF, NT-3, BDNF and the like), PKC inhibitor (e.g. LY-333531 and the like), AGE inhibitor (e.g. ALT946, pimagedine, pyradoxamine, phenacylthiazolium bromide (ALT766) and the like), an active oxygen quenching agent (e.g., thioctic acid and the like), a cerebrovascular dilating agent (e.g., tiapride, mexiletene and the like).

An antihyperlipemic agent may for example be a statin-based compound which is a cholesterol synthesis inhibitor (e.g., pravastatin, simvastatin, lovastatin, atorvastatin, fluvastatin, cerivastatin and the like), a squalene synthetase inhibitor or a fibrate compound having a triglyceride-lowering effect (e.g., bezafibrate, clofibrate, simfibrate, clinofibrate and the like) and the like.

A hypotensive agent may for example be an angiotensin converting enzyme inhibitor (e.g., captopril, enalapril, delapril and the like) or an angiotensin II antagonist (e.g., losartan, candesartan cilexetil, eprosartan, valsartan, telmisartan, irbesartan, tasosartan and the like) and the like.

An antiobesity agent may for example be a central antiobesity agent (e.g., dexfenfluramine, fenfluramine, phentermine, sibutramine, amfepramone, dexamphetamine, mazindol, phenylpropanolamine, clobenzorex and the like), a pancreatic lipase inhibitor (e.g., orlistat and the like), β3 agonist (e.g., CL-316243, SR-58611-A, UL-TG-307, SB-226552, AJ-9677, BMS-196085 and the like), a peptide-based appetite-suppressing agent (e.g., leptin, CNTF and the like), a cholecystokinin agonist (e.g., lintitript, FPL-15849 and the like) and the like.

A diuretic may for example be a xanthine derivative (e.g., theobromine sodium salicylate, theobromine calcium salicylate and the like), a thiazide formulation (e.g., ethiazide, cyclopenthiazide, trichloromethiazide, hydrochlorothiazide, hydroflumethiazide, bentylhydrochlorothiazide, penflutizide, polythiazide, methyclothiazide and the like), antialdosterone formulation (e.g., spironolactone, triamterene and the like), a decarboxylase inhibitor (e.g., acetazolamide and the like), a chlorbenzenesulfonamide formulation (e.g., chlorthalidone, mefruside, indapamide and the like), azosemide, isosorbide, ethacrynic acid, piretamide, bumetanide, furosemide and the like.

A chemotherapeutic agent may for example be an alkylating agent (e.g., cyclophosphamide, ifosfamide and the like), a metabolism antagonist (e.g., methotrexate, 5-fluorouracil and the like), an anticancer antibiotic (e.g., mitomycin, adriamycin and the like), a vegetable-derived anticancer agent (e.g., vincristine, vindesine, taxol and the like), cisplatin, carboplatin, etoposide and the like. Among these substances, 5-fluorouracil derivatives such as furtulon and neofurtulon are preferred.

An immunotherapeutic agent may for example be a microorganism or bacterial component (e.g., muramyl dipeptide derivative, picibanil and the like), a polysaccharide having immune potentiating activity (e.g., lentinan, sizofilan, krestin and the like), a cytokine obtained by a gene engineering technology (e.g., interferon, interleukin (IL) and the like), a colony stimulating factor (e.g., granulocyte colony stimulating factor, erythropoetin and the like) and the like, among these substances, those preferred are IL-1, IL-2, IL-12 and the like.

In addition, an agent whose cachexia improving effect has been established in an animal model or at a clinical stage, such as a cyclooxygenase inhibitor (e.g., indomethacin and the like) [Cancer Research, Vol.49, page 5935–5939, 1989], a progesterone derivative (e.g., megestrol acetate) [Journal of Clinical Oncology, Vol.12, page 213–225, 1994], a glucosteroid (e.g., dexamethasone and the like), a metoclopramide-based agent, a tetrahydrocannabinol-based agent (supra), a lipid metabolism improving agent (e.g., eicosapentanoic acid and the like) [British Journal of Cancer), Vol.68, page 314–318, 1993], a growth hormone, IGF-1, or an antibody against TNF-α, LIF, IL-6, oncostatin M which are cachexia-inducing factors may also be employed concomitantly with a compound according to the present invention.

The possible preferred combinations of the agents for the prevention and/or treatment of the diseases mentioned above are as follows;

(1) an insulin sensitivity enhancing agent, an insulin formulation and a Biguanide;
(2) an insulin sensitivity enhancing agent, a sulfonylurea agent and a Biguanide;
(3) an insulin sensitivity enhancing agent, a sulfonylurea agent and an α-glycosidase inhibitor;
(4) an insulin sensitivity enhancing agent, a Biguanide and an α-glycosidase inhibitor;
(5) an insulin sensitivity enhancing agent, a blood sugar reducing agent and the other kind of agents for treating diabetic complications; and
(6) an insulin sensitivity enhancing agent and any other two kinds of agents mentioned above.

In case that the compound or the composition of the present invention is used in combination with another agent, the amount of each additional agent can be reduced to a range which is safe in light of its adverse effect. Especially, an insulin sensitivity enhancing agent, a biguanide and a sulfonylurea agent can be used in lower dosage than the regular dose. So, adverse effects which may be caused by these agents can be safely avoided. In addition, an agent for treating diabetic complications, an antihyperlipemic agent and a hypotensive agent can also be used in lower dosages, so that adverse effects which may be caused by them can be avoided effectively.

(19) Production Methods

A method for preparing a compound according to the present invention is described below. Since Compounds (I-1) and (I-2) are included in Compound (II), a method for preparing Compound (II) is described below.

Compound (II) according to the present invention may be prepared by a method known per se, such as Method A and Method B shown below as well as analogous methods.

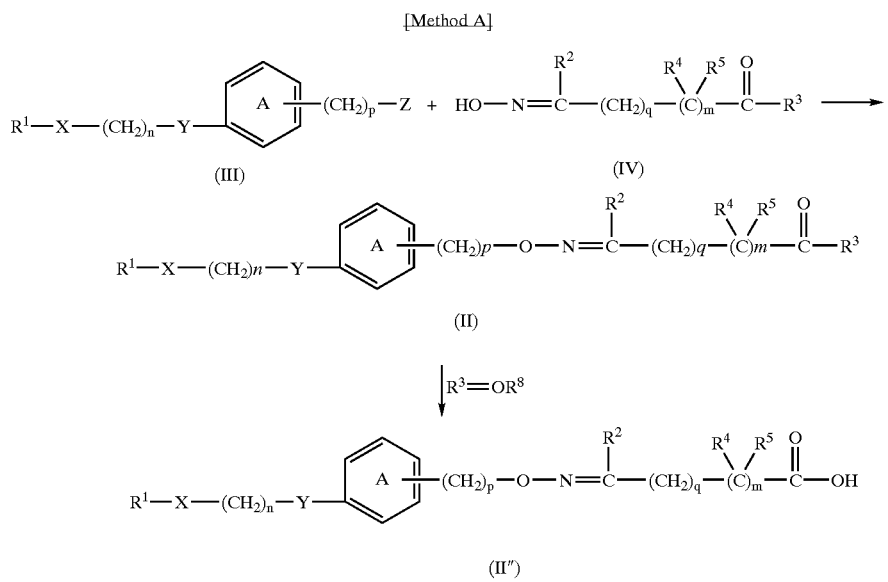

wherein Z is a hydroxyl group, a halogen atom or a group represented by $OSO_2R^{18}$ wherein $R^{18}$ is an alkyl group having 1 to 4 carbon atoms, an aryl group having 6 to 10 carbon atoms which may be substituted with an alkyl group having 1 to 4 carbon atoms, and other symbols are defined as described above.

In this scheme, an alkyl group having 1 to 4 carbon atoms in "an alkyl group having 1 to 4 carbon atoms" and "an aryl group having 6 to 10 carbon atoms which may be substituted with an alkyl group having 1 to 4 carbon atoms" represented by $R^{18}$ may for example be methyl, ethyl, propyl, isopropyl, butyl, isobutyl, sec-butyl, t-butyl, with methyl being preferred.

An aryl group having 6 to 10 carbon atoms in "an aryl group having 6 to 10 carbon atoms which may be substituted with an alkyl group having 1 to 4 carbon atoms" represented by $R^{18}$ may for example be phenyl, naphthyl, with phenyl being preferred.

In this method, Compound (III) is reacted with Compound (IV) to produce Compound (II).

When Z is hydroxy group, this reaction may be performed by a method known per se, for example, a method described in Synthesis, page 1 (1981) or analogous methods. Thus, this reaction is performed usually in the presence of an organic phosphorus compound or an electrophilic reagent in a solvent having no adverse effect on the reaction.

An organic phosphorus compound may for example be triphenylphosphine, tributylphosphine and the like.

An electrophilic reagent may for example be diethyl azodicarboxylate, diisopropyl azodicarboxylate, azodicarbonyldipiperazine and the like.

The amounts of an organic phosphorus compound and an electrophilic reagent to be employed were about 1 to about 5 molar equivalents to Compound (IV).

A solvent having no adverse effect on the reaction may for example be an ether such as diethyl ether, tetrahydrofuran, dioxane and the like; a halogenated hydrocarbon such as chloroform, dichloromethane and the like; an aromatic hydrocarbon such as benzene, toluene, xylene and the like; an amide such as N,N-dimethylformamide; a sulfoxide such as dimethyl sulfoxide and the like. These solvents may be employed as a mixture in an appropriate ratio.

The reaction temperature is usually about −50° C. to about 150° C., preferably about −10° C. to about 100° C.

The reaction time is about 0.5 to about 20 hours.

When Z is a halogen atom or a group represented by $OSO_2R^{18}$, this reaction is performed by a standard method in the presence of a base in a solvent having no adverse effect on the reaction.

A base may for example be an alkaline metal salt such as potassium hydroxide, sodium hydroxide, sodium hydrogen carbonate, sodium carbonate and the like; an amine such as pyridine, triethylamine, N,N-dimethylaniline, 1,8-diazabicyclo[5.4.0]undeca-7-en and the like; a metal hydride such as potassium hydride, sodium hydride and the like; an alkaline metal alkoxide such as sodium methoxide, sodium ethoxide, potassium t-butoxide and the like.

The amount of a base listed above is preferably about 1 to about 5 molar equivalents to Compound (IV).

A solvent having no adverse effect on the reaction may for example be an aromatic hydrocarbon such as benzene, toluene, xylene and the like; an ether such as tetrahydrofuran, dioxane and the like; a ketone such as acetone, 2-butanone and the like; a halogenated hydrocarbon such as chloroform, dichloromethane and the like; an amide such as N,N-dimethylformamide; a sulfoxide such as dimethylsulfoxide and the like. These solvents may be employed as a mixture in an appropriate ratio.

The reaction temperature is usually about −50° C. to about 150° C., preferably about −10° C. to about 100° C.

The reaction time is usually about 0.5 to about 20 hours.

Subsequently, Compound (II, $R^3=OR^8$) is hydrolyzed if necessary to produce Compound (II").

This hydrolyzation may be performed by a standard method, in the presence of an acid or a base, in a water-containing solvent.

An acid may for example be hydrochloric acid, sulfuric acid, acetic acid, hydrobromic acid and the like.

A base may for example be an alkaline metal carbonate such as potassium carbonate, sodium carbonate and the like; a metal alkoxide such as sodium methoxide and the like; an alkaline metal hydroxide such as potassium hydroxide, sodium hydroxide, lithium hydroxide and the like.

The amount of an acid or a base to be used is usually in excess relative to Compound (II). Preferably, the amount of an acid to be employed is about 2 to 50 equivalents to Compound (II), while the amount of a base to be employed is about 1.2 to about 5 equivalents to Compound (II).

A water-containing solvent may for example be a solvent mixture consisting of water and one or more solvents selected from the group consisting of an alcohol such as methanol, ethanol and the like; an ether such as tetrahydrofuran, dioxane and the like; dimethylsulfoxide and acetone and the like.

The reaction temperature is usually about −20° C. to about 150° C., preferably about −10° C. to about 100° C.

The reaction time is usually about 0.5 to about 20 hours.

Compound (II) and Compound (II") thus obtained may be isolated and purified by a known separation and purification procedure such as concentration, concentration under reduced pressure, extraction with solvent, crystallization, recrystallization, partition and chromatography and the like.

Compound (III) and Compound (IV) employed as starting materials in Method A described above are known compounds, and, for example, Compound (III) wherein Z is hydroxy group is described in EP-A 710659. Compound (III) is also described in EP-A 629624 (Japanese Patent Application Laid-Open No.7-53555), WO 98/03505 and the like. Compound (III) may also be prepared by a method analogous to those described in these publications.

Compound (IV) is described for example in Journal fur Praktische Chemie, Vol.311, page 370 (1969); Canadian Journal of Chemistry, Vol.48, page 1948 (1970); Journal of Heterocyclic Chemistry, Vol.25, page 1283 (1988) and the like. Compound (IV) may also be prepared by a method analogous to those described in these publications.

Among Compound (II), a compound wherein $R^2$ is phenyl substituted by an aliphatic hydrocarbon group and the like may be prepared also by Method B shown below.

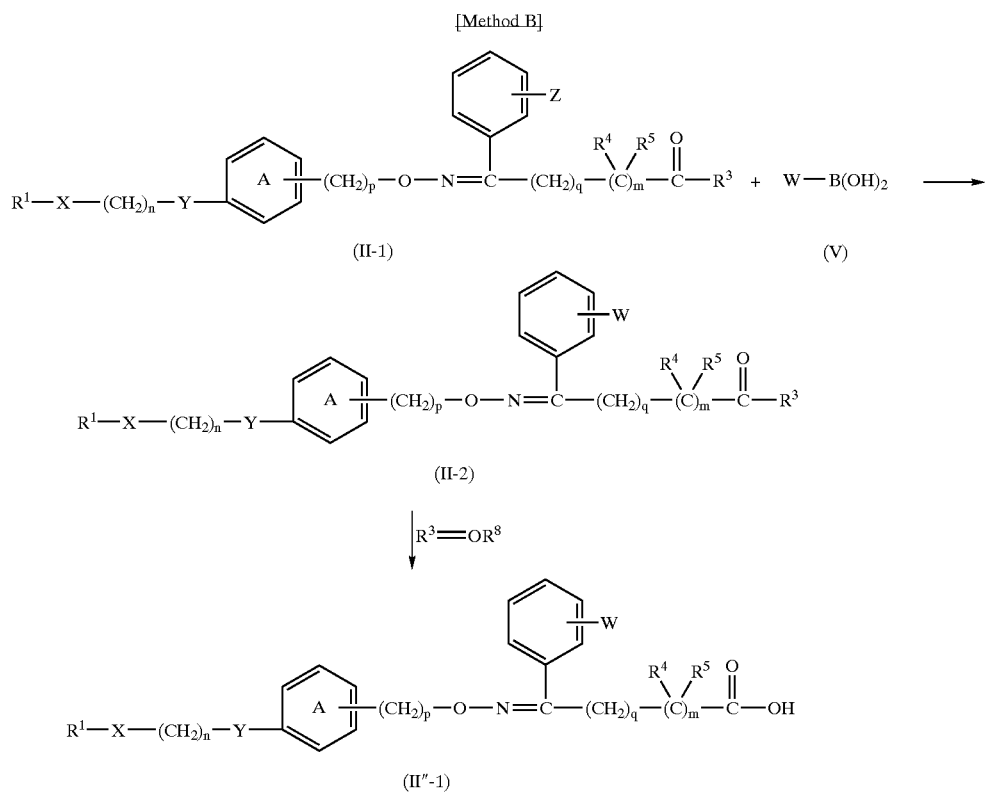

[Method B]

wherein W is an aliphatic hydrocarbon group, each optionally substituted aromatic hydrocarbon or aromatic heterocyclic group, and other symbols are defined as described above.

"An aliphatic hydrocarbon group" represented by W may be an aliphatic hydrocarbon group exemplified as a substituent in a hydrocarbon group and a heterocyclic group represented by $R^1$.

Each of an aromatic hydrocarbon group and an aromatic heterocyclic group in "an optionally substituted aromatic hydrocarbon or aromatic heterocyclic group" represented by W may be an aromatic hydrocarbon group and an aromatic heterocyclic group each exemplified as a substituent on a hydrocarbon group and a heterocyclic group represented by $R^1$. A substituent on the aromatic hydrocarbon group and aromatic heterocyclic group may be a substituent exemplified as a substituent when a substituent on a hydrocarbon group and a heterocyclic group represented by $R^1$ is an alicyclic hydrocarbon group, an aromatic hydrocarbon group, an aromatic heterocyclic group or a non-aromatic heterocyclic group.

In this method, Compound (II-1) is reacted with boronic acid compound (V) to produce Compound (II-2).

This reaction is performed by a method known per se such as a method described in Journal of Organic Chemistry, Vol.58, page 2201 (1993) or in Journal of Organic Chemistry, Vol.60, page 1060 (1995), in the presence of a metal catalyst and a base, in a solvent having no adverse effect on the reaction.

A metal catalyst may for example be a palladium metal, a nickel metal and the like. A palladium metal catalyst may for example be tris(dibenzylideneacetone)dipalladium, tetrakis(triphenylphosphine)palladium and the like, and a nickel metal catalyst may for example be 1,1'-bis(diphenylphosphino)ferrocene nickel and the like.

A base may for example be an alkaline metal bicarbonate such as sodium bicarbonate; an alkaline metal carbonate such as sodium carbonate, potassium carbonate; an alkaline metal phosphate such as tripotassium phosphate and the like.

The amount of a metal catalyst to be used is about 0.01 to about 1 molar equivalents, preferably about 0.05 to about 0.5 molar equivalents to Compound (II-1).

The amount of a base to be used is about 1 to about 20 molar equivalents, preferably about a to about 10 molar equivalents to Compound (II-1).

A solvent having no adverse effect on the reaction may for example be an aromatic hydrocarbon such as benzene, toluene and the like; an alcohol such as methanol, ethanol and the like; an ether such as tetrahydrofuran, dioxane and the like; water and the like. These solvents may be used in a mixture in an appropriate ratio. The types of the solvents may appropriately be selected depending on the types of the metal catalysts.

The amount of boric acid compound (V) employed is about 1 to about 7 molar equivalents, preferably about 1 to about 5 molar equivalents to Compound (II-1).

The reaction temperature is usually about −20° C. to about 150° C., preferably about 0° C. to about 100° C.

The reaction time is about 0.1 to about 24 hours.

Subsequently, Compound (II-2, $R^3=OR^8$) is hydrolyzed if desired to produce Compound (II"-1).

This hydrolyzation may be performed similarly to the hydrolyzation in Method A.

Compound (II-2) and (II"-1) thus obtained may be isolated and purified by a known separation and purification procedure such as concentration, concentration under reduced pressure, extraction with solvent, crystallization, recrystallization, partition and chromatography and the like.

Compound (II-1) employed as a starting material in Method B described above may for example be produced by Method A described above. Compound (V) is a known compound described in Organic Synthesis, Vol.39, page 3 (1959); Journal of American Chemical Society, Vol.94, page 4370 (1972) and the like. Compound (V) may be prepared also by a method analogous to those described in these publications.

Compound (II) may be produced by [Method C] or [Method D] described below.

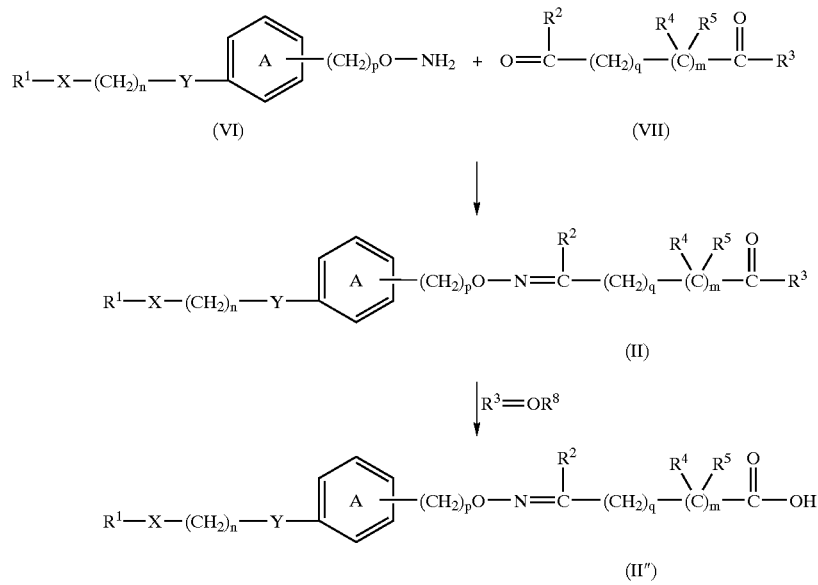

In this method, the reaction between Compound (VI) and Compound (VII) results in Compound (II). This reaction may be performed by a method known per se. Thus, this reaction may be performed in the presence of an acid or a base in a solvent having no effects on the reaction. Such acid includes hydrochloric acid, sulfuric acid, p-toluenesulfonic acid and the like. Such base includes sodium carbonate, potassium carbonate, sodium acetate, (aqueous) ammonia and the like. The amount of an acid or a base to be used is usually about 1 to 10 molar equivalents to Compound (VI).

A solvent having no effects on the reaction includes ethers such as tetrahydrofuran, dioxane and the like, alcohols such as methanol, ethanol and the like, as well as dimethylsulfoxide, acetic acid, water and the like. Any of these solvents may be used in combination with each other at an appropriate ratio. The reaction temperature is usually about −50° C. to about 150° C., preferably about −10° C. to about 120° C.

Subsequently, if desired, Compound (II) may be hydrolyzed to form Compound (II″). This reaction may be performed similarly to the hydrolyzation in Method A.

Compound (II) and Compound (II″) thus obtained may be isolated and purified by a known isolation and purification method such as concentration, concentration under reduced pressure, extraction with a solvent, crystallization, recrystallization, partition, chromatography and the like.

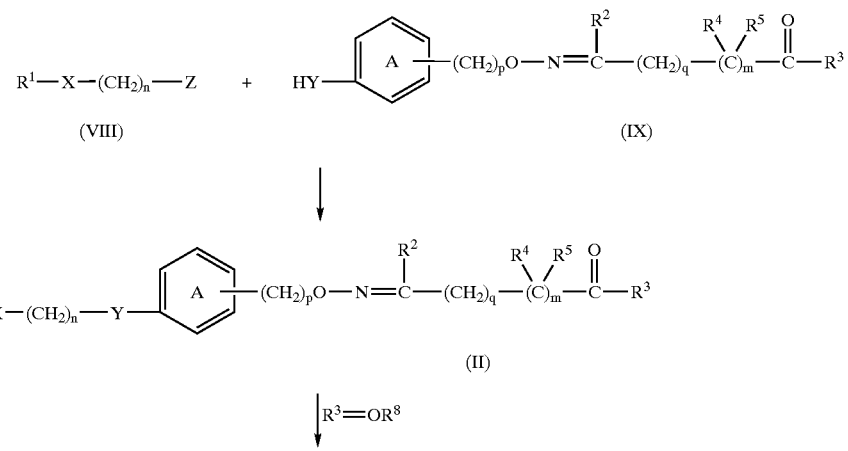

-continued

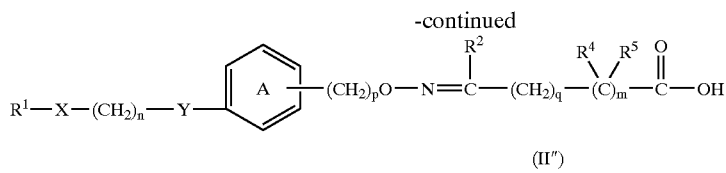

(II″)

In this method, the reaction between Compound (VIII) and Compound (IX) results in Compound (II). This reaction may be performed similarly to the reaction between Compound (III) and Compound (IV) in Method A.

Subsequently, if desired, Compound (II) may be hydrolyzed to form Compound (II″). This reaction may be performed similarly to the hydrolyzation in Method A.

Compound (II) and Compound (II″) thus obtained may be isolated and purified by a known isolation and purification method such as concentration, concentration under reduced pressure, extraction with a solvent, crystallization, recrystallization, partition, chromatography and the like.

A compound wherein $R^3$ is $NR^9R^{10}$ in Compound (II) may be produced by Method E shown below.

[Method E]

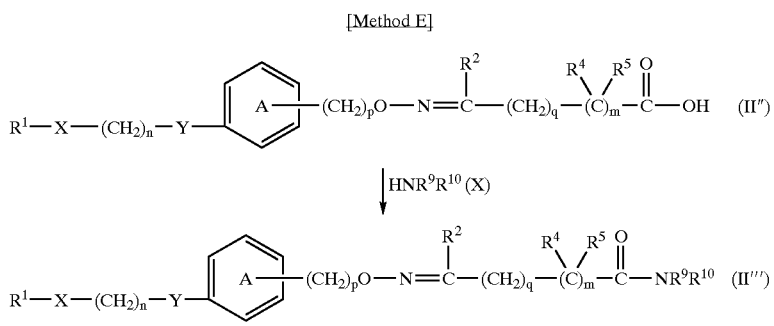

In this method, Compound (II″) is amidated to produce Compound (II‴). This reaction may be performed by a method known per se, i.e. a direct condensation between Compound (II″) and Compound (X) using a condensation reagent (e.g., dicyclohexylcarbodiimide), or may be performed by an appropriate reaction of a reactive derivative of Compound (II″) with Compound (X). In such reaction, a reactive derivative of Compound (II″) includes an acid anhydride, an acid halide (acid chloride, acid bromide), imdazolide, or a mixed acid anhydride (e.g., anhydride with methyl carbonate, ethyl carbonate, isobutyl carbonate, and the like) and the like. For example, when an acid halide is employed, the reaction may be performed in the presence of a base, in a solvent having no effects on the reaction. Such base may for example be triethylamine, N-methylmorpholine, N,N-dimethylaniline, sodium bicarbonate, sodium carbonate, potassium carbonate and the like. Such solvent having no effects on the reaction includes a halogenated hydrocarbon such as chloroform and dichloromethane; an aromatic hydrocarbon such as benzene and toluene; an ether such as tetrahydrofuran and dioxane as well as ethyl acetate and water. Any of these solvents may be used in combination with each other at an appropriate ratio. The amount of Compound (X) to be used is about 1 to 10 molar equivalents to Compound (II″), preferably about 1 to 3 molar equivalents. The reaction temperature is usually about −30° C. to about 100° C., and the reaction time ranges from about 0.5 to 20 hours. When a mixed acid anhydride is employed, Compound (II″) is reacted with chlorocarbonic ester (e.g., methyl chlorocarbonate, ethyl chlorocarbonate, isobutyl chlorocarbonate) in the presence of a base (e.g., triethylamine, N-methylmorpholine, N,N-dimethylaniline, sodium bicarbonate, sodium carbonate, potassium carbonate) and further reacted with Compound (X). The amount of Compound (X) to be used is about 1 to 10 molar equivalents to Compound (II″), preferably about 1 to 3 molar equivalents. The reaction temperature is usually about −30° C. to about 100° C., and the reaction time ranges from about 0.5 to 20 hours.

Compound (II‴) thus obtained may be isolated and purified by a known isolation and purification method such as concentration, concentration under reduced pressure, extraction with a solvent, crystallization, recrystallization, partition, chromatography and the like.

Compound (VI) used as a starting material in Method C may be produced by a method known per se, such as a method described in Journal of Organic Chemistry, Vol.36, page 3836 (1971) or a method analogous thereto.

Compound (IX) used as a starting material in Method D may be produced by Method F shown below.

[Method F]

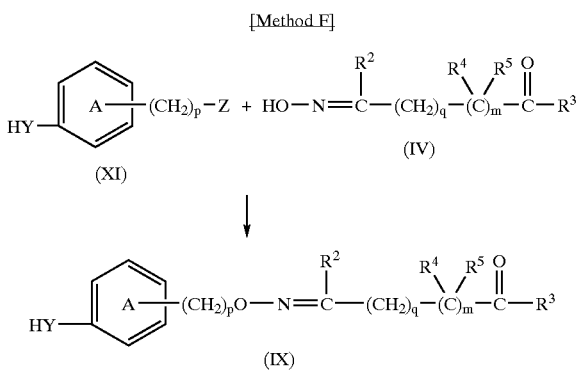

This method is performed similarly to the reaction between Compound (III) and Compound (IV) in Method A. The —YH moiety in Compound (XI) may be protected prior to the condensation reaction and then deprotected after the reaction. A protective group which may be employed are benzyl group, methoxymethyl group, a silyl group (e.g., trimethylsilyl group, t-butyldimethylsilyl group) and the like.

BEST MODE FOR CARRYING OUT THE INVENTION

The present invention is further detailed in the following Experiments, Reference Examples, Examples and Formulation Examples, which are not intended to restrict the present invention. In the following Reference Examples and Examples, a % is a % by weight unless otherwise specified.

The gene engineering procedure described in Reference Examples is in accordance with a method described in MOLECULAR CLONING (Maniatis et al., Cold Spring Harbor Laboratory), (1989)] or in an attached protocol of a reagent.

Experiments (Hypoglycemic and Hypolipidemic Actions in Mice)

A test compound was added to a powdered diet (CE-2, Clea Japan Inc.) at a concentration of 0.01%, and the diet was given ad libitum to KKA$^y$ mice (9 to 12 weeks old, 5 animals in a group), a model of obese Type II diabetes mellitus (non-insulin dependent diabetes mellitus), for 4 days. During this period, water was given ad libitum. Blood was sampled from orbital venous plexus and plasma glucose and triglyceride levels were determined enzymatically using L type Wako Glu2 (Wako Pure Chemical In. Ltd.) and Iatro-MA701 TG kit (Iatron Laboratories Inc.) or L type Wako TG.H (Wako Pure Chemical Ind. Ltd.), respectively.

The value of each treatment group is represented as % reduction when compared with the non-treatment group, and summarized in Table 1.

TABLE 1

| Compound (Example number) | Hypoglycemic effect (% reduction) | Hypotriglyceridemic effect (% reduction) |
| --- | --- | --- |
| 1 | 36 | 35 |
| 7 | 42 | 61 |
| 10 | 36 | 45 |
| 11 | 49 | 82 |
| 17 | 49 | 59 1) |
| 25 | 38 | 66 |
| 81 | 54 | 75 1) |
| 106 | 46 2) | 65 1), 2) |

1) quantified using L-type Wako TG.H
2) dosage: 0.005%

As evident from the results, a compound according to the present invention has excellent hypoglycemic effect and hypotriglyceridemic effect, and is useful for the prevention and treatment of diabetes mellitus and hyperlipidemia.

Experiment (PPARγ-RXRα Heterodimer Transactivation Assay)

A PPARγ: RXRα: 4ERPP/CHO-K1 cell obtained in Reference Example 5 described below was cultured in HAM F12 medium (NISSUI SEIYAKU) containing 10% Fetal Bovine serum (Life Technologies, Inc., USA) and then inoculated to a 96-wel white plate (Corning Coaster Corporation, USA) at the density of 2×10$^4$ cells/well, and cultured in a carbonate gas incubator at 37° C. overnight.

After washing a 96-well white plate with PBS (Phosphate-buffered saline), 90 μl of HAM F12 medium containing 0.1% fatty acid-free bovine serum albumin (BSA) and 10 μl of a test substance were added to the plate, which was then cultured in a carbonate gas incubator at 37° C. for 48 hours. After removing the medium, 40 μl of PICAGENE 7.5 (Wako Pure Chemical Ind. Ltd.) was added, and after stirring, a luciferase activity was determined using Lumistar (BMG Labtechnologies GmBH, Germany).

An induction magnitude was calculated based on the luciferase activity of each test substance with the luciferase activity in the non-treatment group being regarded as 1. The values of the test substance concentration and the induction magnitude were analyzed using PRISM 2.01 (GraphPad Software Inc., USA) to calculate the EC$_{50}$ effective concentration of a compound for the induction of the 50% of the maximum activity. The results are shown in Table 2.

TABLE 2

| Compound (Example Number) | EC$_{50}$ (μM) |
| --- | --- |
| 7 | 0.024 |
| 11 | 0.41 |
| 17 | 0.047 |
| 25 | 0.79 |
| 81 | 0.26 |
| 106 | 0.33 |

As indicated above, a compound according to the present invention exhibited an excellent PPARγ-RXRα heterodimer ligand activity.

EXAMPLES

Reference Example 1

Human PPARγ Gene Cloning

A human PPARγ gene was cloned using a heart cDNA (Toyobo Co., Ltd., trade name: QUICK-clone cDNA) as a template by means of a PCR method employing a primer set shown below which was prepared with referring to the DNA sequence of PPARγ gene reported by Greene et al (Gene Expr., 1995, Vol.4(4–5), page 281–299).

```
                                              (SEQ ID NO:1)
PAG-U: 5'-gtgggtaccg aaatgaccat ggttgacaca gag-3'

(SEQ ID NO:2)
PAG-L: 5'-ggggtcgacc aggactctct gctagtacaa gtc-3'
```

The PCR procedure was performed by a hot start method using AmpliWax PCR Gem 100 (TAKARA SHUZO CO., LTD.). First, 2 μl of 10×LA PCR Buffer, 3 μl of 2.5 mM dNTP solution, 2.5 μl of each 12.5 μM primer solution and 10 μl of sterilized distilled water were mixed to obtain a bottom layer solution mixture. 1 μl of Human heart cDNA (1 ng/ml) as a template, 3 μl of 10×LA PCR Buffer, 1 μl of 2.5 mM dNTP solution, 0.5 μl of TaKaRa LA Taq DNA polymerase (TAKARA SHUZO CO., LTD.) and 24.5 μl of sterilized distilled water were mixed to obtain a top layer solution mixture.

The bottom solution mixture received one unit of AmpliWax PCR Gem 100 (TAKARA SHUZO CO., LTD.), and was treated at 70° C. for 5 minutes and then in ice for 5 minutes, and then the top layer solution mixture was added to prepare the reaction mixture of PCR. A tube containing the reaction mixture was set on a thermal cycler (Perkin Elmer, USA) and treated at 95° C. for 2 minutes. After repeating the cycle of 95° C. for 15 seconds followed by 68° C. for 2 minutes further 35 times, then the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (TAKARA SHUZO CO., LTD.) to obtain a plasmid designated as pTBT-hPPARγ.

Reference Example 2

Human RXRα Gene Cloning

A human RXRα gene was cloned using a kidney cDNA (Toyobo Co., Ltd., trade name: QUICK-clone cDNA) as a template by means of a PCR method employing a primer set shown below which was prepared with referring to the DNA sequence of RXRα gene reported by Mangelsdorf, D. J. et al (Nature, 1990, Vol. 345 (6272), page 224–229).

```
                                              (SEQ ID NO:3)
XRA-U: 5'-ttagaattcg acatggacac caaacatttc ctg-3'

(SEQ ID NO:4)
XRA-L: 5'-cccctcgagc taagtcattt ggtgcggcgc ctc-3'
```

The PCR procedure was performed by a hot start method using AmpliWax PCR Gem 100 (TAKARA SHUZO CO., LTD.). First, 2 μl of 10×LA PCR Buffer, 3 μl of 2.5 mM dNTP solution, 2.5 μl of each 12.5 μM primer solution and 10 μl of sterilized distilled water were mixed to obtain a bottom layer solution mixture. 1 μl of Human kidney cDNA (1 ng/ml) as a template, 3 μl of 10×LA PCR Buffer, 1 μl of 2.5 mM dNTP solution, 0.5 μl of TaKaRa LA Taq DNA polymerase (TAKARA SHUZO CO., LTD.) and 24.5 μl of sterilized distilled water were mixed to obtain a top layer solution mixture.

The bottom solution mixture received one unit of AmpliWax PCR Gem 100 (TAKARA SHUZO CO., LTD.), and was treated at 70° C. for 5 minutes and then in ice for 5 minutes, and then the top layer solution mixture was added to prepare the reaction mixture of PCR. A tube containing the reaction mixture was set on a thermal cycler (Perkin Elmer, USA) and treated at 95° C. for 2 minutes. After repeating the cycle of 95° C. for 15 seconds followed by 68° C. for 2 minutes further 35 times, then the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (TAKARA SHUZO CO., LTD.) to obtain a plasmid designated as pTBT-hRXRα.

Reference Example 3

Construction of Plasmids for Expressing Human PPARγ, RXRα

A 7.8 kb FspI-NotI fragment of plasmid pVgRXR (Invitrogen, USA) was ligated to a 0.9 kb FspI-NotI fragment containing RXRα gene of plasmid pTBT-hRXRα obtained in Reference Example 2 to prepare plasmid pVgRXR$^2$. Subsequently, pVgRXR$^2$ was digested with BstXI and then treated with T4DNA polymerase (TAKARA SHUZO CO., LTD.) to obtain a blunt end. Then digestion at KpnI gave a 6.5 kb DNA fragment.

On the other hand, plasmid pTBT-hPPARγ obtained in Reference Example 1 was digested with Sal I and then treated with T4DNA polymerase (TAKARA SHUZO CO., LTD.) to obtain a blunt terminal. Then digestion at KpnI gave a 1.4 kb DNA fragment containing human PPARγ gene.

Then both DNA fragments were ligated to construct plasmid pVgRXR2-hPPARγ.

Reference Example 4

Construction of Reporter Plasmid

A DNA fragment containing PPAR-responding element (PPRE) of an acyl CoA oxidase was prepared using the following 5'-terminal phosphorylated synthetic DNA.

```
PPRE-U:                                       (SEQ ID NO:5)
5'-p tcgacagggg accaggacaa aggtcacgtt cgggag-3'

PPRE-L:                                       (SEQ ID NO:6)
5'-p tcgactcccg aacgtgacct ttgtcctggt ccsctg-3'
```

First, PPRE-U and PPRE-L were annealed and inserted to Sal I site of plasmid pBluescript SK$^+$. Upon sequencing the bases of the inserted fragment, plasmid pBSS-PPRE4 in which 4 PPREs were ligated in tandem was selected.

A HSV thymidine kinase minimum promoter (TK promoter) region was cloned using pRL-TK vector (Promega, USA) as a template by means of a PCR method employing a primer set shown below which was prepared with referring to the DNA sequence of the promoter region of thymidine kinase reported by Luckow, B et al (Nucleic Acid Res., 1987, Vol.15(13), p.5490).

```
                                              (SEQ ID NO:7)
TK-U:     5'-cccagatctc cccagcgtct tgtcattg-3'

(SEQ ID NO:8)
TK-L:     5'-tcaccatggt caagcttta agcgggtc-3'
```

The PCR procedure was performed by a hot start method using AmpliWax PCR Gem 100 (TAKARA SHUZO CO., LTD.). First, 2 μl of 10×LA PCR Buffer, 3 μl of 2.5 mM dNTP solution, 2.5 μl of each 12.5 μM primer solution and 10 μl of sterilized distilled water were mixed to obtain a bottom layer solution mixture. 1 μl of pRL-TK vector (Promega, USA) as a template, 3 μl of 10×LA PCR Buffer, 1 μl of 2.5 mM dNTP solution, 0.5 μl of TaKaRa LA Taq DNA polymerase (TAKARA SHUZO CO., LTD.) and 24.5 μl of sterilized distilled water were mixed to obtain a top layer solution mixture.

The bottom solution mixture received one unit of AmpliWax PCR Gem 100 (TAKARA SHUZO CO., LTD.), and was treated at 70° C. for 5 minutes and then in ice for 5 minutes, and then the top layer solution mixture was added to prepare the reaction mixture of PCR. A tube containing the reaction mixture was set on a thermal cycler (Perkin Elmer, USA) and treated at 95° C. for 2 minutes. After repeating the cycle of 95° C. for 15 seconds followed by 68° C. for 2 minutes further 35 times, then the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (TAKARA SHUZO CO., LTD.). By digesting the plasmid thus obtained with the restriction enzymes Bgl II and NcoI, a fragment containing TK promoter was obtained and ligated to the Bgl II-NcoI fragment of plasmid pGL3-Basic vector (Promega, USA) to obtain plasmid pGL3-TK.

A 4.9 kb NheI-XhoI fragment of plasmid pGL3-TK thus obtained was ligated to a 200 NheI-XhoI fragment of plasmid pBSS-PPRE4 to obtain plasmid pGL3-4ERPP-TK.

This plasmid pGL3-4ERPP-TK thus obtained was digested with BamHI (TAKARA SHUZO CO., LTD.) and then treated with T4DNA polymerase (TAKARA SHUZO CO., LTD.) to form a blunt terminal, whereby obtaining a DNA fragment.

On the other hand, pGFP-C1 (Toyobo Co., Ltd.) was digested with Bsu36I (NEB) and then treated with T4DNA polymerase (TAKARA SHUZO CO., LTD.) to form a blunt terminal, whereby obtaining a 1.6 kb DNA fragment.

The both DNA fragments were ligated to construct a reporter plasmid designated as pGL3-4ERPP-TK neo.

Reference Examples 5

Introduction of Human PPARγ- and RXRα-expressing Plasmid and Reporter Plasmid into CHO-K1 Cell and Establishment of Stably-transformed Cell)

A CHO-K1 cell cultured in a 750 ml tissue culture flask (Corning Costar Corporation, USA) containing HAM F12 medium (NISSUI SEIYAKU) supplemented with 10% Fetal Bovine Serum (Life Technologies, Inc., USA) was scraped by treating 0.5 g/L trypsin-0.2 g/L EDTA (ethylenediamine tetraacetic acid) (Life Technologies, Inc., USA) and the cell was washed with PBS (phosphate-buffered saline) (Life Technologies, Inc., USA) and centrifuged (1000 rpm, 5 minutes) and then suspended in PBS. Subsequently, a DNA was introduced into the cell under the condition shown below using GENE PULSER (Bio-Rad Laboratories, USA).

Thus, a cuvette having an 0.4 cm gap received $8 \times 10^6$ cells and 10 μg of plasmid pVgRXR2-hPPARγ obtained in Reference Example 3 and 10 μg of reporter plasmid pGL3-4ERPP-TK neo obtained in Reference Example 4 and then subjected to electroporation at the voltage of 0.25 kV under the capacitance of 960 μF. Subsequently, the cells were transferred into a HAM F12 medium containing 10% Fetal Bovine Serum and cultured for 24 hours and then the cells were scraped again and centrifuged, and then suspended in HAM F12 medium containing 10% Fetal Bovine Serum supplemented with 500 μg/ml of GENETICIN (Life Technologies, Inc., USA) and 250 μg of ZEOCIN (Invitrogen, USA) and diluted to the density of $10^4$ cells/ml upon inoculation to a 96-well plate (Corning Coster Corporation, USA), which was cultured in a carbonate gas incubator at 37° C., whereby obtaining a GENETICIN- and ZEOCIN-resistant transformant.

Subsequently, the transformant cell line thus obtained was cultured in a 24-well plate (Corning Coster Corporation, USA) and then screened, by addition of 10 μM Pioglitazone, for a cell line in which the luciferase expression was induced, i.e., PPARγ: RXRα: 4ERPP/CHO-K1 cell.

Reference Example 6

To a solution of 4-(5-methyl-2-phenyl-4-oxazolylmethoxy)benzaldehyde (33.42 g) in methanol (150 ml)-tetrahydrofuran (30 ml), sodium borohydride (4.31 g) was added in portions at 0° C. After stirring for 30 minutes at room temperature, water was added to the reaction mixture and the mixture was stirred for 1 hour. The crystals of 4-(5-methyl-2-phenyl-4-oxazolylmethoxy)benzylalcohol (32.85 g, yield 98%) was were isolated by filtration. Recrystallization from ethyl acetate-diethylether gave pale yellow crystals. m.p. 128–129° C.

Reference Example 7

To a solution of 4-(5-methyl-2-phenyl-4-oxazolylmethoxy)benzylalcohol (5.00 g) in toluene (40 ml), thionyl chloride (1.85 ml) was added and the mixture was stirred for 30 minutes at room temperature. Ice water was added to the reaction mixture, and the mixture was extracted with ethyl acetate. The ethyl acetate layer was washed with water, dried (MgSO$_4$) and concentrated to obtain 4-(4-chloromethylphenoxymethyl)-5-methyl-2-phenyloxazole (5.23 g, yield 99%) as crystals. Recrystallization from ethyl acetate-hexane gave colorless crystals. m.p. 108–109° C.

Reference Example 8

To a solution of 4-[2-(methyl-2-pyridylamino)ethoxy]benzaldehyde (15.0 g) in methanol (70 ml), sodium borohydride (1.11 g) was added at 0° C. In portions. After stirring for 30 minutes, water was added to the reaction mixture, and the mixture was extracted with ethyl acetate. The ethyl acetate layer was washed with saturated aqueous sodium chloride, dried (MgSO$_4$), and then concentrated. The residue was subjected to column chromatography on silica gel, and 4-[2-(methyl-2-pyridylamino)ethoxy]benzylalcohol (14.3 g, yield 94%) was obtained from a fraction eluted with ethyl acetate-hexane (1:1, v/v) as an oil.

NMR (CDCl$_3$) δ: 3.15 (3H, s), 3.98 (2H, t, J=5.5 Hz), 4.19 (2H, t, J=5.5 Hz), 4.61 (2H, d, J=5.4 Hz), 6.50–6.59 (2H, m), 6.89 (2H, d, J=8.8 Hz), 7.27 (2H, d, J=8.8 Hz), 7.40–7.50 (1H, m), 8.13–8.18 (2H, m).

Reference Example 9

A mixture of 4-chloromethyl-5-methyl-2-phenyloxazole (3.41 g), 3-(4-hydroxyphenyl)propanol (2.50 g), potassium carbonate (3.40 g) and N,N-dimethylformamide (25 ml) was stirred for 14 hours at 60° C. Water was added to the reaction mixture, and the mixture was extracted with ethyl acetate. The ethyl acetate layer was washed with saturated aqueous sodium chloride, dried (MgSO$_4$), and then concentrated. The residue was subjected to column chromatography on silica gel, and 3-[4-(5-methyl-2-phenyl-4-oxazolylmethoxy)phenyl]propanol (4.46 g, yield 84%) was obtained from a fraction eluted with ethyl acetate-hexane (1:1, v/v) as crystals. Recrystallization from ethyl acetate-hexane gave colorless crystals. m.p. 70–71° C.

Reference Example 10

A mixture of methyl phenylglyoxylate (25.5 g), hydroxylamine hydrochloride (11.3 g), triethylamine (22.8 ml) and methanol (300 ml) was stirred for 17 hours at 60° C. The reaction mixture was concentrated, and the residue was diluted with water and extracted with ethyl acetate. The ethyl acetate layer was washed with water, (MgSO$_4$), and then concentrated. The residual crystals were recrystallized from ethyl acetate-hexane to obtain methyl E-2-hydroxyimino-2-phenylacetate (3.58 g, yield 13%) as colorless crystals. m.p. 151–153° C.

Reference Example 11

The mother liquid obtained in Reference Example 10 was concentrated and the residue was subjected to column chromatography on silica gel, and methyl Z-2-hydroxyimino-2-phenylacetate (17.8 g, yield 64%) was obtained as an oil from a fraction eluted with ethyl acetate-hexane (1:3, v/v).

NMR (CDCl$_3$) δ: 3.89 (3H, s), 7.34–7.48 (3H, m), 7.52–7.60 (2H, m), 8.51 (1H, m).

Reference Example 12

To a mixture of aluminum chloride (59.0 g) and dichloromethane (500 ml), ethyl chloroglyoxylate (45.4 ml) was added dropwise at 0° C. After stirring for 15 minutes, anisole (40.1 ml) was added dropwise at 0° C., and the mixture was stirred for 1.5 hours at room temperature. The reaction mixture was poured onto ice (500 g), and the mixture was stirred for 1 hour at room temperature The dichloromethane layer separated was washed with saturated aqueous sodium chloride, dried (MgSO$_4$), and then concentrated. The residue was subjected to column chromatography on silica gel, and ethyl 4-methoxyphenylglyoxylate (43.6 g, yield 60%) was obtained as an oil from a fraction eluted with ethyl acetate-hexane (1:4, v/v).

NMR (CDCl$_3$) δ: 1.42 (3H, t, J=7.1 Hz), 3.90 (3H, s), 4.44 (2H, q, J=7.1 Hz), 6.98 (2H, d, J=9.0 Hz), 8.01 (2H, d, J=9.0 Hz).

Reference Example 13

A mixture of ethyl 4-methoxyphenylglyoxylate (15.0 g), hydroxylamine hydrochloride (6.00 g), sodium acetate (8.86 g) and ethanol (150 ml) was heated under reflux for 12 hours. The reaction mixture was concentrated, and the residue was diluted with water and extracted with ethyl acetate. The ethyl acetate layer was washed with water, dried (MgSO$_4$), and then concentrated. The residue was subjected to column chromatography on silica gel and ethyl Z-2-hydroxyimino-2-(4-methoxyphenyl)acetate (8.99 g, yield 56%) was obtained as crystals from a fraction eluted with ethyl acetate-hexane (1:2, v/v). Recrystallization from ethyl acetate-hexane gave colorless crystals. m.p. 81–82° C.

Reference Example 14

From a fraction eluted following the Z-form in Reference Example 13, ethyl E-2-hydroxyimino-2-(4-methoxyphenyl) acetate (4.97 g, yield 31%) was obtained as crystals. Recrystallization from ethyl acetate-hexane gave colorless crystals. m.p. 128–129° C.

Reference Example 15

A mixture of ethyl pyruvate (9.50 g), hydroxylamine hydrochloride (6.82 g), sodium acetate (10.1 g) and ethanol (150 ml) was heated under reflux for 17 hours. The reaction mixture was concentrated, and the residue was diluted with water and extracted with ethyl acetate. The ethyl acetate layer was washed with water, dried (MgSO$_4$), and then concentrated. The residual crystals were recrystallized from ethyl acetate-hexane to obtain ethyl E-2-hydroxyiminopropionate (6.33 g, yield 59%) as colorless crystals. m.p. 98–99° C.

Reference Example 16

A mixture of methyl 3-benzoylpropionate (15.0 g), hydroxylamine hydrochloride (6.50 g), sodium acetate (9.60 g) and methanol (150 ml) was heated under reflux for 8 hours. The reaction mixture was concentrated, and the residue was diluted with water and extracted with ethyl acetate. The ethyl acetate layer was washed with water, dried (MgSO$_4$), and then concentrated. The residue was subjected to column chromatography on silica gel, and methyl E-4-hydroxyimino-4-phenylbutyrate (14.7 g, yield 91%) was obtained as an oil from a fraction eluted with ethyl acetate-hexane (1:3, v/v).

NMR (CDCl$_3$) δ: 2.58–2.67 (2H, m), 3.09–3.17 (2H, m), 3.66 (3H, s), 7.35–7.44 (3H, m), 7.56–7.67 (2H, m), 8.00–8.80 (1H, br s).

Reference Example 17

From a fraction eluted following the E-form in Reference Example 16, methyl Z-4-hydroxyimino-4-phenylbutyrate (1.37 g, yield 8%) was obtained as crystals. Recrystallization from ethyl acetate-hexane gave colorless crystals. m.p. 76–77° C.

Reference Example 18

A mixture of ethyl 5-oxo-5-phenylpentanoate (8.00 g), hydroxylamine hydrochloride (3.03 g), sodium acetate (4.47 g) and ethanol (70 ml) was heated under reflux for 15 hours. The reaction mixture was concentrated, and the residue was diluted with water and extracted with ethyl acetate. The ethyl acetate layer was washed with water, dried (MgSO$_4$), and then concentrated. The residue was subjected to column chromatography on silica gel, and ethyl E-5-hydroxyimino-5-phenylpentanoate (7.55 g, yield 88%) was obtained as crystals from a fraction eluted with ethyl acetate-hexane (1:3, v/v). Recrystallization from hexane gave colorless crystals. m.p. 28–30° C.

Reference Example 19

To a solution of diethyl oxalate (26.3 g) in diethyl ether (400 ml), a solution of butylmagnesium chloride in tetrahydrofuran (0.90 M, 100 ml) was added dropwise at −78° C. under a nitrogen atmosphere. After stirring for 1 hour, the reaction mixture was allowed to warm to 0° C., and then 1N hydrochloric acid was added. The diethyl ether layer was separated, washed with aqueous sodium bicarbonate and then with saturated aqueous sodium chloride, dried (MgSO$_4$), and concentrated. The residue was dissolved in ethanol (150 ml), and hydroxylamine hydrochloride (7.50 g) and sodium acetate (11.1 g) were added. The mixture was heated under reflux for 13 hours. The reaction mixture was concentrated, and the residue was diluted with water and extracted with ethyl acetate. The ethyl acetate layer was washed with water, dried (MgSO$_4$), and then concentrated. The residue was subjected to column chromatography on silica gel, and ethyl E-2-hydroxyiminohexanoate (11.0 g, yield 71%) was obtained as crystals from a fraction eluted with ethyl acetate-hexane (1:4, v/v). Recrystallization from hexane gave colorless crystals. m.p. 49–50° C.

Reference Example 20

To a solution of diethyl oxalate (19.6 g) in diethyl ether (400 ml), a solution of isopropylmagnesium bromide in tetrahydrofuran (0.67 M, 100 ml) was added dropwise at −78° C. under a nitrogen atmosphere. After stirring for 1 hour, the reaction mixture was allowed to warm to 0° C., and then 1N hydrochloric acid was added. A diethyl ether layer was separated, washed with aqueous sodium bicarbonate and then with saturated aqueous sodium chloride, dried (MgSO$_4$), and concentrated. The residue was dissolved in ethanol (100 ml), and hydroxylamine hydrochloride (5.59 g) and sodium acetate (8.24 g) were added. The mixture was heated under reflux for 15 hours. The reaction mixture was concentrated, and the residue was diluted with water and extracted with ethyl acetate. The ethyl acetate layer was washed with water, dried (MgSO$_4$), and then concentrated. The residue was subjected to column chromatography on silica gel, and ethyl 2-hydroxyimino-3-methylbutyrate (a mixture of E- and Z-forms) was obtained from a fraction eluted with ethyl acetate-hexane (1:4, v/v). Recrystallization from hexane gave ethyl E-2-hydroxyimino-3-methylbutyrate (1.91 g, yield 18%) as colorless crystals. m.p. 54–55° C.

NMR (CDCl$_3$) δ: 1.24 (6H, d, J=7.0 Hz), 1.35 (3H, t, J=7.1 Hz), 3.49 (1H, sept, J=7.0 Hz), 4.29 (2H, q, J=7.1 Hz), 9.79 (1H, br s).

Reference Example 21

The mother liquid of the E-form obtained in Reference Example 20 was concentrated to obtain a mixture of E:Z= 2.3:1 (5.69 g, yield 53%).

Z:NMR (CDCl$_3$) δ: 1.17 (6H, d, J=6.6 Hz), 1.36 (3H, t, J=7.1 Hz), 2.80 (1H, sept, J=6.6 Hz), 4.36 (2H, q, J=7.1 Hz), 9.75 (1H, br s).

Reference Example 22

To a mixture of aluminum chloride (29.3 g) and dichloromethane (250 ml), ethyl chloroglyoxylate (22.3 ml) was added dropwise at 0° C. After stirring for 30 minutes, diphenyl ether (63.5 ml) was added dropwise over 30 minutes at 0° C. followed by stirring for 2 hours, the reaction mixture was poured onto ice (250 g) and stirred for 1 hour at room temperature. The dichloromethane layer was separated, washed with saturated aqueous sodium chloride, dried (MgSO$_4$), and then concentrated. The residue was subjected to column chromatography on silica gel, and ethyl 4-phenoxyphenylglyoxylate (38.0 g, yield 70%) was obtained as an oil from a fraction eluted with ethyl acetate-hexane (1:10, v/v).

NMR (CDCl$_3$) δ: 1.42 (3H, t, J=7.1 Hz), 4.44 (2H, q, J=7.1 Hz), 6.98–7.13 (4H, m), 7.20–7.29 (1H, m), 7.37–7.47 (2H, m), 8.01 (2H, d, J=9.0 Hz).

Reference Example 23

A mixture of ethyl 4-phenoxyphenylglyoxylate (37.9 g), hydroxylamine hydrochloride (11.7 g), sodium acetate (17.3 g) and ethanol (200 ml) was heated under reflux for 15 hours. The reaction mixture was concentrated, and the residue was diluted with water and extracted with ethyl acetate. The ethyl acetate layer was washed with water, dried (MgSO$_4$), and then concentrated. The residual crystals were recrystallized from toluene-hexane to obtain ethyl E-2-hydroxyimino-2-(4-phenoxyphenyl)acetate (11.0 g, yield 28%) as a colorless oil. m.p. 131–132° C.

Reference Example 24

The mother liquid of the E-form obtained in Reference Example 23 was concentrated, and the residue was subjected to column chromatography on silica gel to obtain ethyl Z-2-hydroxyimino-2-(4-phenoxyphenyl)acetate (23.6 g, yield 56%) as an oil from a fraction eluted with ethyl acetate-hexane (1:4, v/v).

NMR (CDCl$_3$) δ: 1.40 (3H, t, J=7.1 Hz), 4.46 (2H, q, J=7.1 Hz), 6.95–7.08 (4H, m), 7.11–7.20 (1H, m), 7.32–7.42 (2H, m), 7.53 (1H, d, J=8.8 Hz), 8.42–8.49 (1H, m).

Reference Example 25

To a mixture of aluminum chloride (41.6 g) and 1,2-dichloroethane (300 ml), ethyl chloroglyoxylate (32.0 ml) was added dropwise at 0° C. After stirring for 30 minutes, 4-fluorobenzene (25.0 g) was added at 0° C. After stirring for 2 hours at 40° C., the reaction mixture was poured onto ice (300 g), and the mixture was stirred for 1 hour at room temperature. The 1,2-dichloroethane layer was separated and washed with saturated aqueous sodium chloride, dried (MgSO$_4$), and then concentrated. The residue was dissolved in ethanol (300 ml), and admixed with hydroxylamine hydrochloride (21.7 g) and sodium acetate (32.0 g), and then heated under reflux for 20 hours. The reaction mixture was concentrated, and the residue was diluted with water, extracted with ethyl acetate. The ethyl acetate layer was washed with water, dried (MgSO$_4$), and then concentrated. The residue was subjected to column chromatography on silica gel to obtain ethyl Z-2-(4-fluorophenyl)-2-hydroxyiminoacetate (3.82 g, yield 6%) as an oil from a fraction eluted with ethyl acetate-hexane (1:3, v/v).

NMR (CDCl$_3$) δ: 1.40 (3H, t, J=7.1 Hz), 4.46 (2H, q, J=7.1 Hz), 7.05–7.14 (2H, m), 7.52–7.61 (2H, m), 8.37 (1H, s).

Reference Example 26

From a fraction eluted following the Z-form in Reference Example 25, ethyl E-2-(4-fluorophenyl)-2-hydroxyiminoacetate (2.45 g, yield 5%) was obtained as crystals. Recrystallization from ethyl acetate-hexane gave colorless crystals. m.p. 117–118° C.

Reference Example 27

To a mixture of aluminum chloride (41.6 g) and 1,2-dichloroethane (300 ml), ethyl succinyl chloride (40.8 ml) was added dropwise at 0° C. After stirring for 30 minutes, 4-fluorobenzene (25.0 g) was added at 0° C. After stirring for 15 hours at 60° C., the reaction mixture was poured onto ice (500 g), and the mixture was stirred for 1 hour at room temperature. The 1,2-dichloroethane layer was separated and washed with saturated aqueous sodium chloride, dried (MgSO$_4$), and then concentrated. The residue was dissolved in ethanol (300 ml), and admixed with hydroxylamine hydrochloride (21.7 g) and sodium acetate (32.0 g), and then heated under reflux for 20 hours. The reaction mixture was concentrated, and the residue was diluted with water, extracted with ethyl acetate. The ethyl acetate layer was washed with water, dried (MgSO$_4$), and then concentrated. The residue was subjected to column chromatography on silica gel to obtain ethyl E-4-(4-fluorophenyl)-4-hydroxyiminobutyrate (7.45 g, yield 12%) as an oil from a fraction eluted with ethyl acetate-hexane (1:4, v/v).

NMR (CDCl$_3$) δ: 1.23 (3H, t, J=7.1 Hz), 2.56–2.65 (2H, m), 3.05–3.14 (2H, m), 4.11 (2H, q, J=7.1 Hz), 7.01–7.14 (2H, m), 7.56–7.66 (2H, m), 8.05–8.40 (1H, br s).

Reference Example 28

To a solution of 3-phenoxybenzylalcohol (25.0 g) and triethylamine (26.3 ml) in ethyl acetate (300 ml), methanesulfonyl chloride (14.6 ml) was added dropwise at 0° C. After stirring for 1 hour, the reaction mixture was washed with saturated aqueous sodium chloride, dried (MgSO$_4$) and concentrated. The residue was dissolved in acetone (300 ml), admixed with sodium iodide (37.5 g) and then stirred for 1 hour. The reaction mixture was concentrated, and the residue was diluted with water and then extracted with ethyl acetate. The ethyl acetate layer was washed with water, dried (MgSO$_4$), and then concentrated. The residue was dissolved in dimethyl sulfoxide (100 ml) and stirred with sodium cyanide (7.35 g) for 15 hours at room temperature. The reaction mixture was diluted with ethyl acetate, washed with water, dried (MgSO$_4$), and then concentrated. The residue was subjected to column chromatography on silica gel to obtain 3-phenoxyphenylacetonitrile (8.36 g, yield 32%) as an oil from a fraction eluted with ethyl acetate-hexane (1:7. v/v).

NMR (CDCl$_3$) δ: 3.72 (2H, s), 6.90–7.20 (6H, m), 7.28–7.43 (3H, m).

Reference Example 29

To a solution of sodium ethoxide prepared from sodium (1.09 g) and ethanol (20 ml), a solution of 3-phenoxyphenylacetonitrile (8.30 g) in ethanol (15 ml) was added dropwise at 0° C., and then isoamyl nitrite (7.99 ml) was added dropwise. After stirring for 15 hours at room temperature, diethyl ether was added and the mixture was washed sequentially with 1N HCl, aqueous sodium bicarbonate and then saturated aqueous sodium chloride. The diethyl ether layer was dried (MgSO$_4$), concentrated, and the residue was subjected to column chromatography on silica gel. The crystals obtained from a fraction eluted with ethyl acetate-hexane (1:4, v/v) were recrystallized with ethyl acetate-hexane to obtain 2-hydroxyimino-2-(3-phenoxyphenyl)acetonitrile (4.25 g, yield: 45%) as pale-yellow crystals. A mixture of the E-form and the Z-form. m.p. 124–125° C.

Reference Example 30

A mixture of 2-hydroxyimino-2-(3-phenoxyphenyl) acetonitrile (3.00 g), potassium hydroxide (3.40 g), ethanol (15 ml) and water (15 ml) was heated under reflux for 24 hours. The reaction mixture was acidified with 1 N HCl, and extracted with ethyl acetate. The ethyl acetate layer was washed with saturated aqueous sodium chloride, dried (MgSO$_4$) and then concentrated. The reaction mixture was dissolved in methanol (30 ml), admixed with concentrated sulfuric acid (a catalytic amount), and then heated under reflux for 24 hours. The reaction mixture was combined with aqueous sodium bicarbonate and extracted with ethyl acetate. The ethyl acetate layer was washed with saturated aqueous sodium chloride, dried (MgSO$_4$) and then concentrated. The residue was subjected to column chromatography on silica gel to obtain methyl Z-2-hydroxyimino-2-(3-phenoxyphenyl)acetate (1.14 g, yield 33%) as an oil from a fraction eluted with ethyl acetate-hexane (1:2, v/v).

NMR (CDCl$_3$) δ: 3.95 (3H, s), 6.99–7.18 (4H, m), 7.21–7.28 (2H, m), 7.31–7.41 (3H, m), 8.33 (1H, s).

Reference Example 31

From a fraction eluted following the Z-form in Reference Example 30, methyl E-2-hydroxyimino-2-(3-phenoxyphenyl)acetate (746 mg, yield 22%) was obtained as crystals. Recrystallization from ethyl acetate-hexane gave colorless crystals. m.p. 122–123° C.

Reference Example 32

A solution of 4-bromophenylmagnesium bromide prepared from p-dibromobenzene (25.0 g), magnesium (2.43 g) and diethyl ether (250 ml) was added dropwise to a solution of diethyl oxalate (32.5 g) in diethyl ether (250 ml) at −78° C. under a nitrogen atmosphere. After stirring for 1 hour, the reaction mixture was allowed to warm to 0° C., and 1N HCl was added. The diethyl ether layer separated, washed with aqueous sodium bicarbonate and with saturated aqueous sodium chloride, dried (MgSO$_4$), and concentrated. The residue was subjected to column chromatography on silica gel to obtain an oil from a fraction eluted with ethyl acetate-hexane (1:15, v/v). This oil was dissolved in ethanol (100 ml), combined with hydroxylamine hydrochloride (4.17 g) and sodium acetate (6.15 g), and then heated under reflux for 18 hours. The reaction mixture was concentrated, and the residue was diluted with water and extracted with ethyl acetate. The ethyl acetate layer was washed with saturated aqueous sodium chloride, dried (MgSO$_4$) and then concentrated. The residual crystals were recrystallized from isopropyl ether-hexane to obtain ethyl E-2-(4-bromophenyl)-2-hydroxyiminoacetate (4.31 g, yield 16%) as crystals. m.p. 163–164° C.

Reference Example 33

From a fraction eluted following the E-form in Reference Example 32, ethyl Z-2-(bromophenyl)-2-hydroxyiminoacetate (5.31 g, yield 20%) was obtained as an oil.

NMR (CDCl$_3$) δ: 1.40 (3H, t, J=7.1 Hz), 4.55 (2H, q, J=7.1 Hz)), 7.43 (2H, d, J=8.6 Hz), 7.54 (2H, d, J=8.6 Hz), 8.47 (1H, s).

Reference Example 34

To a solution of sodium ethoxide prepared from sodium (7.22 g) and ethanol (400 ml), ethyl phenylacetate (25.8 g) and diethyl oxalate (45.9 g) were added and the mixture was stirred for 1.5 hours at 70° C. with separating ethanol. The reaction mixture was combined with ethyl acetate (500 ml) and 1N HCl (350 ml), and the ethyl acetate layer was separated. The ethyl acetate layer was washed with saturated aqueous sodium chloride, dried (MgSO$_4$) and then concentrated. The residue was dissolved in dimethyl sulfoxide (150 ml)-water (15 ml), admixed with sodium chloride (9.18 g), and then the mixture was stirred for 1.5 hours at 130° C. The reaction mixture was diluted with water and extracted with ethyl acetate. The ethyl acetate layer was washed with saturated aqueous sodium chloride, dried (MgSO$_4$), and then concentrated. The residue was dissolved in ethanol (100 ml), admixed with hydroxylamine (3.34 g) and sodium acetate (4.92 g), and then the mixture was heated under reflux for 17 hours. The reaction mixture was concentrated, and the residue was combined with water, and then extracted with ethyl acetate. The ethyl acetate layer was washed with saturated aqueous sodium chloride, dried (MgSO$_4$) and then concentrated. The residue was subjected to column chromatography on silica gel to obtain ethyl E-2-hydroxyimino-3-phenylpropionate (6.94 g, yield 21%) as crystals from a fraction eluted with ethyl acetate-hexane (1:3, v/v). Recrystallization from ethyl acetate-hexane gave colorless crystals. m.p. 54–55° C.

Reference Example 35 n-Butyllithium (1.6N hexane solution, 108 ml) was added dropwise to a diethyl ether solution (400 ml) of 3-bromopyridine (25.7 g) at −78° C. over 1 hour under nitrogen atmosphere. After stirring for 30 minutes, a diethyl ether solution (100 ml) of diethyl oxalate (28.6 g) was added dropwise thereto at −78° C. over 1 hour. The reaction mixture was further mixed for 30 minutes, allowed to warm to 0° C., and 1N hydrochloric acid (200 ml) was added thereto. After stirring for 30 minutes, sodium bicarbonate was added thereto to neutralize the reaction mixture. The organic layer was separated, washed with an aqueous saturated solution of sodium chloride, dried (MgSO$_4$) and concentrated. The residue was subjected to silica gel chromatography to obtain ethyl 3-pyridylglyoxylate (13.1 g, yield 45%) from an ethyl acetate-hexane (1:1, v/v)-eluted fraction.

NMR (CDCl$_3$) δ: 1.45 (3H, t, J=7.1 Hz), 4.48 (2H, q, J=7.1 Hz), 7.45–7.53 (1H, m), 8.33–8.41 (1H, m), 8.85–8.90 (1H, m), 9.26–9.29 (1H, m).

Reference Example 36

A mixture of ethyl 3-pyridylglyoxylate (6.00 g), hydroxylamine hydrochloride (2.79 g), sodium acetate (4.13 g) and ethanol (80 ml) was heated to reflux for 15 hours. The reaction mixture was concentrated, water was added to the residue, and extracted with ethyl acetate. The ethyl acetate layer was washed with an aqueous saturated solution of sodium chloride, dried (MgSO$_4$) and concentrated. The remaining crystals were recrystallized from ethyl acetate to obtain ethyl E-2-hydroxyimino-2-(3-pyridyl)-acetate (3.30 g, yield 51%) as colorless crystals. m.p. 172–173° C.

Reference Example 37

The mother liquid of Reference Example 36 was concentrated and the residue was subjected to silica gel chromatography to obtain the crystals from an ethyl acetate-hexane (3:2, v/v)-eluted fraction. The crystals were recrystallized from ethyl acetate-hexane to obtain ethyl Z-2-hydroxyimino-2-(3-pyridyl)acetate (1.55 g, yield 24%) as colorless crystals. m.p. 137–138° C.

Reference Example 38

To a solution of sodium ethoxide prepared from sodium (2.51 g) and ethanol (40 ml) was added dropwise a solution of 2-(3-bromophenyl)acetonitrile (17.8 g) in ethanol (30 ml) at 0° C., and then isoamyl nitrite (18.3 ml) was added dropwise thereto. After stirring at room temperature for 18 hours, diethyl ether was added, and washed successively with 1N hydrochloric acid, an aqueous sodium bicarbonate solution, and an aqueous saturated solution of sodium chloride. The diethyl ether layer was dried (MgSO$_4$), concentrated, and the residue was subjected to silica gel chromatography to obtain 2-(3-bromophenyl)-2-(hydroxyimino)acetonitrile (19.9 g, yield 97%) as an orange paste from an ethyl acetate-hexane (1:1, v/v)-eluted fraction. Recrystallization from ethyl acetate-hexane gave orange crystals. m.p. 91–93° C.

Reference Example 39

A 1,2-dibromoethane solution (12 ml) of bromine (5.43 ml) was added dropwise over 3 hours while refluxing to a 1,2-dibromoethane solution (40 ml) of 3-methylbenzophenone (20.0 g). After heating to reflux for 30 minutes, the reaction mixture was concentrated. The residue was dissolved in dimethyl sulfoxide (100 ml) and stirred with sodium cyanide (7.50 g) at room temperature for 2 hours. The reaction mixture was diluted with water and extracted with ethyl acetate. The ethyl acetate layer was washed with an aqueous saturated solution of sodium chloride, dried (MgSO$_4$) and concentrated. The residue was subjected to silica gel chromatography to obtain 2-(3-benzoylphenyl)acetonitrile (13.8 g, yield 61%) as a yellow oil from an ethyl acetate-hexane (1:3, v/v)-eluted fraction.

NMR (CDCl$_3$) δ: 3.84 (2H, s), 7.46–7.68 (5H, m), 7.73–7.83 (4H, m).

Reference Example 40

To a solution of sodium ethoxide prepared from sodium (1.70 g) and ethanol (40 ml) was added dropwise a solution of 2-(3-benzoylphenyl)acetonitrile (13.6 g) in ethanol (30 ml) at 0° C., and then isoamyl nitrite (12.4 ml) was added dropwise. After stirring at room temperature for 15 hours, the reaction mixture was diluted with ethyl acetate and washed successively with 1N hydrochloric acid and an aqueous saturated solution of sodium chloride. The ethyl acetate layer was dried (MgSO$_4$) and concentrated to obtain 2-(3-benzoylphenyl)-2-(hydroxyimino)acetonitrile (15.2 g, yield 99%) as crystals. Recrystallization from ethyl acetate-hexane gave an isomer of 2-(3-benzoylphenyl)-2-(hydroxyimino)acetonitrile as colorless crystals. m.p. 175–176° C.

Reference Example 41

The mother liquid of Reference Example 40 was concentrated, and the residue was recrystallized from ethyl acetate-hexane to obtain another isomer of 2-(3-benzoylphenyl)-2-(hydroxyimino)acetonitrile as colorless crystals. m.p. 147–148° C.

Reference Example 42

A mixture of 2-(3-bromophenyl)-2-(hydroxyimino) acetonitrile (19.0 g), 4N aqueous solution of potassium hydroxide (100 ml) and 2-methoxyethanol (100 ml) was heated under reflux for 4 hours. The reaction mixture was cooled to room temperature, 1N hydrochloric acid was added to make the solution acidic and extracted with ethyl acetate. The ethyl acetate layer was washed with an aqueous saturated solution of sodium chloride, dried (MgSO$_4$) and concentrated. The residue was dissolved in ethanol (200 ml) and concentrated sulfuric acid (catalytic amount) was added. The reaction mixture was heated under reflux for 48 hours, cooled to room temperature, poured into an aqueous saturated solution of sodium bicarbonate and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-(3-bromophenyl)-2-(hydroxyimino)acetate (3.31 g, yield 14%) as a pale-brown oil from an ethyl acetate-hexane (1:3, v/v)-eluted fraction.

NMR (CDCl$_3$) δ: 1.41 (3H, t, J=7.1 Hz), 4.47 (2H, q, J=7.1 Hz), 7.23–7.32 (1H, m), 7.45–7.60 (2H, m), 7.72–7.75 (1H, m), 8.56 (1H, br s).

Reference Example 43

Ethyl E-2-(3-bromophenyl)-2-(hydroxyimino)acetate was obtained as crystals from a fraction which eluted following the Z-isomer in Reference Example 42. Recrystallization from ethyl acetate-hexane gave colorless crystals (1.52 g, yield 7%). m.p. 113–114° C.

Reference Example 44

A mixture of 2-(3-benzoylphenyl)-2-(hydroxyimino) acetonitrile (14.5 g), 4N aqueous solution of potassium hydroxide (80 ml) and ethanol (80 ml) was heated under reflux for 20 hours. The reaction mixture was cooled to room temperature, 1N hydrochloric acid was added to make the solution acidic and extracted with ethyl acetate. The ethyl acetate layer was washed with an aqueous saturated solution of sodium chloride, dried (MgSO$_4$) and concentrated. The residue was dissolved in ethanol (150 ml) and concentrated sulfuric acid (catalytic amount) was added. The reaction mixture was heated under reflux for 15 hours, cooled to room temperature, poured into an aqueous saturated solution of sodium bicarbonate and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-(3-benzoylphenyl)-2-(hydroxyimino)acetate (2.48 g, yield 14%) as a pale-brown oil from an ethyl acetate-hexane (1:2, v/v)-eluted fraction.

NMR (CDCl$_3$) δ: 1.38 (3H, t, J=7.1 Hz), 4.45 (2H, q, J=7.1 Hz), 7.30–7.66 (4H, m), 7.70–8.00 (5H, m), 8.66 (1H, br s).

Reference Example 45

Ethyl E-2-(3-benzoylphenyl)-2-(hydroxyimino)acetate was obtained as crystals from a fraction which eluted following the Z-isomer in Reference Example 44. Recrystallization from ethyl acetate-hexane gave orange crystals (1.70 g, yield 10%). m.p. 109–110° C.

Reference Example 46

To a mixture of aluminum chloride (14.7g) and dichloromethane (120 ml) was added dropwise ethyl succinyl chloride (14.3 ml) at 0° C. After stirring for 30 minutes, this was added dropwise to a solution of diphenyl ether (34.0 g) in dichloromethane (50 ml) at 0° C. After stirring for 3 hours, the reaction mixture was poured onto ice (200 g), and stirred at room temperature for 1 hour. The dichloromethane layer was separated, washed with an aqueous saturated solution of sodium chloride, dried ($MgSO_4$) and concentrated. The residue was dissolved in ethanol (150 ml), and hydroxylaniine hydrochloride (8.34 g) and sodium acetate (12.3 g) were added. After refluxing for 15 hours, the reaction mixture was concentrated, water was added to the residue and extracted with ethyl acetate. The ethyl acetate layer was washed with an aqueous saturated solution of sodium chloride, dried ($MgSO_4$) and concentrated. The residue was subjected to silica gel chromatography to obtain ethyl E-4-(hydroxyimino)-4-(4-phenoxyphenyl)butyrate (10.5 g, yield 34%) as a colorless oil from an ethyl acetate-hexane (1:4, v/v)-eluted fraction.

NMR ($CDCl_3$) δ: 1.23 (3H, t, J=7.1 Hz), 2.57–2.66 (2H, m), 3.06–3.15 (2H, m), 4.12 (2H, q, J=7.1 Hz), 6.97–7.19 (5H, m), 7.31–7.42 (2H, m), 7.59 (2H, d, J=9.2 Hz), 7.90–8.60 (1H, br).

Reference Example 47

A mixture of 2-chloropyrimidine (20.8 g) and 2-(methylamino)ethanol (180 ml) was heated at 120° C. for 15 hours and concentrated. The residue was dissolved in ethyl acetate, washed with an aqueous saturated solution of sodium chloride, dried ($MgSO_4$) and concentrated. The residue was distilled under reduced pressure to obtain 2-(methyl-2-pyrimidylamino)ethanol (24.6 g, yield 88%) as a colorless oil. b.p. 130–132° C./1–1.5 mmHg

Reference Example 48

Sodium hydride (60% in oil, 4.40 g) was added to a solution of 2-(methyl-2-pyrimidylamino)ethanol (15.3 g) in N,N-dimethylformamide (400 ml) at room temperature under nitrogen atmosphere and stirred for 1 hour. A solution of 4-fluorobenzaldehyde (13.6 g) in N,N-dimethylformamide (100 ml) was added dropwise and stirred at room temperature for 15 hours. The reaction mixture was poured onto ice (200 g) and concentrated. The residue was dissolved in ethyl acetate, washed with an aqueous saturated solution of sodium chloride, dried ($MgSO_4$) and concentrated. The residue was subjected to silica gel chromatography to obtain 4-[2-(methyl-2-pyrimidylamino)ethoxy]benzaldehyde (18.4 g, yield 72%) as crystals from an ethyl acetate-hexane (1:1, v/v)-eluted fraction. Recrystallization from ethyl acetate-hexane gave colorless crystals. m.p. 74–75° C.

Reference Example 49

To a solution of 4-[2-(methyl-2-pyrimidylamino)ethoxy]benzaldehyde (16.6 g) in methanol (40 ml)-tetrahydrofuran (40 ml) was added sodium borohydride (1.22 g) in portions at 0° C. After stirring for 1 hour, water was added to the reaction mixture and extracted with ethyl acetate. The ethyl acetate layer was washed with an aqueous saturated solution of sodium chloride, dried ($MgSO_4$) and concentrated. The residual crystals were recrystallized from ethyl acetate-hexane to obtain 4-[2-(methyl-2-pyrimidylamino)ethoxy]benzylalcohol (15.3 g, yield 91%) as colorless crystals. m.p. 73–74° C.

Reference Example 50

A mixture of 4-(4-chloromethylphenoxymethyl)-5-methyl-2-phenyloxazole (5.00 g), N-hydroxyphthalimide (2.59 g), potassium carbonate (4.40 g) and N,N-dimethylformamide (50 ml) was stirred at room temperature for 20 hours, and water (500 ml) was added. The resultant crystals were filtered, and washed with water to obtain N-[4-(5-methyl-2-phenyl-4-oxazolylmethoxy)benzyloxy]phthalimide (6.49 g, yield 93%) as colorless crystals. m.p. 155–156° C.

Reference Example 51

Sodium hydride (60% in oil, 649 mg) was added to a solution of 2-(5-methyl-2-phenyl-4-oxazolyl)ethanol (3.00 g) in N,N-dimethylformamide (60 ml) at room temperature under nitrogen atmosphere and stirred at room temperature for 1 hour. A solution of 4-fluorobenzaldehyde (2.02 g) in N,N-dimethylformamide (15 ml) was added dropwise and stirred at room temperature for 12 hours. The reaction mixture was poured onto ice (50 g) and concentrated. The residue was dissolved in ethyl acetate, washed with an aqueous saturated solution of sodium chloride, dried ($MgSO_4$) and concentrated. The residue was subjected to silica gel chromatography to obtain an oil from an ethyl acetate-hexane (1:4, v/v)-eluted fraction. This was dissolved in tetrahydrofuran (20 ml) and methanol (20 ml), and sodium borohydride (321 mg) was added at 0° C., and then stirred for 1 hour. Water was added to the reaction mixture and extracted with ethyl acetate. The ethyl acetate layer was washed with an aqueous saturated solution of sodium chloride, dried ($MgSO_4$) and concentrated. The residue was dissolved in toluene (20 ml), thionyl chloride (0.888 ml) was added at 0° C. and stirred for 1 hour. The reaction mixture was concentrated, and the remaining crystals were recrystallized from ethyl acetate-hexane to obtain 4-[2-(4-chloromethylphenoxy)ethyl]-5-methyl-2-phenyloxazole (2.51 g, yield 52%) as pale-yellow crystals. m.p. 93–94° C.

Reference Example 52

Hydrazine monohydrate (1.15 ml) was added to a solution of N-[4-(5-methyl-2-phenyl-4-oxazolylmethoxy)benzyloxy]phthalimide (5.22 g) in ethanol (40 ml)-tetrahydrofuran (40 ml) and heated under reflux for 3 hours. The reaction mixture was cooled to room temperature, diluted with an aqueous solution of potassium carbonate and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 4-(5-methyl-2-phenyl-4-oxazolylmethoxy)benzyloxyamine (3.32 g, yield 90%) as colorless crystals. m.p. 68–69° C.

Reference Example 53

A mixture of 5-chloro-2-(chloromethyl)imidazo[1,2-a]pyridine hydrochloride (3.00 g), 4-hydroxybenzaldehyde (1.81 g), potassium carbonate (6.14 g) and N,N-dimethylformamide (30 ml) was stirred at room temperature for 15 hours, poured into water and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 4-(5-chloroimidazo[1,2-a]pyridin-2-ylmethoxy)benzaldehyde (3.55 g, yield 98%) as colorless crystals. m.p. 126–130° C.

Reference Example 54

Sodium borohydride (232 mg) was added to a solution of 4-(5-chloroimidazo[1,2-a]pyridin-2-ylmethoxy)benzaldehyde (3.52 g) in methanol (10 ml)-tetrahydrofuran (50 ml) at 0° C. After stirring for 1 hour, water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate to obtain 4-(5-chloroimidazo[1,2-a]pyridin-2-ylmethoxy)benzylalcohol (2.34 g, yield 66%) as colorless crystals. m.p. 169–171° C.

Reference Example 55

Thionyl chloride (0.597 ml) was added dropwise to a mixture of 4-(5-chloroimidazo[1,2-a]pyridine-2-ylmethoxy)benzylalcohol (1.97 g), triethylamine (1.15 ml) and toluene (50 ml) at 0° C. After stirring for 1 hour, water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 5-chloro-2-(4-chloromethylphenoxymethyl)imidazo[1,2-a]pyridine (1.10 g, yield 52%) as colorless crystals. m.p. 114–115° C.

Reference Example 56

Carbonyldiimidazole (7.25 g) was added to a solution of 2-pyridinecarboxylic acid (5.00 g) in tetrahydrofuran (200 ml) at 0° C. After stirring at room temperature for 2 hours, the mixture was added dropwise to a solution of lithiated tert-butyl acetate prepared from tert-butyl acetate (17.5 ml) and lithium diisopropylamide (2N tetrahydrofuran solution, 65 ml) at –78° C. over 1 hour. After stirring for 15 minutes, 1N hydrochloric acid (250 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane(1:4, v/v)-eluted fraction. This was dissolved in tetrahydrofuran (100 ml), and sodium hydride (60% in oil, 1.06 g) was added at 0° C., and then the reaction mixture was stirred for 10 minutes. Further ethyl bromoacetate (2.00 ml) was added, stirred at 0° C. for 8 hours, 0.1N hydrochloric acid (300 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane (1:5, v/v)-eluted fraction. This was dissolved in toluene (200 ml), and p-toluenesulfonic acid (2.00 g) was added, and then the reaction mixture was stirred at 80° C. for 20 hours. An aqueous saturated solution of sodium bicarbonate was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl 4-oxo-4-(2-pyridyl)butyrate (1.56 g, yield 19%) from an ethyl acetate-hexane (1:2, v/v)-eluted fraction as a colorless oil.

NMR ($CDCl_3$) δ: 1.26 (3H, t, J=7.1 Hz), 2.76 (2H, d, J=6.7 Hz), 3.57 (2H, d, J=6.7 Hz), 4.16 (2H, q, J=7.1 Hz), 7.48 (1H, dd, J=4.8, 7.6 Hz), 7.84 (1H, dt, J=1.8, 7.6 Hz), 8.05 (1H, d, J=7.6 Hz), 8.69 (1H, dd, J=1.8, 4.8 Hz).

Reference Example 57

Oxalyl chloride (4.47 ml) and N,N-dimethylformamide (catalytic amount) were added to a solution of 2-furancarboxylic acid (5.00 g) in tetrahydrofuran (50 ml) at room temperature, which was stirred at room temperature for 1 hour, followed by concentration. The residue was dissolved in tetrahydrofuran (20 ml) and added dropwise to a solution of lithiated tert-butyl acetate prepared from tert-butyl acetate (19.3 ml) and lithium diisopropylamide (2N tetrahydrofuran solution, 72 ml) –78° C. over 1 hour. After stirring for 15 minutes, 1N hydrochloric acid (250 ml) was added and extracted with ethyl acetate. The ethyl acetate layer was washed with an aqueous saturated solution of sodium chloride, dried ($MgSO_4$) and concentrated. The residue was subjected to silica gel chromatography to obtain crystals from an ethyl acetate-hexane (1:5, v/v)-eluted fraction. Recrystallization from ethyl acetate-hexane gave tert-butyl 3-(2-furyl)-3-oxopropionate (3.28 g, yield 35%) as colorless crystals. m.p. 74–75° C.

Reference Example 58

Sodium hydride (60% in oil, 629 mg) was added to a solution of tert-butyl 3-(2-furyl)-3-oxopropionate (3.01 g) in tetrahydrofuran (80 ml) at 0° C. and stirred for 10 minutes. Ethyl bromoacetate (1.51 ml) was added to the mixture, and then the reaction mixture was stirred at room temperature for 4 hours, 0.1N hydrochloric acid (200 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane (1:5, v/v)-eluted fraction. This was dissolved in toluene (150 ml), and trifluoroacetic acid (2.64 ml) was added, and then the reaction mixture was stirred at 90° C. for 6 hours. An aqueous saturated solution of sodium bicarbonate was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl 4-(2-furyl)-4-oxobutyrate (2.22 g, yield 79%) as a colorless oil from an ethyl acetate-hexane (1:3, v/v)-eluted fraction.

NMR ($CDCl_3$) δ: 1.27 (3H, t, J=7.1 Hz), 2.74 (2H, t, J=6.7 Hz), 3.18 (2H, t, J=6.7 Hz), 4.15 (2H, q, J=7.1 Hz), 6.53–6.57 (1H, m), 7.23 (1H, d, J=3.6 Hz), 7.59 (1H, d, J=1.8 Hz).

Carbonyldiimidazole (7.25 g) was added to a solution of nicotinic acid (5.00 g) in tetrahydrofuran (100 ml) at 0° C. After stirring at room temperature for 2 hours, the mixture was added dropwise to a solution of lithiated tert-butyl acetate prepared from tert-butyl acetate (17.5 ml) and lithium diisopropylamide (2N tetrahydrofuran solution, 65 ml) at –78° C. over 1 hour. After stirring for 15 minutes, 1N hydrochloric acid (250 ml) was added and extracted with ethyl acetate. The ethyl acetate layer was washed with an aqueous saturated solution of sodium chloride, dried ($MgSO_4$) and concentrated. The residue was dissolved in tetrahydrofuran (100 ml), sodium hydride (60% in oil, 1.38 g) was added at 0° C. and stirred for 10 minutes. Ethyl bromoacetate (3.33 ml) was added to the mixture, and the reaction mixture was stirred at room temperature for 3 hours, 0.1N hydrochloric acid (350 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane (1:1, v/v)-eluted fraction. This oil was dissolved in toluene (150 ml), and trifluoroacetic acid (7.68 ml) was added and then the resultant mixture was stirred at 90° C. for 4 hours. An aqueous saturated solution of sodium bicarbonate was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl 4-oxo-4-(3-pyridyl)butyrate (3.39 g, yield 38%) as a colorless oil from an ethyl acetate-hexane (2:1, v/v)-eluted fraction.

NMR ($CDCl_3$) δ: 1.28 (3H, t, J=7.1 Hz), 2.79 (2H, t, J=6.6 Hz), 3.33 (2H, t, J=6.6 Hz), 4.17 (2H, q, J=7.1 Hz), 7.43 (1H, dd, J=4.8, 8.0 Hz), 8.23–8.30 (1H, m), 8.80 (1H, dd, J=1.6, 4.8 Hz), 9.22 (1H, d, J=2.2 Hz).

Reference Example 60

Carbonyldiimidazole (7.25 g) was added to a solution of 4-pyridinecarboxylic acid (5.00 g) in tetrahydrofuran (80 ml) at 0° C. After stirring at room temperature for 2 hours, the mixture was added dropwise to a solution of lithiated tert-butyl acetate prepared from tert-butyl acetate (17.5 ml) and lithium diisopropylamide (2N tetrahydrofuran solution, 65 ml) at −78° C. over 1 hour. After stirring for 15 minutes, 1N hydrochloric acid (250 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane (2:3, v/v)-eluted fraction. This oil was dissolved in tetrahydrofuran (100 ml), and sodium hydride (60% in oil, 1.16 g) was added at 0° C., and then the resultant reaction mixture was stirred for 10 minutes. Ethyl bromoacetate (2.88 ml) was added to the mixture, and the resultant mixture was stirred at room temperature for 24 hours, 0.1N hydrochloric acid (300 ml) was added and extracted with ethyl acetate. The ethyl acetate layer was washed with an aqueous saturated solution of sodium chloride, dried ($MgSO_4$) and concentrated. The residue was subjected to silica gel chromatography to obtain an oil from an ethyl acetate-hexane (1:1, v/v)-eluted fraction. This oil was dissolved in toluene (120 ml), and stirred with trifluoroacetic acid (5.64 ml) at 90° C. for 6 hours. An aqueous saturated solution of sodium bicarbonate was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl 4-oxo-4-(4-pyridyl)butyrate (2.61 g, yield 31%) from an ethyl acetate-hexane (2:1, v/v)-eluted fraction as a pale brown oil.

NMR ($CDCl_3$) δ: 1.27 (3H, t, J=7. 1 Hz), 2.78 (2H, t, J=6.5 Hz), 3.30 (2H, t, J=6.5 Hz), 4.17 (2H, q, J=7.1 Hz), 7.76 (2H, d, J=6.2 Hz), 8.83 (2H, d, J=6.2 Hz).

Reference Example 61

Sodium borohydride (1.18 g) was added to a solution of 3-(5-methyl-2-phenyl-4-oxazolylmethoxy)benzaldehyde (18.3 g) in methanol (50 ml)-tetrahydrofuran (100 ml) in portions at 0° C. After stirring for 30 minutes, water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 3-(5-methyl-2-phenyl-4-oxazolylmethoxy)benzylalcohol (15.5 g, yield 84%) as colorless crystals. m.p. 101–102° C.

Reference Example 62

Thionyl chloride (4.45 ml) was added dropwise to a mixture of 3-(5-methyl-2-phenyl-4-oxazolylmethoxy) benzylalcohol (15.0 g) and toluene (200 ml) at 0° C. After stirring at room temperature for 1 hour, water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 4-(3-chloromethylphenoxymethyl)-5-methyl-2-phenyloxazole (13.4 g, yield 84%) as pale-yellow crystals. m.p. 79–80° C.

Reference Example 63

A mixture of 4-(3-chloromethylphenoxymethyl)-5-methyl-2-phenyloxazole (8.00 g), N-hydroxyphthalimide (4.13 g), potassium carbonate (7.05 g) and N,N-dimethylformamide (80 ml) was stirred at room temperature for 20 hours and water (800 ml) was added. The resultant crystals were filtered and washed with water to obtain N-[3-(5-methyl-2-phenyl-4-oxazolylmethoxy)benzyloxy]phthalimide (10.1 g, yield 90%) as pale-brown crystals. m.p. 146–147° C.

Reference Example 64

Hydrazine monohydrate (0.661 ml) was added to a solution of N-[3-(5-methyl-2-phenyl-4-oxazolylmethoxy) benzyloxy]phthalimide (3.00 g) in ethanol (25 ml)-tetrahydrofuran (25 ml) and heated under reflux for 3 hours. The reaction mixture was cooled to room temperature, an aqueous solution of potassium carbonate was added and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 3-(5-methyl-2-phenyl-4-oxazolylmethoxy) benzyloxyamine (2.04 g, yield 97%) as pale-yellow crystals. m.p. 81–82° C.

Reference Example 65

A mixture of 2-aminopyridine (12.5 g), 1,3-dichloro-2-propanone (17.7 g) and acetonitrile (100 ml) was heated under reflux for 2 hours and concentrated. An aqueous saturated solution of sodium bicarbonate was added to the residue and extracted with ethyl acetate. The ethyl acetate layer was washed with an aqueous saturated solution of sodium chloride, dried ($MgSO_4$) and concentrated. The residue was subjected to silica gel chromatography to obtain crystals from an ethyl acetate-hexane (3:2, v/v)-eluted fraction. Recrystallization from ethyl acetate-hexane gave 2-chloromethylimidazo[1,2-a]pyridine (7.52 g, yield 34%) as pale-yellow crystals. m.p. 93–94° C.

Reference Example 66

Oxalyl chloride (0.508 ml) and N,N-dimethylformamide (catalytic amount) were added to a solution of 6-oxo-6-phenylhexanoic acid (1.00 g) in tetrahydrofuran (15 ml) at room temperature, which was stirred at room temperature for 1 hour and concentrated. The residue was dissolved in ethyl acetate (25 ml) and added dropwise to a stirred mixture of 25% aqueous ammonia (20 ml) and ethyl acetate (25 ml) at 0° C. After stirring at room temperature for 2 hours water (200 ml) was added and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 6-oxo-6-phenylhexanamide (885 mg, yield 89%) as colorless crystals. m.p. 113–114° C.

Reference Example 67

A mixture of acetophenone (25.0 ml) and diethyl oxalate (58.3 ml) was added to a solution of sodium ethoxide prepared from sodium (9.85 g) and ethanol (300 ml) and heated under reflux for 1 hour. The reaction mixture was concentrated, diluted with 1N hydrochloric acid (450 ml) and extracted with ethyl acetate. The ethyl acetate layer was washed with an aqueous saturated solution of sodium chloride, dried ($MgSO_4$) and concentrated. The residue was dissolved in ethanol (250 ml), and hydroxylamine hydrochloride (44.6 g) was added, and then the reaction mixture was refluxed for 1 hour. The reaction mixture was concentrated, water was added to the residue and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain ethyl 5-phenylisoxazole-3-carboxylate (31.5 g, yield 70%) as pale-brown crystals. m.p. 46–47° C.

Reference Example 68

Triethylamine (7.28 ml) was added to a solution of α-chlorobenzaldehyde oxime (4.04 g) and 2-propyn-1-ol (1.66 ml) in tetrahydrofuran (130 ml) and stirred at room temperature for 4 days. Water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain (3-phenyl-5-isoxazolyl)methanol (3.42 g, yield 75%) as colorless crystals. m.p. 48–49° C.

Reference Example 69

A solution of ethyl 5-phenylisoxazole-3-carboxylate (20.0 g) in diethyl ether (50 ml) was added dropwise to a mixture of lithium aluminium hydride (2.62 g) in diethyl ether (50 ml) at 0° C. After stirring for 1 hour, water was added to the reaction mixture carefully, followed by addition of 1N hydrochloric acid (200 ml) and extraction with ethyl acetate. The ethyl acetate layer was washed with an aqueous saturated solution of sodium chloride, dried ($MgSO_4$) and concentrated. The remaining crystals were recrystallized from ethyl acetate-hexane to obtain (5-phenyl-3-isoxazolyl)methanol (15.2 g, yield 94%) as pale-brown crystals m.p. 101–102° C.

Reference Example 70

Thionyl chloride (2.41 ml) was added to a solution of (3-phenyl-5-isoxazolyl)methanol (2.89 g) in toluene (10 ml) and stirred at 60° C. for 1 hour. Water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 5-(chloromethyl)-3-phenylisoxazole (2.75 g, yield 86%) as pale-brown crystals. m.p. 69–70° C.

Reference Example 71

Thionyl chloride (7.55 ml) was added to a solution of (5-phenyl-3-isoxazolyl)methanol (12.1 g) in toluene (50 ml) and stirred at 80° C. for 3 hours. Water was added to the reaction mixture and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain 3-(chloromethyl)-5-phenylisoxazole (11.8 g, yield 88%) as pale-yellow crystals. m.p. 46–47° C.

Reference Example 72

Chloromethyl methyl ether (34.2 ml) was added to a mixture of 4-hydroxybenzaldehyde (50.0 g), potassium carbonate (84.9 g) and N,N-dimethylformaldehyde (150 ml) at 0° C. and stirred at room temperature for 11 hours. Water was added to the reaction mixture and extracted with ethyl acetate. The ethyl acetate layer was washed with an aqueous saturated solution of sodium chloride, dried ($MgSO_4$) and concentrated. The residue was dissolved in tetrahydrofuran (300 ml) and methanol (50 ml) and sodium borohydride (7.76 g) was added in portions at 0° C. After stirring for 30 minutes, water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain 4-methoxymethoxybenzylalcohol (56.7 g, yield 82%) as a colorless oil from an ethyl acetate-hexane (2:3, v/v) eluted fraction.

NMR ($CDCl_3$) δ: 3.48 (3H, s), 4.63 (2H, s), 5.18 (2H, s), 7.03 (2H, d, J=8.8 Hz), 7.30 (2H, d, J=8.8 Hz).

Reference Example 73

Diethyl azodicarboxylate (40% toluene solution, 142 g) was added dropwise to a solution of 4-methoxymethoxybenzylalcohol (50.0 g), N-hydroxyphthalimide (44.1 g) and triphenylphosphine (83.7 g) in tetrahydrofuran (900 ml) at room temperature and stirred for 1 hour. The reaction mixture was concentrated. In order to remove triphenylphosphine oxide, the residue was subjected to silica gel chromatography to obtain crystals from an ethyl acetate-hexane (1:5, v/v)-eluted fraction. The crystals were washed with ethyl acetate-hexane (1:5, v/v) and then dissolved in tetrahydrofuran (200 ml) and ethanol (50 ml). To this solution was added hydrazine monohydrate (33.7 ml) and heated under reflux for 3 hours. The reaction mixture was cooled to room temperature, an aqueous solution of potassium carbonate was added and extracted with ethyl acetate. The ethyl acetate layer was washed with an aqueous saturated solution of sodium chloride, dried ($MgSO_4$) and concentrated. Isopropyl ether was added to the residue and filtered to remove insolubles. The filtrate was concentrated to obtain 4-methoxymethoxybenzyloxyamine (28.9 g, yield 58%) as a colorless oil.

NMR ($CDCl_3$) δ: 3.48 (3H, s), 4.63 (2H, s), 5.18 (2H, s), 7.04 (2H, d, J=8.6 Hz), 7.30 (2H, d, J=8.6 Hz).

Reference Example 74

A mixture of 4-methoxymethoxybenzyloxyamine (4.99 g), methyl 4-oxo-4-phenylbutyrate (5.71 g), acetic acid (5.10 ml), sodium acetate (4.87 g) and methanol (200 ml) was heated under reflux for 15 hours. The reaction mixture was cooled to room temperature, dilute hydrochloric acid was added to the residue and extracted with ethyl acetate. The ethyl acetate layer was washed with an aqueous saturated solution of sodium chloride, dried ($MgSO_4$) and concentrated. The residue was dissolved in tetrahydrofuran (50 ml) and methanol (5 ml). To this solution was added 1N hydrochloric acid (10 ml) and heated under reflux for 3 hours. The reaction mixture was cooled to room temperature, water was added and extracted with ethyl acetate. The ethyl acetate layer was washed with an aqueous saturated solution of sodium chloride, dried ($MgSO_4$) and concentrated. The residue was subjected to silica gel chromatography to obtain methyl E-4-(4-hydroxybenzyloxyimino)-4-phenylbutyrate (4.24 g, yield 50%) as a colorless oil from an ethyl acetate-hexane (2:5, v/v)-eluted fraction.

NMR (CDCl$_3$) δ: 2.50–2.59 (2H, m), 3.01–3.10 (2H, m), 3.63 (3H, s), 4.97–5.05 (1H, m), 5.14 (2H, s), 6.82 (2H, d, J=8.8 Hz), 7.25–7.38 (5H, m), 7.59–7.65 (2H, m).

Reference Example 75

Sodium hydride (60% in oil, 2.18 g) was added to a solution of ethyl benzoylacetate (10.0 g) in N,N-dimethylformamide (100 ml) at 0° C. and stirred for 30 minutes. To this mixture was added methyl iodide (3.89 ml) and stirred for 1 hour. Sodium hydride (60% in oil, 2.18 g) was added to the mixture, and stirred for 30 minutes. Further, methyl iodide (3.89 ml) was added and stirred for 1 hour. The reaction mixture was poured into 0.05N hydrochloric acid (1000 ml) and extracted with ethyl acetate. The ethyl acetate layer was washed with an aqueous saturated solution of sodium chloride, dried (MgSO$_4$) and concentrated. The residue was subjected to silica gel chromatography to obtain ethyl 2,2-dimethyl-3-oxo-phenylpropionate (7.37 g, yield 64%) as a colorless oil from an ethyl acetate-hexane (1:20, v/v)-eluted fraction.

NMR (CDCl$_3$) δ: 1.05 (3H, t, J=7.1 Hz), 1.55 (6H, s), 4.12 (2H, q, J=7.1 Hz), 7.37–7.58 (3H, m), 7.81–7.87 (2H, m).

Reference Example 76

A mixture of 4-chloromethyl-5-methyl-2-phenyloxazole (15.6 g), methyl 4-hydroxyphenylacetate (12.5 g), potassium carbonate (20.8 g) and N,N-dimethylformamide (80 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl 4-(5-methyl-2-phenyl-4-oxazolylmethoxy)phenylacetate (23.8 g, yield 94%) as crystals from an ethyl acetate-hexane (1:4, v/v)-eluted fraction. The crystals were recrystallized from ethyl acetate-hexane to obtain colorless crystals. m.p. 74–75° C.

Reference Example 77

A mixture of methyl 4-(5-methyl-2-phenyl-4-oxazolylmethoxy)phenylacetate (23.2 g), lithium hydroxide monohydrate (4.33 g), tetrahydrofuran (100 ml), water (60 ml) and methanol (40 ml) was stirred at room temperature for 1 hour. 1N hydrochloric acid (103 ml) was added to the reaction mixture and extracted with ethyl acetate. The ethyl acetate layer was washed with an aqueous saturated solution of sodium chloride, dried (MgSO$_4$) and concentrated. The remaining crystals were recrystallized from acetone to obtain 4-(5-methyl-2-phenyl-4-oxazolylmethoxy)phenylacetic acid (21.9 g, yield 98%). m.p. 181–183° C.

Reference Example 78

Aluminium chloride (2.58 g) was added to a mixture of methyl 8-chloro-8-oxooctanoate (2.00 g) and anisole (5 ml) at 0° C. After stirring at room temperature for 14 hours, the reaction mixture was poured onto ice (50 g), stirred at room temperature for 1 hour and extracted with ethyl acetate. The ethyl acetate layer was washed with an aqueous saturated solution of sodium chloride, dried (MgSO$_4$) and concentrated. The residue was subjected to silica gel chromatography to obtain methyl 8-(4-methoxyphenyl)-8-oxooctanoate (2.37 g, yield 88%) as crystals. The crystals were recrystallized from ethyl acetate-hexane to obtain colorless crystals. m.p. 57–58° C.

Reference Example 79

Tert-butyldimethylsilyl chloride (24.1 g) was added to a mixture of 4-hydroxybenzaldehyde (17.8 g), imidazole (19.8 g) and N,N-dimethylformamide (100 ml). After stirring at room temperature for 2 hours, water was added and extracted with ethyl acetate. The ethyl acetate layer was washed with an aqueous saturated solution of sodium chloride, dried (MgSO$_4$) and concentrated. The residue was dissolved in tetrahydrofuran (300 ml) and methanol (40 ml), and then sodium borohydride (11.1 g) was added in portions at 0° C. After stirring for 30 minutes, water was added and extracted with ethyl acetate. The ethyl acetate layer was washed with an aqueous saturated solution of sodium chloride, dried (MgSO$_4$) and concentrated. The residue was subjected to silica gel chromatography to obtain 4-(tert-butyldimethylsilyloxy)benzylalcohol (27.7 g, yield 79%) as a colorless oil from an ethyl acetate-hexane (1:4, v/v)-eluted fraction.

NMR (CDCl$_3$) δ: 0.19 (6H, s), 0.98 (9H, s), 4.61 (2H, s), 6.83 (2H, d, J=8.4 Hz), 7.23 (2H, d, J=8.4 Hz).

Reference Example 80

Diethyl azodicarboxylate (40% toluene solution, 54.0 g) was added dropwise to a solution of 4-(tert-butyldimethylsilyloxy)benzylalcohol (27.5 g), N-hydroxyphthalimide (16.8 g) and triphenylphosphine (31.1 g) in tetrahydrofuran (450 ml) at room temperature and stirred for 18 hours. After the reaction mixture was concentrated, diisopropyl ether (200 ml) was added and the residual crystals were removed by filtration. The filtrate was concentrated, and the residue was subjected to silica gel chromatography to obtain N-[4-(tert-butyldimethylsilyloxy)benzyloxy]phthalimide (17.4 g, yield 43%) as crystals from an ethyl acetate-hexane-toluene (1:10:10, v/v)-eluted fraction. The crystals were recrystallized from ethyl acetate-hexane to obtain colorless crystals. m.p. 76–77° C.

Reference Example 81

Hydrazine monohydrate (1.25 ml) was added to a solution of N-[4-(tert-butyldimethylsilyloxy)benzyloxy]phthalimide (5.00 g) in ethanol (10 ml)-tetrahydrofuran (40 ml) and stirred at 60° C. for 1 hour. The reaction mixture was cooled to room temperature, an aqueous solution of potassium carbonate was added and extracted with ethyl acetate. The ethyl acetate layer was washed with an aqueous saturated solution of sodium chloride, dried (MgSO$_4$) and concentrated to obtain 4-(tert-butyldimethylsilyloxy)benzyloxyamine (3.15 g, yield 95%) as a colorless oil.

NMR (CDCl$_3$) δ: 0.19 (6H, s), 0.98 (9H, s), 4.62 (2H, s), 5.20–5.50 (2H, br), 6.83 (2H, d, J=8.6 Hz), 7.24 (2H, d, J=8.6 Hz).

Reference Example 82

A mixture of 4-(tert-butyldimethylsilyloxy)benzyloxyamine (3.10 g), ethyl 8-oxo-8-phenyloctanoate (6.32 g), acetic acid (2.07 ml), sodium acetate (1.98 g) and ethanol (80 ml) was heated under reflux for 20 hours. The reaction mixture was cooled to room temperature, water was added and extracted with ethyl acetate. The ethyl acetate layer was washed with an aqueous saturated solution of sodium chloride, dried (MgSO$_4$) and concentrated. The residue was dissolved in tetrahydrofuran (60 ml), tetrabutylammonium fluoride trihydrate (3.98 g) was added and stirred at room temperature for 1 hour. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-8-(4-hydroxybenzyloxyimino)-8-phenyloctanoate (3.55 g, yield 77%) as a colorless oil from an ethyl acetate-hexane (2:7, v/v)-eluted fraction.

NMR (CDCl$_3$) δ: 1.20–1.65 (11H, m), 2.18–2.27 (2H, m), 2.69–2.78 (2H, m), 4.12 (2H, q, J=7.1 Hz), 5.13 (2H, s), 5.39 (1H, br s), 6.83 (2H, d, J=8.4 Hz), 7.25–7.38 (5H, m), 7.57–7.63 (2H, m).

Reference Example 83

A mixture of benzonitrile (26.2 g), hydroxylamine hydrochloride (17.7 g), potassium carbonate (17.6 g) and 70% ethanol (250 ml) was stirred at 80° C. for 2 hours. The reaction mixture was cooled to room temperature, water was added to the reaction mixture and extracted with ethyl acetate. The ethyl acetate layer was washed with an aqueous saturated solution of sodium chloride, dried (MgSO$_4$) and concentrated. The residue was dissolve in acetone (250 ml) and potassium carbonate (19.0 g) was added. This mixture was cooled to 0° C. and chloroacetyl chloride (21.9 ml) was added dropwise. After stirring for 1 hour, the reaction mixture was concentrated. Water was added to the residue, the residual crystals were filtered, washed with water and dissolved in ethyl acetate. This solution was washed with an aqueous saturated solution of sodium chloride, dried (MgSO$_4$) and concentrated. The residue was dissolved in xylene (250 ml), and refluxed with separating water. After 2 hours, the solution was concentrated and the remaining crystals were washed with hexane to obtain 5-(chloromethyl)-3-phenyl-1,2,4-oxadiazole (25.2 g, yield 51%) as pale-yellow crystals. m.p. 38–39° C.

Reference Example 84

A mixture of 4-(tert-butyldimethylsilyloxy) benzyloxyamine (5.31 g), ethyl 6-oxo-6-phenylhexanoate (6.76 g), acetic acid (3.54 ml), sodium acetate (3.38 g) and ethanol (150 ml) was heated to reflux for 18 hours. The reaction mixture was cooled to room temperature, water was added and extracted with ethyl acetate. The ethyl acetate layer was washed with an aqueous saturated solution of sodium chloride, dried (MgSO$_4$) and concentrated. The residue was dissolved in tetrahydrofuran (100 ml), tetrabutylammonium fluoride trihydrate (10.0 g) was added and stirred at room temperature for 1 hour. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-(4-hydroxybenzyloxyimino)-6-phenylhexanoate (5.64 g, yield 77%) as a colorless oil from an ethyl acetate-hexane (2:7, v/v)-eluted fraction.

NMR (CDCl$_3$) δ: 1.22 (3H, t, J=7.1 Hz), 1.45–1.75 (4H, m), 2.23–2.31 (2H, m), 2.73–2,81 (2H, m), 4.09 (2H, q, J=7.1 Hz), 5.04 (1H, s), 5.13 (2H, s), 6.82 (2H, d, J=8.2 Hz), 7.25–7.38 (5H, m), 7.58–7.64 (2H, m).

Reference Example 85

Oxalyl chloride (5.39 ml) and N,N-dimethylformamide (catalytic amount) were added to a solution of 3-benzoylpropionic acid (10.0 g) in tetrahydrofuran (100 ml) at room temperature, which was stirred at room temperature for 1 hour and concentrated. The residue was dissolved in tetrahydrofuran (100 ml) and added dropwise to a 25% aqueous ammonia (100 ml) at 0° C. After stirring at room temperature for 30 minutes, water (1000 ml) and hexane (500 ml) were added, and then the residual crystals were filtered and washed with hexane to obtain 4-oxo-4-butyramide (2.67 g, yield 27%) as orange crystals. m.p. 126–127° C.

Reference Example 86

A solution of 2-[2-(methoxycarbonyl)ethyl]-2-phenyl-1,3-dioxolane (5.00 g) in diethyl ether (15 ml) was added dropwise to a mixture of lithium aluminium hydride (949 mg) and diethyl ether (30 ml) at 0° C. After stirring for 30 minutes, water was added to the reaction mixture carefully and the precipitates were removed by filtration. The filtrate was extracted with ethyl acetate. The ethyl acetate layer was washed with an aqueous saturated solution of sodium chloride, dried (MgSO$_4$) and concentrated. The residue was subjected to silica gel chromatography to obtain 2-(3-hydroxypropyl)-2-phenyl-1,3-dioxolane (3.81 g, yield 87%) as a colorless oil from an ethyl acetate-hexane (2:3, v/v)-eluted fraction.

NMR (CDCl$_3$) δ: 1.61–1.72 (2H, m), 2.02 (2H, t, J=6.4 Hz), 3.63 (2H, t, J=6.3 Hz), 3.74–3.87 (2H, m), 3.95–4.08 (2H, m), 7.24–7.49 (5H, m).

Reference Example 87

To a solution of 2-(3-hydroxypropyl)-2-phenyl-1,3-dioxolane (3.75 g) and triethylamine (5.05 ml) in ethyl acetate (100 ml) was added methanesulfonyl chloride (1.81 ml) at 0° C. After stirring for 30 minutes, water was added to the reaction mixture and extracted with ethyl acetate. The ethyl acetate layer was washed with an aqueous saturated solution of sodium chloride, dried (MgSO$_4$) and concentrated. The residue was dissolved in acetone (100 ml), sodium iodide (5.40 g) was added and stirred at 60° C. for 2 hours. The reaction mixture was concentrated, water was added to the residue and extracted with ethyl acetate. The ethyl acetate layer was washed with an aqueous saturated solution of sodium chloride, dried (MgSO$_4$) and concentrated. The residual crystals were recrystallized from ethyl acetate-hexane to obtain 2-(3-iodopropyl)-2-phenyl-1,3-dioxolane (5.41 g, yield 94%) as colorless crystals. m.p. 71–73° C.

Reference Example 88

N-butyllithium (1.6N hexane solution, 2.16 ml) was added dropwise to a solution of diisopropylamine (0.529 ml) in tetrahydrofuran (5 ml) at −20° C. under nitrogen atmosphere. After stirring for 20 minutes, the mixture was cooled to −78° C., and methyl isobutyrate (0.397 ml) in tetrahydrofuran (5 ml) was added dropwise over 30 minutes. The reaction mixture was further stirred for 20 minutes, 2-(3-iodopropyl)-2-phenyl-1,3-dioxolane (1.00 g) and hexamethylphosphoramide (0.602 ml) were added. After stirring at −40° C. for 3 hours, dilute hydrochloric acid was added and extracted with ethyl acetate. The ethyl acetate layer was washed with an aqueous saturated solution of sodium chloride, dried (MgSO$_4$) and concentrated. The residue was dissolved in acetone (30 ml), 1N sulfuric acid (10 ml) was added and heated under reflux for 3 hours. The reaction mixture was cooled to room temperature, water was added to the reaction mixture and extracted with ethyl acetate. The ethyl acetate layer was washed with an aqueous saturated solution of sodium chloride, dried (MgSO₄) and concentrated. The residue was subjected to silica gel chromatography to obtain methyl 2,2-dimethyl-6-oxo-6-phenylhexanoate (350 mg, yield 45%) as a colorless oil from an ethyl acetate-hexane (1:7, v/v)-eluted fraction.

NMR (CDCl₃) δ: 1.20 (6H, s), 1.55–1.80 (4H, m), 2.96 (2H, t, J=6.8 Hz), 3.65 (3H, s), 7.41–7.61 (3H, m), 7.92–8.02 (2H, m).

Reference Example 89

Sodium borohydride (325 mg) was added to a solution of 2-(5-methyl-2-phenyl-4-oxazolylmethoxy)benzaldehyde (5.00 g) in tetrahydrofuran (30 ml)-methanol (30 ml) at 0° C. After stirring for 1 hour, the reaction mixture was poured into water to give crystals. Recrystallization from acetone-ethyl acetate gave 2-(5-methyl-2-phenyl-4-oxazolylmethoxy)benzyl alcohol (4.17 g, yield 83%) as colorless prisms. m.p. 155–156° C.

Reference Example 90

Thionyl chloride (1.69 g) was added dropwise to a stirred suspension of 2-(5-methyl-2-phenyl-4-oxazolylmethoxy) benzyl alcohol (4.00 g) in toluene (60 ml) at 0° C. After stirring at room temperature for 2 hours, the reaction mixture was concentrated. The residual crystals were dissolved in ethyl acetate and washed with aqueous sodium bicarbonate and water. The ethyl acetate layer was separated, dried (MgSO₄), and concentrated to give 4-(2-chloromethylphenoxymethyl)-5-methyl-2-phenyloxazole as crystals. Recrystallization from ethyl acetate-hexane gave colorless needles (3.50 g, yield 82%). m.p. 103–104° C.

Reference Example 91

Sodium borohydride (540 mg) was added to a solution of 3,5-dimethoxy-4-(5-methyl-2-phenyl-4-oxazolylmethoxy) benzaldehyde (10.0 g) in tetrahydrofuran (70 ml)-methanol (30 ml) at 0° C. After stirring for 1 hour, the reaction mixture was poured into water to give 3,5-dimethoxy-4-(5-methyl-2-phenyl-4-oxazolylmethoxy)benzyl alcohol (9.25 g, yield 92%) as crystals. Recrystallization from ethyl acetate-hexane gave colorless prisms. m.p. 113–114° C.

Reference Example 92

Thionyl chloride (3.62 g) was added dropwise to a stirred suspension of 3,5-dimethoxy-4-(5-methyl-2-phenyl-4-oxazolylmethoxy)benzyl alcohol (9.00 g) in tetrahydrofuran (50 ml)-toluene (150 ml) at 0° C. After stirring at room temperature for 3 hours, the reaction mixture was concentrated. The residual crystals were dissolved in ethyl acetate and washed with aqueous sodium bicarbonate and water. The ethyl acetate layer was separated, dried (MgSO₄), and concentrated to give 4-(4-chloromethyl-2,6-dimethoxyphenoxymethyl)-5-methyl-2-phenyloxazole as crystals. Recrystallization from acetone-hexane gave colorless needles (7.00 g, yield 74%). m.p. 118–119° C.

Reference Example 93

Sodium borohydride (825 mg) was added to a solution of 4-[2-(2-furyl)-5-methyl-4-oxazolylmethoxy]-3-methoxybenzaldehyde (6.84 g) in tetrahydrofuran (50 ml)-methanol (50 ml) at 0° C. After stirring for 1 hour, the reaction mixture was poured into water to give 4-[2-(2-furyl)-5-methyl-4-oxazolylmethoxy]-3-methoxybenzyl alcohol (6.98 g, yield 92%) as crystals.

NMR (CDCl₃) δ: 2.41 (3H, s), 3.88 (3H, s), 4.63 (2H, s), 5.06 (2H, s), 6.5–6.55 (1H, m), 6.85–6.95 (1H, m), 6.95–7.05 (3H, m), 7.5–7.55 (1H, m).

Reference Example 94

Thionyl chloride (2.59 g) was added dropwise to a stirred suspension of 4-[2-(2-furyl)-5-methyl-4-oxazolylmethoxy]-3-methoxybenzyl alcohol (6.30 g) in tetrahydrofuran (100 ml) at 0° C. After stirring at room temperature for 1 hours, the reaction mixture was poured onto ice to give 4-(4-chloromethyl-2-methoxyphenoxymethyl)-2-(2-furyl)-5-methyloxazole as crystals (5.67 g, yield 85%).

NMR (CDCl₃): δ: 2.40 (3H, s), 3.88 (3H, s), 4.56 (2H, s), 5.05 (2H, s), 6.5–6.55 (2H, m), 6.9–7.05 (4H, m), 7.5–7.55 (1H, m).

Reference Example 95

In substantially the same manner in Reference Example 93, 3-methoxy-4-(5-methyl-2-phenyl-4-oxazolylmethoxy) benzaldehyde (6.47 g) was reduced by sodium borohydride (760 mg) to obtain 3-methoxy-4-(5-methyl-2-phenyl-4-oxazolylmethoxy)benzyl alcohol (6.11 g, yield 93%) as crystals.

NMR (CDCl₃) δ: 2.32 (3H, s), 3.79 (3H, s), 4.54 (2H, s), 4.96 (2H, s), 6.7–7.0 (3H, m), 7.3–7.4 (3H, m), 7.9–8.0 (2H, m).

Reference Example 96

In substantially the same manner in Reference Example 94, 3-methoxy-4-(5-methyl-2-phenyl-4-oxazolylmethoxy) benzyl alcohol (6.00 g) was reacted with thionyl chloride (1.58 g) to obtain 4-(4-chloromethyl-2-methoxyphenoxymethyl)-5-methyl-2-phenyloxazole (5.77 g, yield 91%) as crystals.

NMR (CDCl₃) δ: 2.32 (3H, s), 3.79 (3H, s), 4.47 (2H, s), 4.97 (2H, s), 6.7–7.0 (3H, m), 7.3–7.4 (3H, m), 7.9–8.0 (2H, m).

Example 1

To a solution of 4-(5-methyl-2-phenyl-4-oxazolylmethoxy)benzylalcohol (1.32 g) in toluene (10 ml), thionyl chloride (0.488 ml) was added and the mixture was stirred for 30 minutes at 60° C. The reaction mixture was concentrated and the residue was dissolved in N,N-dimethylformamide (5 ml), and then added under a nitrogen atmosphere to a mixture of methyl Z-2-hydroxyimino-2-phenylacetate (800 mg), sodium hydride (60% in oil, 178 mg) and N,N-dimethylformamide (5 ml) and the mixture was stirred for 1.5 hours at room temperature. After adding 1N HCl (7 ml) and then aqueous sodium bicarbonate, the mixture was extracted with ethyl acetate. The ethyl acetate layer was washed with saturated aqueous sodium chloride, dried (MgSO₄) and then concentrated. The residue was subjected to column chromatography on silica gel to obtain a colorless oil from a fraction eluted with ethyl acetate-hexane (1:3, v/v). This oil was dissolved in methanol (10 ml)-1N aqueous solution of sodium hydroxide (7 ml) and the mixture was heated under reflux for 1 hour. After adding 1 N HCl (7.5 ml) to the reaction mixture, the mixture was extracted with ethyl acetate. The ethyl acetate layer was washed with saturated aqueous sodium chloride, dried (MgSO₄) and then concentrated. The residual crystal was recrystallized from ethyl acetate-hexane to obtain Z-2-[4-(5-methyl-2-phenyl-4-oxazolylmethoxy)benzyloxyimino]-2-phenylacetic acid (1.07 g, yield 54%) as colorless crystals. m.p. 171–172° C. (decomposition)

Example 2

To a solution of 3-[4-(5-methyl-2-phenyl-4-oxazolylmethoxy)phenyl]propanol (1.00 g) and triethylamine (0.866 ml) in ethyl acetate (30 ml), methanesulfonyl chloride (0.478 ml) was added dropwise at 0° C., and the mixture was stirred for 1 hour. The reaction mixture was washed with saturated aqueous sodium chloride, dried ($MgSO_4$), and then concentrated. The residue was dissolved in N,N-dimethylformamide (10 ml), and methyl Z-2-hydroxyimino-2-phenylacetate (830 mg) and sodium hydride (60%, in oil, 185 mg) were added, and the mixture was stirred for 2 hours at room temperature. After adding 1N HCl (7 ml) and then aqueous sodium bicarbonate, the mixture was extracted with ethyl acetate. The ethyl acetate layer was washed with saturated aqueous sodium chloride, dried ($MgSO_4$) and then concentrated. The residue was subjected to column chromatography on silica gel to obtain a colorless oil from a fraction eluted with ethyl acetate-hexane-toluene (1:5:5, v/v). This oil was dissolved in tetrahydrofuran (10 ml)-methanol (5 ml), and 1N aqueous solution of sodium hydroxide (5 ml) was added, and then the mixture was stirred for 2 hour at 40° C. After adding 1N HCl (5.5 ml) to the reaction mixture, the mixture was extracted with ethyl acetate. The ethyl acetate layer was washed with saturated aqueous sodium chloride, dried ($MgSO_4$) and then concentrated. The residual crystal was recrystallized from ethyl acetate-hexane to obtain Z-2-[3-[4-(5-methyl-2-phenyl-4-oxazolylmethoxy)phenyl]propoxyimino]-2-phenylacetic acid (1.13 g, yield 78%) as colorless crystals. m.p. 165–166° C. (decomposition)

Example 3

To a solution of 4-[2-(methyl-2-pyridylamino)ethoxy]benzylalcohol (1.50 g) in toluene (15 ml), thionyl chloride (0.636 ml) was added at 0° C. and the mixture was stirred for 30 minutes. The reaction mixture was concentrated and the residue was dissolved in N,N-dimethylformamide (10 ml), and then admixed with methyl Z-2-hydroxyimino-2-phenylacetate (1.04 g) and sodium hydride (60% in oil, 511 mg) and stirred for 14 hours at room temperature under nitrogen atmosphere. After adding 1N HCl (20 ml) and then aqueous sodium bicarbonate, the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:2, v/v). This oil was dissolved in tetrahydrofuran (20 ml)-methanol (20 ml), and 1N aqueous solution of sodium hydroxide (10 ml) was added and the mixture was stirred at 40° C. for 1 hour. 1N HCl was added to the reaction mixture to adjust at pH 4, and the mixture was extracted with ethyl acetate. The ethyl acetate layer was washed with saturated aqueous sodium chloride, dried ($MgSO_4$) and then concentrated. The residual crystal was recrystallized from ethyl acetate to obtain Z-2-[4-[2-(methyl-2-pyridylamino)ethoxy]benzyloxyimino]-2-phenylacetic acid (959 mg, yield 41%) as colorless crystals. m.p. 93–94° C.

Example 4

To a solution of 4-[2-(methyl-2-pyridylamino)ethoxy]benzylalcohol (1.50 g) in toluene (15 ml), thionyl chloride (0.636 ml) was added at 0° C. and the mixture was stirred for 30 minutes. The reaction mixture was concentrated and the residue was dissolved in N,N-dimethylformamide (10 ml), and then admixed with methyl E-4-hydroxyimino-2-phenylbutyrate (1.20 g) and sodium hydride (60%, in oil, 511 mg) and stirred for 3 hours at room temperature under nitrogen atmosphere. After adding 1N HCl (20 ml) and then aqueous sodium bicarbonate, the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:2, v/v). This oil was dissolved in tetrahydrofuran (20 ml)-methanol (20 ml), and 1N aqueous solution of sodium hydroxide (10 ml) was added and the mixture was stirred at room temperature for 2 hours. 1N HCl was added to the reaction mixture to adjust at pH 4, and the mixture was extracted with ethyl acetate. The ethyl acetate layer was washed with saturated aqueous sodium chloride, dried ($MgSO_4$) and then concentrated to obtain E-4-[4-[2-(Methyl-2-pyridylamino)ethoxy]benzyloxyimino]-2-phenylbutyric acid (1.04 g, yield 41%) as a colorless oil.

NMR ($CDCl_3$) δ: 2.51–2.62 (2H, m), 3.00–3.09 (2H, m), 3.13 (3H, s), 3.97 (2H, t, J=5.6 Hz), 4.19 (2H, t, J=5.6 Hz), 5.14 (2H, s), 6.50–6.59 (2H, m), 6.87 (2H, d, J=8.8 Hz), 7.24–7.51 (6H, m), 7.59–7.65 (2H, m), 8.13–8.18 (1H, m).

Example 5

Sodium hydride (60%, in oil, 122 mg) was added under a nitrogen atmosphere to a solution of methyl E-2-hydroxyimino-2-phenylacetate (548 mg) and 4-(4-chloromethylphenoxymethyl)-5-methyl-2-phenyloxazole (960 mg) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain a colorless oil from a fraction eluted with ethyl acetate-hexane (1:2, v/v). This oil was dissolved in methanol (5 ml)-1N aqueous solution of sodium hydroxide (5 ml) and the mixture was heated under reflux for 3 hours. 1N HCl (5.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-isopropyl ether to obtain E-2-[4-(5-methyl-2-phenyl-4-oxazolylmethoxy)benzyloxyimino]-2-phenylacetic acid (948 mg, yield 70%) as colorless crystals. m.p. 142–143° C. (decomposition)

Example 6

Sodium hydride (60% in oil, 127 mg) was added under a nitrogen atmosphere to a solution of ethyl E-2-hydroxyimino-3-phenylpropionate (661 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (4 ml) was added and the mixture was stirred at room temperature for 1.5 hours. 1N HCl (4.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-isopropyl ether to obtain E-2-[4-(5-methyl-2-phenyl-4-oxazolylmethoxy)benzyloxyimino]-3-phenylpropionic acid (844 mg, yield 58%) as colorless crystals. m.p. 143–144° C. (decomposition)

Example 7

Sodium hydride (60% in oil, 127 mg) was added under a nitrogen atmosphere to a solution of methyl E-4-hydroxyimino-4-phenylbutyrate (661 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred at room temperature for 1.5 hours. 1N HCl (5.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-hexane to obtain E-4-[4-(5-methyl-2-phenyl-4-oxazolylmethoxy)benzyloxyimino]-4-phenylbutyric acid (907 mg, yield 60%) as colorless crystals. m.p. 126–127° C. (decomposition)

Example 8

Sodium hydride (60% in oil, 127 mg) was added under a nitrogen atmosphere to a solution of ethyl E-2-hydroxyiminohexanoate (553 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:4, v/v). This oil was dissolved in tetrahydrofuran (10 ml)-methanol (5 ml), and 1N aqueous solution of sodium hydroxide (5 ml) was added and the mixture was stirred at room temperature for 30 minutes. 1N HCl (5.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-hexane to obtain E-2-[4-(5-methyl-2-phenyl-4-oxazolylmethoxy)benzyloxyimino]hexanoic acid (922 mg, yield 68%) as colorless crystals. m.p. 112–114° C.

Example 9

Sodium hydride (60% in oil, 127 mg) was added under a nitrogen atmosphere to a solution of ethyl E-2-hydroxyiminopropionate (418 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred at room temperature for 1 hour. 1N HCl (5.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-isopropylether to obtain E-2-[4-(5-methyl-2-phenyl-4-oxazolylmethoxy)benzyloxyimino]propionic acid (849 mg, yield 70%) as colorless crystals. m.p. 147–148° C.

Example 10

Sodium hydride (60% in oil, 127 mg) was added under a nitrogen atmosphere to a solution of ethyl Z-2-(4-bromophenyl)-2-hydroxyiminoacetate (868 mg) and 4-(4-chloromethylphenoxymethyl)-5-methyl-2-phenyloxazole (100 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:2, v/v). This oil was dissolved in tetrahydrofuran (5 ml)-methanol (10 ml), and 0.5N aqueous solution of sodium hydroxide (10 ml) was added and the mixture was heated under reflux for 1.5 hours. 1N HCl (5.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate to obtain Z-2-(4-bromophenyl)-2-[4-(5-methyl-2-phenyl-4-oxazolylmethoxy)benzyloxyimino]acetic acid (1.34 g, yield 81%) as colorless crystals. m.p. 189–190° C. (decomposition)

Example 11

Sodium hydride (60% in oil, 127 mg) was added under a nitrogen atmosphere to a solution of ethyl Z-2-hydroxyimino-2-(4-phenoxylphenyl)acetate (910 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried ($MgSO_4$) and then concentrated. The residue was subjected to column chromatography on silica gel to obtain an oil from a fraction eluted with ethyl acetate-hexane (1:3, v/v). This oil was dissolved in tetrahydrofuran (20 ml)-methanol (10 ml), and 1N aqueous solution of sodium hydroxide (10 ml) was added and the mixture was stirred at 40° C. for 2 hours. 1N HCl (10.5 ml) was added to the reaction mixture, and the mixture was extracted with ethyl acetate. The ethyl acetate layer was washed with saturated aqueous sodium chloride, dried ($MgSO_4$) and then concentrated. The residual crystal was recrystallized from ethyl acetate-hexane to obtain Z-2-[4-(5-methyl-2-phenyl-4-oxazolylmethoxy)benzyloxyimino]-2-(4-phenoxyphenyl)acetic acid (1.51 g, yield 89%) as colorless crystals. m.p. 184–185° C. (decomposition)

Example 12

Sodium hydride (60% in oil, 127 mg) was added under a nitrogen atmosphere to a solution of ethyl E-2-hydroxyimino-2-(4-phenoxylphenyl)acetate (910 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred at 40° C. for 2 hours. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-2-[4-(5-methyl-2-phenyl-4-oxazolylmethoxy)benzyloxyimino]-2-(4-phenoxyphenyl)acetic acid (1.38 g, yield 81%) as colorless crystals. m.p. 152–153° C. (decomposition)

Example 13

Sodium hydride (60% in oil, 107 mg) was added under a nitrogen atmosphere to a solution of methyl Z-2-hydroxyimino-2-(3-phenoxylphenyl)acetate (605 mg) and 4-(4-chloromethylphenoxymethyl)-5-methyl-2-phenyloxazole (700 mg) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred at 40° C. for 2 hours. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain Z-2-[4-(5-methyl-2-phenyl-4-oxazolylmethoxy)benzyloxyimino]-2-(3-phenoxyphenyl)acetic acid (738 mg, yield 62%) as colorless crystals. m.p.: 173–174° C. (decomposition)

Example 14

Sodium hydride (60% in oil, 107 mg) was added under a nitrogen atmosphere to a solution of methyl E-2-hydroxyimino-2-(3-phenoxylphenyl)acetate (605 mg) and 4-(4-chloromethylphenoxymethyl)-5-methyl-2-phenyloxazole (700 mg) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred at 40° C. for 2 hours. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-2-[4-(5-methyl-2-phenyl-4-oxazolylmethoxy)benzyloxyimino]-2-(3-phenoxyphenyl)acetic acid (745 mg, yield 62%) as a colorless amorphous material. m.p. 55–65° C.

NMR (CDCl$_3$) δ: 2.45 (3H, s), 5.10 (2H, s), 5.22 (2H, s), 6.98–7.48 (16H, m), 7.98–8.05 (2H, m).

Example 15

Sodium hydride (60% in oil, 209 mg) was added under a nitrogen atmosphere to a solution of ethyl Z-2-(4-fluorophenyl)-2-hydroxyiminoacetate (920 mg) and 4-(4-chloromethylphenoxymethyl)-5-methyl-2-phenyloxazole (1.37 g) in N,N-dimethylformamide-(10 ml) at room temperature and the mixture was stirred for 1 hour. After adding 1N HCl (7 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (20 ml)-methanol (10 ml), and 1N aqueous solution of sodium hydroxide (10 ml) was added and the mixture was stirred at 40° C. for 2 hours. 1N HCl (10.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate to obtain Z-2-(4-fluorophenyl)-2-[4-(5-methyl-2-phenyl-4-oxazolylmethoxy)benzyloxyimino]acetic acid (1.66 g, yield 83%) as colorless crystals. m.p. 182–183° C. (decomposition)

Example 16

Sodium hydride (60% in oil, 209 mg) was added under a nitrogen atmosphere to a solution of ethyl E-2-(4-fluorophenyl)-2-hydroxyiminoacetate (920 mg) and 4-(4-chloromethylphenoxymethyl)-5-methyl-2-phenyloxazole (1.37 g) in N,N-dimethylformamide (10 ml) at room temperature and the mixture was stirred for 1 hour. After adding 1N HCl (7 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (20 ml)-methanol (10 ml), and 1N aqueous solution of sodium hydroxide (10 ml) was added and the mixture was stirred at 40° C. for 2 hours. 1N HCl (10.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate to obtain E-2-(4-fluorophenyl)-2-[4-(5-methyl-2-phenyl-4-oxazolylmethoxy)benzyloxyimino]acetic acid (1.08 g, yield 54%) as colorless crystals. m.p. 150–151° C. (decomposition)

Example 17

Sodium hydride (60% in oil, 153 mg) was added under a nitrogen atmosphere to a solution of ethyl E-4-(4- fluorophenyl)-4-hydroxyiminobutyrate (763 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (7 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:4, v/v). This oil was dissolved in tetrahydrofuran (20 ml)-methanol (10 ml), and 1N aqueous solution of sodium hydroxide (10 ml) was added and the mixture was stirred at room temperature for 1 hour. 1N HCl (7.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-4-(4-fluorophenyl)-4-[4-(5-methyl-2-phenyl-4-oxazolylmethoxy)benzyloxyimino] butyric acid (727 mg, yield 47%) as colorless crystals. m.p. 139–140° C.

Example 18

Sodium hydride (60% in oil, 153 mg) was added under a nitrogen atmosphere to a solution of ethyl E-5-hydroxyimino-5-phenylpentanoate (751 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain an oil from a fraction eluted with ethyl acetate-hexane (1:4, v/v). This oil was dissolved in tetrahydrofuran (20 ml)-methanol (10 ml), and 1N aqueous solution of sodium hydroxide (10 ml) was added and the mixture was stirred at room temperature for 2 hours. 1N HCl (10.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-5-[4-(5-methyl-2-phenyl-4-oxazolylmethoxy)benzyloxyimino]-5-phenylpentanoic acid (1.24 g, yield 80%) as colorless crystals. m.p. 129–130° C.

Example 19

Sodium hydride (60% in oil, 127 mg) was added under a nitrogen atmosphere to a solution of ethyl Z-2-hydroxyimino-2-(4-methoxyphenyl)acetate (711 mg) and 4-(4-chloromethylphenoxymethyl)-5-methyl-2-phenyloxazole (1.00 g) in N,N-dimethylformamide (10 ml) at room temperature and the mixture was stirred for 1 hour. After adding 1N HCl (5 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain ethyl Z-2-(4-methoxyphenyl)-2-[4-(5-methyl-2-phenyl-4-oxazolylmethoxy) benzyloxyimino]acetate (1.50 g, yield: 94%) as crystals from a fraction eluted with ethyl acetate-hexane (1:2, v/v). Recrystallization was performed from ethyl acetate-hexane. m.p. 102–103° C.

Example 20

Sodium hydride (60% in oil, 225 mg) was added under a nitrogen atmosphere to a solution of ethyl 2-hydroxyimino-3-methylbutyrate (Z:E=2.3:1, 1.01 g) and 4-(4-chloromethylphenoxymethyl)-5-methyl-2-phenyloxazole (2.00 g) in N,N-dimethylformamide (20 ml) at room temperature and the mixture was stirred for 1 hour. After adding 1N HCl (10 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain as a first product ethyl Z-3-methyl-2-[4-(5-methyl-2-phenyl-4-oxazolylmethoxy)benzyloxyimino] butyrate (640 mg, yield 23%) as a colorless oil from a fraction eluted with ethyl acetate-hexane-dichloromethane (1:10:10, v/v).

NMR (CDCl$_3$) δ: 1.14 (6H, d, J=6.8 Hz), 1.28 (3H, t, J=7.1 Hz), 2.43 (3H, s), 2.70 (1H, sept, J=6.8 Hz), 4.29 (2H, q, J=7.1 Hz), 4.99 (2H, s), 5.03 (2H, s), 6.98 (2H, d, J=8.8 Hz), 7.27 (2H, d, J=8.8 Hz), 7.41–7.49 (3H, m), 7.97–8.05 (2H, m).

Example 21

From a fraction eluted following the Z-form in Example 20, ethyl E-3-methyl-2-[4-(5-methyl-2-phenyl-4-oxazolylmethoxy)benzyloxyimino]butyrate (1.34 g, yield 48%) as a colorless oil.

NMR (CDCl$_3$) δ: 1.17 (6H, d, J=7.0 Hz), 1.35 (3H, t, J=7.1 Hz), 2.44 (3H, s), 3.40 (1H, sept, J=7.0 Hz), 4.30 (2H, q, J=7.1 Hz), 5.00 (2H, s), 5.17 (2H, s), 7.01 (2H, d, J=8.8 Hz), 7.32 (2H, d, J=8.8 Hz), 7.40–7.48 (3H, m), 7.97–8.05 (2H, m).

Example 22

Sodium hydride (60% in oil, 225 mg) was added under a nitrogen atmosphere to a solution of ethyl E-2-(4-bromophenyl)-2-hydroxyiminoacetate (1.73 g) and 4-(4-chloromethylphenoxymethyl)-5-methyl-2-phenyloxazole (2.00 g) in N,N-dimethylformamide (20 ml) at room temperature and the mixture was stirred for 1 hour. After adding 1N HCl (10 ml), aqueous sodium bicarbonate was added, and then the mixture was extracted with ethyl-acetate. The ethyl acetate layer was washed with saturated aqueous sodium chloride, dried (MgSO$_4$) and then concentrated. The residue was subjected to column chromatography on silica gel to obtain ethyl E-2-(4-bromophenyl)-2-[4-(5-methyl-2-phenyl-4-oxazolylmethoxy)benzyloxyimino]acetate (2.54 g, yield 73%) as crystals from a fraction eluted with ethyl acetate-hexane (1:3, v/v). Recrystallization was performed from ethyl acetate-hexane. m.p. 105–106° C.

Example 23

Sodium hydride (60% in oil, 368 mg) was added under a nitrogen atmosphere to a solution of ethyl Z-2-(4-bromophenyl)-2-hydroxyiminoacetate (2.50 g) and 4-(4-chloromethylphenoxymethyl)-5-methyl-2-phenyloxazole (3.03 g) in N,N-dimethylformamide (25 ml) at room temperature and the mixture was stirred for 1 hour. After adding 1N HCl (12 ml), aqueous sodium bicarbonate was added, and then the mixture was extracted with ethyl acetate. The ethyl acetate layer was washed with saturated aqueous sodium chloride, dried (MgSO$_4$) and then concentrated. The residue was subjected to column chromatography on silica gel to obtain ethyl Z-2-(4-bromophenyl)-2-[4-(5-methyl-2- phenyl-4-oxazolylmethoxy)benzyloxyimino]acetate (3.12 g, yield 61%) as a colorless oil from a fraction eluted with ethyl acetate-hexane (1:3, v/v).

NMR (CDCl$_3$) δ: 1.33 (3H, t, J=7.1 Hz), 2.43 (3H, s), 4.40 (2H, q, J=7.1 Hz), 5.00 (2H, s), 5.19 (2H, s), 7.01 (2H, d, J=8.6 Hz), 7.32 (2H, d, J=8.6 Hz), 7.37–7.54 (7H, m), 7.97–8.05 (2H, m).

Example 24

Ethyl Z-2-(4-methoxyphenyl)-2-[4-(5-methyl-2-phenyl-4-oxazolylmethoxy)benzyloxyimino]acetate (1.20 g) was dissolved in tetrahydrofuran (5 ml)-methanol (10 ml), and 0.5N aqueous solution of sodium hydroxide (10 ml) was added and the mixture was heated under reflux for 1 hour. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate to obtain Z-2-(4-methoxyphenyl)-2-[4-(5-methyl-2-phenyl-4-oxazolylmethoxy)benzyloxyimino]acetic acid (1.02 g, yield 90%) as colorless crystals. m.p. 183–184° C.

Example 25

Ethyl Z-3-methyl-2-[4-(5-methyl-2-phenyl-4-oxazolylmethoxy)benzyloxyimino]butyrate (580 mg) was dissolved in tetrahydrofuran (6 ml)-methanol (3 ml), and 1N aqueous solution of sodium hydroxide (3 ml) was added and the mixture was stirred for 3 hours at room temperature. 1N HCl (3.3 ml) was added to the reaction mixture, and the mixture was extracted with ethyl acetate. The ethyl acetate layer was washed with saturated aqueous sodium chloride, dried (MgSO$_4$) and then concentrated. The residual crystals were recrystallized from ethyl acetate-hexane to obtain Z-3-methyl-2-[4-(5-methyl-2-phenyl-4-oxazolylmethoxy)benzyloxyimino]butyric acid (523 mg, yield 96%) as colorless crystals. m.p. 140–142° C.

Example 26

Ethyl E-3-methyl-2-[4-(5-methyl-2-phenyl-4-oxazolylmethoxy)benzyloxyimino]butyrate (1.27 g) was dissolved in tetrahydrofuran (10 ml)-methanol (5 ml), and 1N aqueous solution of sodium hydroxide (5 ml) was added and the mixture was stirred for 2 hours at room temperature. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-3-methyl-2-[4-(5-methyl-2-phenyl-4-oxazolylmethoxy)benzyloxyimino]butyric acid (1.02 g, yield: 85%) as colorless crystals. m.p. 128–129° C.

Example 27

Ethyl E-2-(4-bromophenyl)-2-[4-(5-methyl-2-phenyl-4-oxazolylmethoxy)benzyloxyimino]acetate (600 mg) was dissolved in tetrahydrofuran (6 ml)-methanol (3 ml), and 1N aqueous solution of sodium hydroxide (3 ml) was added and the mixture was stirred for 1 hour at 40° C. 1N HCl (3.3 ml) was added to the reaction mixture, and the mixture was extracted with ethyl acetate. The ethyl acetate layer was washed with saturated aqueous sodium chloride, dried (MgSO$_4$) and then concentrated. The residual crystals were recrystallized from ethyl acetate to obtain E-2-(4-bromophenyl)-2-[4-(5-methyl-2-phenyl-4-oxazolylmethoxy)benzyloxyimino]acetic acid (516 mg, yield 99%) as colorless crystals. m.p. 159–160° C. (decomposition)

Example 28

A mixture of ethyl E-2-(4-bromophenyl)-2-[4-(5-methyl-2-phenyl-4-oxazolylmethoxy)benzyloxyimino]acetate (800 mg), phenylboronic acid (213 mg), potassium carbonate (604 mg), toluene (20 ml), ethanol (2 ml) and water (2 ml) was stirred under an argon atmosphere for 30 minutes at room temperature. Tetrakis (triphenylphosphine)palladium (0) (101 mg) was added and the mixture was heated under reflux for 15 hours. The reaction mixture was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (6 ml)-methanol (3 ml), and 1N aqueous solution of sodium hydroxide (3 ml) was added and the mixture was stirred for 2 hours at 40° C. 1N HCl (3.3 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain E-2-(4-biphenyl)-2-[4-(5-methyl-2-phenyl-4-oxazolylmethoxy)benzyloxyimino]acetic acid (642 mg, yield 85%) as colorless crystals. m.p. 148–149° C. (decomposition)

Example 29

A mixture of ethyl Z-2-(4-bromophenyl)-2-[4-(5-methyl-2-phenyl-4-oxazolylmethoxy)benzyloxyimino]acetate (1.43 g), phenylboronic acid (476 mg), potassium carbonate (1.44 g), toluene (30 ml), ethanol (3 ml) and water (3 ml) was stirred under an argon atmosphere for 30 minutes at room temperature. Tetrakis (triphenylphosphine)palladium (0) (180 mg) was added and the mixture was heated under reflux for 13 hours. The reaction mixture was washed with saturated aqueous sodium chloride, dried (MgSO$_4$) and then concentrated. The residue was subjected to column chromatography on silica gel to obtain an oil from a fraction eluted with ethyl acetate-hexane-dichloromethane (1:10:10, v/v). This oil was dissolved in tetrahydrofuran (10 ml)-methanol (5 ml), and 1N aqueous solution of sodium hydroxide (5 ml) was added and the mixture was stirred for 2 hours at 40° C. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-isopropylether to obtain Z-2-(4-biphenyl)-2-[4-(5-methyl-2-phenyl-4-oxazolylmethoxy)benzyloxyimino]acetic acid (807 mg, yield 60%) as colorless crystals. m.p. 193–194° C. (decomposition)

Example 30

A mixture of ethyl Z-2-(4-bromophenyl)-2-[4-(5-methyl-2-phenyl-4-oxazolylmethoxy)benzyloxyimino]acetate (800 mg), 3-thienylboronic acid (224 mg), potassium carbonate (604 mg), toluene (20 ml), ethanol (2 ml) and water (2 ml) was stirred under an argon atmosphere for 30 minutes at room temperature. Tetrakis (triphenylphosphine)palladium (0) (101 mg) was added and the mixture was heated under reflux for 14 hours. The reaction mixture was washed with saturated aqueous sodium chloride, dried (MgSO$_4$) and then concentrated. The residue was subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred for 2 hours at 40° C. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain Z-2-[4-(5-methyl-2-phenyl-4-oxazolylmethoxy)benzyloxyimino]-2-[4-(3-thienyl)phenyl]acetic acid (442 mg, yield 58%) as pale-yellow crystals. m.p. 205–206° C. (decomposition)

Example 31

A mixture of ethyl Z-2-(4-bromophenyl)-2-[4-(5-methyl-2-phenyl-4-oxazolylmethoxy)benzyloxyimino]acetate (830 mg), 4-(E-2-phenylethenyl)phenylboronic acid (268 mg), potassium carbonate (626 mg), toluene (20 ml), ethanol (2 ml) and water (2 ml) was stirred under an argon atmosphere for 30 minutes at room temperature. Tetrakis(triphenylphosphine)palladium (0) (105 mg) was added and the mixture was heated under reflux for 14 hours. The reaction mixture was washed with saturated aqueous sodium chloride, dried (MgSO$_4$) and then concentrated. The residues were subjected to column chromatography on silica gel to obtain an oil from a fraction eluted with ethyl acetate-hexane (1:3, v/v). This oil was dissolved in tetrahydrofuran (10 ml)-methanol (5 ml), and 1N aqueous solution of sodium hydroxide (5 ml) was added and the mixture was stirred for 2 hours at 40° C. 1N HCl (5.5 ml) was added to the reaction mixture, and the mixture was extracted with ethyl acetate. The ethyl acetate layer was washed with saturated aqueous sodium chloride, dried (MgSO$_4$) and then concentrated. The residual crystal was recrystallized from ethyl acetate-hexane to obtain Z-2-[4-(5-methyl-2-phenyl-4-oxazolylmethoxy)benzyloxyimino]-2-[4-(E-2-phenylethenyl)phenyl]acetic acid (634 mg, yield: 77%) as pale-yellow crystals. m.p. 194–195° C. (decomposition)

Example 32

Sodium hydride (60% in oil, 153 mg) was added to a solution of ethyl Z-2-hydroxyimino-2-(3-pyridyl)acetate (619 mg) and 4-(4-chloromethylphenoxymethyl)-5-methyl-2-phenyloxazole (1.00 g) in N,N-dimethylformamide (10 ml) at room temperature under nitrogen atmosphere and stirred for 3 hours. 1N hydrochloric acid (7 ml) was added, an aqueous saturated solution of sodium bicarbonate was added and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-[4-(5-methyl-2-phenyl-4-oxazolylmethoxy)benzyloxyimino]-2-(3-pyridyl)acetate (1.12 g, yield 74%) as a pale-yellow oil from an ethyl acetate-hexane (1:1, v/v)-eluted fraction.

NMR (CDCl$_3$) δ: 1.35 (3H, t, J=7.1 Hz), 2.44 (3H, s), 4.42 (2H, q, J=7.1 Hz), 5.00 (2H, s), 5.22 (2H, s), 7.01 (2H, d, J=8.8 Hz), 7.25–7.37 (3H, m), 7.40–7.48 (3H, m), 7.86–7.93 (1H, m), 7.99–8.05 (2H, m), 8.61–8.65 (1H, m), 8.75–8.78 (1H, m).

Example 33

Sodium hydride (60%, in oil, 153 mg) was added to a solution of ethyl E-2-hydroxyimino-2-(3-pyridyl)acetate (619 mg) and 4-(4-chloromethylphenoxymethyl)-5-methyl-2-phenyloxazole (1.00 g) in N,N-dimethylformamide (10 ml) at room temperature under nitrogen atmosphere and stirred for 3 hours. 1N hydrochloric acid (7 ml) was added, an aqueous saturated solution of sodium bicarbonate was added and extracted with ethyl acetate. The ethyl acetate layer was washed with an aqueous saturated solution of sodium chloride, dried (MgSO$_4$) and concentrated. The residue was subjected to silica gel chromatography to obtain ethyl E-2-[4-(5-methyl-2-phenyl-4-oxazolylmethoxy)benzyloxyimino]-2-(3-pyridyl)acetate (1.02 g, yield 68%) as a pale-yellow oil from an ethyl acetate-hexane (1:1, v/v)-eluted fraction.

NMR (CDCl$_3$) δ: 1.36 (3H, t, J=7.1 Hz), 2.44 (3H, s), 4.37 (2H, q, J=7.1 Hz), 4.99 (2H, s), 5.27 (2H, s), 7.00 (2H, d, J=8.8 Hz), 7.25–7.38 (3H, m), 7.41–7.48 (3H, m), 7.72–7.80 (1H, m), 7.98–8.05 (2H, m), 8.57–8.62 (1H, m), 8.66–8.70 (1H, m).

Example 34 m-Chloroperoxybenzoic acid (70%, 282 mg) was added to a solution of ethyl-Z-2-[4-(5-methyl-2-phenyl-4-oxazolylmethoxy)benzyloxyimino]-2-(3-pyridyl)acetate (450 mg) in tetrahydrofuran (10 ml) at room temperature and stirred for 17 hours. An aqueous saturated solution of sodium thiosulfate (10 ml) and an aqueous saturated solution of potassium carbonate (10 ml) were added and extracted with ethyl acetate. The ethyl acetate layer was washed with an aqueous saturated solution of sodium chloride, dried (MgSO$_4$) and concentrated. The residue was subjected to silica gel chromatography to obtain an oil from an ethyl acetate-methanol (10:1, v/v)-eluted fraction. This was dissolved in tetrahydrofuran (10 ml)-methanol (5 ml), 1N an aqueous saturated solution of sodium hydroxide (5 ml) was added and stirred at 40° C. for 2 hours. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from acetone-diisopropyl ether to obtain Z-2-[4-(5-methyl-2-phenyl-4-oxazolylmethoxy)benzyloxyimino]-2-(pyridine-1-oxide-3-yl)acetic acid (282 mg, yield 64%) as colorless crystals. m.p. 181–182° C. (decomposition)

Example 35

A 1N aqueous saturated solution of sodium hydroxide (5 ml) was added to a solution of ethyl Z-2-[4-(5-methyl-2-phenyl-4-oxazolylmethoxy)benzyloxyimino]-2-(3-pyridyl)acetate (520 mg) in tetrahydrofuran (10 ml)-methanol (5 ml) and stirred at 40° C. for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate to obtain Z-2-[4-(5-methyl-2-phenyl-4-oxazolylmethoxy)benzyloxyimino]-2-(3-pyridyl)acetic acid (321 mg, yield 66%) as colorless crystals. m.p. 156–157° C. (decomposition)

Example 36 m-Chloroperoxybenzoic acid (70%, 282 mg) was added to a solution of ethyl E-2-[4-(5-methyl-2-phenyl-4-oxazolylmethoxy)benzyloxyimino]-2-(3-pyridyl)acetate (450 mg) in tetrahydrofuran (10 ml) at room temperature and stirred for 17 hours. An aqueous saturated solution of sodium thiosulfate (10 ml) and an aqueous saturated solution of potassium carbonate (10 ml) were added and extracted with ethyl acetate. The ethyl acetate layer was washed with an aqueous saturated solution of sodium chloride, dried (MgSO$_4$) and concentrated. The residue was subjected to silica gel chromatography to obtain an oil from an ethyl acetate-methanol (10:1, v/v)-eluted fraction. This was dissolved in tetrahydrofuran (10 ml)-methanol (5 ml), a 1N aqueous saturated solution of sodium hydroxide (5 ml) was added and stirred at 40° C. for 2 hours. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-2-[4-(5-methyl-2-phenyl-4-oxazolylmethoxy)benzyloxyimino]-2-(pyridine-1-oxide-3-yl)acetic acid (228 mg, yield 52%) as colorless crystals. m.p. 161–162° C. (decomposition)

Example 37

A 1N aqueous saturated solution of sodium hydroxide (5 ml) was added to a solution of ethyl E-2-[4-(5-methyl-2-phenyl-4-oxazolylmethoxy)benzyloxyimino]-2-(3-pyridyl)acetate (520 mg) in tetrahydrofuran (10 ml)-methanol (5 ml) and stirred at 40° C. for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from acetone-diisopropyl ether to obtain E-2-[4-(5-methyl-2-phenyl-4-oxazolylmethoxy)benzyloxyimino]-2-(3-pyridyl)acetic acid (427 mg, yield 88%) as colorless crystals. m.p. 130–131° C. (decomposition)

Example 38

Sodium hydride (60%, in oil, 203 mg) was added to a solution of ethyl Z-2-(3-bromophenyl)-2-hydroxyiminoacetate (1.15 g) and 4-(4-chloromethylphenoxymethyl)-5-methyl-2-phenyloxazole (1.33 g) in N,N-dimethylformamide (15 ml) at room temperature under nitrogen atmosphere and stirred for 1 hour. 1N hydrochloric acid (7 ml) was added, an aqueous saturated solution of sodium bicarbonate was added and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-(3-bromophenyl)-2-[4-(5-methyl-2-phenyl-4-oxazolylmethoxy)benzyloxyimino]acetate (1.12 g, yield 48%) as a pale-yellow oil from an ethyl acetate-hexane (1:4, v/v)-eluted fraction.

NMR (CDCl$_3$) δ: 1.33 (3H, t, J=7.1 Hz), 2.44 (3H, s), 4.41 (2H, q, J=7.1 Hz), 5.00 (2H, s), 5.20 (2H, s), 7.01 (2H, d, J=8.8 Hz), 7.20–7.56 (8H, m), 7.73–7.76 (1H, m), 7.99–8.06 (2H, m).

Example 39

Sodium hydride (60% in oil, 399 mg) was added to a solution of ethyl Z-2-(3-benzoylphenyl)-2-hydroxyiminoacetate (2.47 g) and 4-(4-chloromethylphenoxymethyl)-5-methyl-2-phenyloxazole (2.61 g) in N,N-dimethylformamide (15 ml) at room temperature under nitrogen atmosphere and stirred for 1 hour. 1N hydrochloric acid (15 ml) was added, an aqueous saturated solution of sodium bicarbonate was added and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-(3-benzoylphenyl)-2-[4-(5-methyl-2-phenyl-4-oxazolylmethoxy)benzyloxyimino]acetate (1.97 g, yield 41%) as a pale-yellow oil from an ethyl acetate-hexane (1:3, v/v)-eluted fraction.

NMR (CDCl$_3$) δ: 1.31 (3H, t, J=7.1 Hz), 2.43 (3H, s), 4.40 (2H, q, J=7.1 Hz), 4.99 (2H, s), 5.20 (2H, s), 7.00 (2H, d, J=8.8 Hz), 7.25–7.72 (11H, m), 7.76–7.86 (3H, m), 7.96–8.05 (2H, m).

Example 40

A 1N aqueous saturated solution of sodium hydroxide (7 ml) was added to a solution of ethyl Z-2-(3-benzoylphenyl)-2-[4-(5-methyl-2-phenyl-4-oxazolylmethoxy)benzyloxyimino]acetate (800 mg) in tetrahydrofuran (14 ml)-methanol (7 ml) and stirred at 40° C. for 1 hour. 1N hydrochloric acid (7.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain Z-2-(3-benzoylphenyl)-2-[4-(5-methyl-2-phenyl-4-oxazolylmethoxy)benzyloxyimino]acetic acid (608 mg, yield 80%) as orange crystals. m.p. 185–186° C. (decomposition)

Example 41

Potassium tert-butoxide (328 mg) was added to a mixture of methyltriphenylphosphonium bromide (1.14 g) and tetrahydrofuran (10 ml) under nitrogen atmosphere and stirred at room temperature for 1 hour. A solution of ethyl Z-2-(3-benzoylphenyl)-2-[4-(5-methyl-2-phenyl-4-oxazolylmethoxy)benzyloxyimino]acetate (1.12 g) in tetrahydrofuran (10 ml) was added dropwise, stirred further for 3 hours, dilute hydrochloric acid was added and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2-[4-(5-methyl-2-phenyl-4-oxazolylmethoxy)benzyloxyimino]-2-[3-(1-phenylvinyl)phenyl]acetate (880 mg, yield 79%) as a pale brown oil from an ethyl acetate-hexane (1:4, v/v)-eluted fraction.

NMR (CDCl$_3$) δ: 1.27 (3H, t, J=7.1 Hz), 2.43 (3H, s), 4.36 (2H, q, J=7.1 Hz), 4.99 (2H, s), 5.18 (2H, s), 5.48 (2H, d, J=6.4 Hz), 6.99 (2H, d, J=8.6 Hz), 7.25–7.55 (14H, m), 7.99–8.05 (2H, m).

Example 42

A mixture of ethyl Z-2-(3-bromophenyl)-2-[4-(5-methyl-2-phenyl-4-oxazolylmethoxy)benzyloxyimino]acetate (780 mg), E-styrylboronic acid (252 mg), potassium carbonate (589 mg), toluene (20 ml), water (2 ml) and ethanol (2 ml) was stirred at room temperature for 30 minutes under argon atmosphere. To this was added tetrakis (triphenylphosphine) palladium (0) (98 mg) and heated to reflux for 15 hours. After the reaction mixture was cooled to room temperature, the organic layer was washed with an aqueous saturated solution of sodium chloride, dried (MgSO$_4$) and concentrated. The residue was subjected to silica gel chromatography to obtain ethyl Z-2-[4-(5-methyl-2-phenyl-4-oxazolylmethoxy)benzyloxyimino]-2-(E-3-styryl)acetate (6.0 mg, yield 75%) as pale brown oil from an ethyl acetate-hexane (1:4, v/v)-eluted fraction.

NMR (CDCl$_3$) δ: 1.35 (3H, t, J=7.1 Hz), 2.43 (3H, s), 4.43 (2H, q, J=7.1 Hz), 5.00 (2H, s), 5.23 (2H, s), 7.01 (2H, d,

J=8.4 Hz), 7.11 (2H, s), 7.25–7.60 (13H, m), 7.69 (1H, br s), 7.99–8.05 (2H, m).

Example 43

A 1N aqueous saturated solution of sodium hydroxide (5 ml) was added to a solution of ethyl Z-2-(3-bromophenyl)-2-[4-(5-methyl-2-phenyl-4-oxazolylmethoxy)benzyloxyimino]acetate (430 mg) in tetrahydrofuran (10 ml)-methanol (5 ml) and stirred at 40° C. for 2 hours. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain Z-2-(3-bromophenyl)-2-[4-(5-methyl-2-phenyl-4-oxazolylmethoxy)benzyloxyimino]acetic acid (370 mg, yield 91%) as colorless crystals. m.p. 181–182° C. (decomposition)

Example 44

A 1N aqueous saturated solution of sodium hydroxide (5 ml) was added to a solution of ethyl Z-2-[4-(5-methyl-2-phenyl-4-oxazolylmethoxy)benzyloxyimino]-2-[3-(1-phenylvinyl)phenyl]acetate (780 mg) in tetrahydrofuran (10 ml)-methanol (5 ml) and stirred at 40° C. for 2 hours. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain Z-2-[4-(5-methyl-2-phenyl-4-oxazolylmethoxy)benzyloxyimino]-2-[3-(i-phenylvinyl)phenyl]acetic acid (701 mg, yield 95%) as colorless crystals. m.p. 171–172° C.

Example 45

A 1N aqueous saturated solution of sodium hydroxide (5 ml) was added to a solution of ethyl Z-2-[4-(5-methyl-2-phenyl-4-oxazolylmethoxy)benzyloxyimino]-2-(E-3-styryl)acetate (500 mg) in tetrahydrofuran (10 ml)-methanol (5 ml) and stirred at 40° C. for 2 hours. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain Z-2-[4-(5-methyl-2-phenyl-4-oxazolylmethoxy)benzyloxyimino]-2-(E-3-styryl)acetic acid (474 mg, yield 95%) as colorless crystals. m.p. 178–179° C.

Example 46

Sodium hydride (60% in oil, 211 mg) was added to a solution of ethyl E-4-(hydroxyimino)-4-(4-phenoxyphenyl)butyrate(1.50 g) and 4-(4-chloromethylphenoxymethyl)-5-methyl-2-phenyloxazole (1.50 g) in N,N-dimethylformamide (15 ml) at room temperature under nitrogen atmosphere and stirred for 1 hour. 1N hydrochloric acid (7 ml) was added, an aqueous saturated solution of sodium bicarbonate was added and extracted with ethyl acetate. The ethyl acetate layer was washed with an aqueous saturated solution of sodium chloride, dried ($MgSO_4$) and concentrated. The residue was subjected to silica gel chromatography to obtain crystals from an ethyl acetate-hexane (1:4, v/v)-eluted fraction. The crystals were recrystallized from ethyl acetate-hexane to obtain ethyl E-4-[4-(5-methyl-2-phenyl-4-oxazolylmethoxy)benzyloxyimino]-4-(4-phenoxyphenyl)butyrate (1.87 g, yield 66%) as colorless crystals. m.p. 118–119° C.

Example 47

A 1N aqueous saturated solution of sodium hydroxide (10 ml) was added to a solution of ethyl E-4-[4-(5-methyl-2-phenyl-4-oxazolylmethoxy)benzyloxyimino]-4-(4-phenoxyphenyl)butyrate(1.60 g) in tetrahydrofuran (20 ml)-methanol (10 ml) and stirred at room temperature for 1 hour. 1N hydrochloric acid (10.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain E-4-[4-(5-methyl-2-phenyl-4-oxazolylmethoxy)benzyloxyimino]-4-(4-phenoxyphenyl)butyric acid (1.50 g, yield 99%) as colorless crystals. m.p. 131–132° C.

Example 48

Sodium hydride (60% in oil, 134 mg) was added to a solution of methyl E-4-(hydroxyimino)-4-phenylbutyrate (632 mg) and 4-[2-(4-chloromethylphenoxy)ethyl]-5-methyl-2-phenyloxazole (1.00 g) in N,N-dimethylformamide (10 ml) at room temperature under nitrogen atmosphere and stirred for 1 hour. 1N hydrochloric acid (5 ml) was added, an aqueous saturated solution of sodium bicarbonate was added and extracted with ethyl acetate. The ethyl acetate layer was washed with an aqueous saturated solution of sodium chloride, dried ($MgSO_4$) and concentrated. The residue was subjected to silica gel chromatography to obtain crystals from an ethyl acetate-hexane (1:3, v/v)-eluted fraction. The crystals were recrystallized from ethyl acetate-hexane to obtain methyl E-4-[4-[2-(5-methyl-2-phenyl-4-oxazolyl)ethoxy]benzyloxyimino]-4-phenylbutyrate (650 mg, yield 43%) as colorless crystals. m.p. 73–74° C.

Example 49

Thionyl chloride (0.633 ml) was added dropwise to a solution of 4-[2-(methyl-2-pyrimidylamino)ethoxy]benzylalcohol (1.50 g) in toluene (25 ml) at 0° C., which was stirred for 30 minutes and concentrated. The residue was dissolved in N,N-dimethylformamide (10 ml), methyl E-4-(hydroxyimino)-4-phenylbutyrate (1.20 g) was added, sodium hydride (60% in oil, 509 mg) was further added at room temperature under nitrogen atmosphere and stirred for 1 hour. 1N hydrochloric acid (20 ml) was added to the reaction mixture, an aqueous saturated solution of sodium bicarbonate and extracted with ethyl acetate. The ethyl acetate layer was washed with an aqueous saturated solution of sodium chloride, dried ($MgSO_4$) and concentrated. The residue was subjected to silica gel chromatography to obtain methyl E-4-[4-[2-(methyl-2-pyrimidylamino)ethoxy]benzyloxyimino]-4-phenylbutyrate (1.32 g, yield 51%) as a dark red oil from an ethyl acetate-hexane (1:2, v/v)-eluted fraction.

NMR ($CDCl_3$) δ: 2.49–2.58 (2H, m), 3.00–3.09 (2H, m), 3.30 (3H, s), 3.62 (3H, s), 4.02 (2H, t, J=5.7 Hz), 4.21 (2H, t, J=5.7 Hz), 5.14 (2H, s), 6.48 (1H, t, J=4.8 Hz), 6.90 (2H, d, J=8.4 Hz), 7.29–7.38 (5H, m), 7.59–7.65 (2H, m), 8.31 (2H, d, J=4.8 Hz).

Example 50

A 1N aqueous saturated solution of sodium hydroxide (5 ml) was added to a solution of methyl E-4-[4-[2-(5-methyl- 2-phenyl-4-oxazolyl)ethoxy]benzyloxyimino]-4-phenylbutyrate (460 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-[2-(5-methyl-2-phenyl-4-oxazolyl)ethoxy]benzyloxyimino]-4-phenylbutyric acid (443 mg, yield 99%) as colorless crystals. m.p. 106–107° C.

Example 51

A 1N aqueous saturated solution of sodium hydroxide (5 ml) was added to a solution of methyl E-4-[4-[2-(methyl-2-pyrimidylamino)ethoxy]benzyloxyimino]-4-phenylbutyrate (1.22 g) in tetrahydrofuran (10 ml)-methanol (5 ml) and stirred at room temperature for 1 hour. 1N hydrochloric acid (5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-[2-(methyl-2-pyrimidylamino)ethoxy]benzyloxyimino]-4-phenylbutyric acid (1.09 g, yield 92%) as colorless crystals. m.p. 72–73° C.

Example 52

A mixture of 4-(5-methyl-2-phenyl-4-oxazolylmethoxy)benzyloxyamine (1.00 g), ethyl benzoylacetate (0.612 ml), acetic acid (0.554 ml), sodium acetate (528 mg) and ethanol (20 ml) was heated to reflux for 12 hours and cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-3-[4-(5-methyl-2-phenyl-4-oxazolylmethoxy)benzyloxyimino]-3-phenylpropionate (1.29 g, yield 83%) as a colorless oil from an ethyl acetate-hexane (1:3, v/v).

NMR (CDCl$_3$) δ: 1.15 (3H, t, J=7.1 Hz), 2.44 (3H, s), 3.76 (2H, s), 4.09 (2H, q, J=7.1 Hz), 5.00 (2H, s), 5.20 (2H, s), 7.01 (2H, d, J=8.4 Hz), 7.30–7.50 (8H, m), 7.61–7.67 (2H, m), 7.97–8.05 (2H, m).

Example 53

Lithium hydroxide monohydrate (402 mg) was added to a solution of ethyl E-3-[4-(5-methyl-2-phenyl-4-oxazolylmethoxy)benzyloxyimino]-3-phenylpropionate (1.16 g) in tetrahydrofuran (60 ml)-water (40 ml) and stirred at room temperature for 18 hours. Dilute hydrochloric acid was added to the reaction mixture and extracted with ethyl acetate. The ethyl acetate layer was washed with an aqueous saturated solution of sodium chloride, dried (MgSO$_4$) and concentrated. The residue was recrystallized to obtain 3-[4-(5-methyl-2-phenyl-4-oxazolylmethoxy)benzyloxyimino]-3-phenylpropionic acid (1.08 g, yield 99%) as colorless crystals. m.p. 107–108° C.

Example 54

Sodium hydride (60%, in oil, 143 mg) was added to a solution of methyl E-4-(hydroxyimino)-4-phenylbutyrate (676 mg) and 5-chloro-2-(4-chloromethylphenoxymethyl)imidazo[1,2-a]pyridine (1.00 g) in N,N-dimethylformamide (10 ml) at room temperature and stirred for 1 hour. 1N hydrochloric acid (7 ml) was added, an aqueous saturated solution of sodium bicarbonate was added and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-[4-(5-chloroimidazo[1,2-a]pyridin-2-ylmethoxy)benzyloxyimino]-4-phenylbutyrate (1.04 g, yield 67%) as a colorless oil from an ethyl acetate-hexane (2:1, v/v)-eluted fraction.

NMR (CDCl$_3$) δ: 2.50–2.60 (2H, m), 3.01–3.11 (2H, m), 3.62 (3H, s), 5.17 (2H, s), 5.31 (2H, s), 6.90 (1H, d, J=7.4 Hz), 7.04 (2H, d, J=8.6 Hz), 7.19 (1H, dd, J=7.4, 8.8 Hz), 7.30–7.39 (5H, m), 7.55–7.66 (3H, m), 7.85 (1H, s).

Example 55

A 1N aqueous saturated solution of sodium hydroxide (5 ml) was added to a solution of methyl E-4-[4-(5-chloroimidazo[1,2-a]pyridin-2-ylmethoxy)benzyloxyimino]-4-phenylbutyrate (400 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-chloroimidazo[1,2-a]pyridin-2-ylmethoxy)benzyloxyimino]-4-phenylbutyric acid (313 mg, yield 78%) as colorless crystals. m.p. 160–161° C.

Example 56

A mixture of methyl E-4-[4-(5-chloroimidazo[1,2-a]pyridin-2-ylmethoxy)benzyloxyimino]-4-phenylbutyrate (550 mg), phenylboronic acid (168 mg), sodium bicarbonate (348 mg), toluene (20 ml), water (2 ml) and methanol (2 ml) was stirred at room temperature for 30 minutes under argon atmosphere. To this was added tetrakis(triphenylphosphine)palladium (0) (80 mg) and heated to reflux for 36 hours. The reaction mixture was cooled to room temperature, the organic layer was washed with an aqueous saturated solution of sodium chloride, dried (MgSO$_4$) and concentrated. The residue was subjected to silica gel chromatography to obtain methyl E-4-[4-(5-phenylimidazo[1,2-a]pyridin-2-ylmethoxy)benzyloxyimino]-4-phenylbutyrate (490 mg, yield 82%) as a colorless oil from an ethyl acetate-hexane (3:2, v/v)-eluted fraction.

NMR (CDCl$_3$) δ: 2.49–2.58 (2H, m), 3.00–3.10 (2H, m), 3.61 (3H, s), 5.15 (2H, s), 5.24 (2H, s), 6.75 (1H, d, J=7.0 Hz), 7.01 (2H, d, J=8.8 Hz), 7.24–7.37 (6H, m), 7.51–7.63 (8H, m), 7.72 (1H, s).

Example 57

A 1N aqueous saturated solution of sodium hydroxide (5 ml) was added to a solution of methyl E-4-[4-(5-phenylimidazo[1,2-a]pyridin-2-ylmethoxy)benzyloxyimino]-4-phenylbutyrate (400 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-phenylimidazo[1,2-a]pyridin-2-ylmethoxy)benzyloxyimino]-4-phenylbutyric acid (365 mg, yield 94%) as colorless crystals. m.p. 160–161° C.

Example 58

After a mixture of 4-(5-methyl-2-phenyl-4-oxazolylmethoxy)benzyloxyamine (500 mg), ethyl 6-oxo-6-phenylhexanoate (415 mg), acetic acid (0.276 ml), sodium acetate (264 mg) and ethanol (20 ml) was heated to reflux for 13 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-[4-(5-methyl-2-phenyl-4-oxazolylmethoxy)benzyloxyimino]-6-phenylhexanoate (620 mg, yield 73%) as a colorless oil from an ethyl acetate-hexane (1:4, v/v)-eluted fraction.

NMR (CDCl$_3$) δ: 1.22 (3H, t, J=7.1 Hz), 1.45–1.73 (4H, m), 2.28 (2H, t, J=7.3 Hz), 2.44 (3H, s), 2.78 (2H, t, J=7.5 Hz), 4.09 (2H, q, J=7.1 Hz), 5.00 (2H, s), 5.15 (2H, s), 7.01 (2H, d, J=8.4 Hz), 7.33–7.48 (8H, m), 7.58–7.64 (2H, m), 7.99–8.05 (2H, m).

Example 59

Ethyl Z-6-[4-(5-methyl-2-phenyl-4-oxazolylmethoxy)benzyloxyimino]-6-phenylhexanoate (120 mg, yield 14%) was obtained as a colorless oil from a fraction which eluted following the E-compound in Example 58.

NMR (CDCl$_3$) δ: 1.22 (3H, t, J=7.1 Hz), 1.38–1.71 (4H, m), 2.26 (2H, t, J=7.3 Hz), 2.43 (3H, s), 2.53 (2H, t, J=7.5 Hz), 4.09 (2H, q, J=7.1 Hz), 4.99 (2H, s), 5.02 (2H, s), 6.97 (2H, d, J=8.4 Hz), 7.23–7.47 (10H, m), 7.97–8.05 (2H, m).

Example 60

A 1N aqueous saturated solution of sodium hydroxide (3 ml) was added to a solution of ethyl E-6-[4-(5-methyl-2-phenyl-4-oxazolylmethoxy)benzyloxyimino]-6-phenylhexanoate (530 mg) in tetrahydrofuran (6 ml)-methanol (3 ml) and stirred at room temperature for 1 hour. 1N hydrochloric acid (3.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-6-[4-(5-methyl-2-phenyl-4-oxazolylmethoxy)benzyloxyimino]-6-phenylhexanoic acid (451 mg, yield 90%) as colorless crystals. m.p. 112–113° C.

Example 61

A 1N aqueous saturated solution of sodium hydroxide (3 ml) was added to a solution of ethyl Z-6-[4-(5-methyl-2-phenyl-4-oxazolylmethoxy)benzyloxyimino]-6-phenylhexanoate (120 mg) in tetrahydrofuran (6 ml)-methanol (3 ml) and stirred at room temperature for 1 hour. 1N hydrochloric acid (3.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain Z-6-[4-(5-methyl-2-phenyl-4-oxazolylmethoxy)benzyloxyimino]-6-phenylhexanoic acid (113 mg, yield 99%) as colorless crystals. m.p. 101–102° C.

Example 62

After a mixture of 4-(5-methyl-2-phenyl-4-oxazolylmethoxy)benzyloxyamine (500 mg), 3-oxo-1-indancarboxylic acid (284 mg), acetic acid (0.276 ml), sodium acetate (264 mg) and ethanol (20 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-3-[4-(5-methyl-2-phenyl-4-oxazolylmethoxy)benzyloxyimino]-1-indancarboxylic acid (522 mg, yield 69%) as colorless crystals. m.p. 148–149° C.

Example 63

After a mixture of 4-(5-methyl-2-phenyl-4-oxazolylmethoxy)benzyloxyamine (500 mg), ethyl 4-oxo-4-(2-pyridyl)butyrate (367 mg), acetic acid (0.276 ml), sodium acetate (264 mg) and ethanol (20 ml) was heated to reflux for 20 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-4-[4-(5-methyl-2-phenyl-4-oxazolylmethoxy)benzyloxyimino]-4-(2-pyridyl)butyrate (600 mg, yield 75%) as a colorless oil from an ethyl acetate-hexane (2:7, v/v)-eluted fraction.

NMR (CDCl$_3$) δ: 1.23 (3H, t, J=7.1 Hz), 2.44 (3H, s), 2.55–2.64 (2H, m), 3.19–3.28 (2H, m), 4.07 (2H, q, J=7.1 Hz), 5.00 (2H, s), 5.19 (2H, s), 7.01 (2H, d, J=8.8 Hz), 7.19–7.24 (1H, m), 7.36 (2H, d, J=8.8 Hz), 7.39–7.46 (3H, m), 7.64 (1H, dt, J=1.8, 7.6 Hz), 7.87 (1H, d, J=8.0 Hz), 7.99–8.05 (2H, m), 8.54–8.59 (1H, m).

Example 64

A 1N aqueous saturated solution of sodium hydroxide (5 ml) was added to a solution of ethyl E-4-[4-(5-methyl-2-phenyl-4-oxazolylmethoxy)benzyloxyimino]-4-(2-pyridyl)butyrate (520 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-methyl-2-phenyl-4-oxazolylmethoxy)benzyloxyimino]-4-(2-pyridyl)butyric acid (425 mg, yield 87%) as colorless crystals. m.p. 116–117° C.

Example 65

After a mixture of 4-(5-methyl-2-phenyl-4-oxazolylmethoxy)benzyloxyamine (500 mg), ethyl 4-(2-furyl)-4-oxobutyrate (347 mg), acetic acid (0.276 ml), sodium acetate (264 mg) and ethanol (20 ml) was heated to reflux for 96 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-4-(2-furyl)-4-[4-(5-methyl-2-phenyl-4-oxazolylmethoxy)benzyloxyimino]butyrate (190 mg, yield 24%) as a colorless oil from an ethyl acetate-hexane (1:4, v/v)-eluted fraction.

NMR (CDCl$_3$) δ: 1.25 (3H, t, J=7.1 Hz), 2.44 (3H, s), 2.62–2.71 (2H, m), 2.95–3.04 (2H, m), 4.13 (2H, q, J=7.1 Hz), 5.00 (2H, s), 5.14 (2H, s), 6.45–6.49 (1H, m), 7.01 (2H, d, J=8.8 Hz), 7.25–7.28 (1H, m), 7.34 (2H, d, J=8.8 Hz), 7.39–7.48 (4H, m), 7.99–8.05 (2H, m).

Example 66

Ethyl Z-4-(2-furyl)-4-[4-(5-methyl-2-phenyl-4-oxazolylmethoxy)benzyloxyimino]butyrate (510 mg, yield 65%) was obtained as a colorless oil from a fraction which eluted following the E-compound in Example 65.

NMR (CDCl$_3$) δ: 1.21 (3H, t, J=7.11 Hz), 2.43 (3H, s), 2.53–2.62 (2H, m), 2.89–2.98 (2H, m), 4.09 (2H, q, J=7.1 Hz), 5.00 (2H, s), 5.17 (2H, s), 6.43 (1H, dd, J=1.8, 3.2 Hz), 6.68 (1H, d, J=1.8 Hz), 7.01 (2H, d, J=8.8 Hz), 7.34 (2H, d, J=8.8 Hz), 7.38–7.47 (4H, m), 7.97–8.05 (2H, m).

Example 67

After a mixture of 4-(5-methyl-2-phenyl-4-oxazolylmethoxy)benzyloxyamine (500 mg), ethyl 4-oxo-4-(3-pyridyl)butyrate (367 mg), acetic acid (0.276 ml), sodium acetate (264 mg) and ethanol (20 ml) was heated to reflux for 20 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl 4-[4-(5-methyl-2-phenyl-4-oxazolylmethoxy)benzyloxyimino]-4-(3-pyridyl)butyrate (590 mg, yield 73%) as a colorless oil from an ethyl acetate-hexane (3:2, v/v)-eluted fraction.

NMR (CDCl$_3$) δ: 1.16–1.30 (3H, m), 2.44 (3H, s), 2.51–2.64 (2H, m), 2.86 (0.4H, t, J=6.9 Hz), 3.05 (1.6H, t, J=7.9 Hz), 4.02–4.18 (2H, m), 5.00 (2.4H, s like), 5.18 (1.6H, s), 6.95–7.06 (2H, m), 7.23–7.48 (6H, m), 7.71–7.78 (0.2H, m), 7.91–8.05 (2.8H, m), 8.53–8.61 (1H, m), 8.66–8.69 (0.2H, m), 8.85–8.88 (0.8H, m).

Example 68

A 1N aqueous saturated solution of sodium hydroxide (5 ml) was added to a solution of ethyl Z-4-(2-furyl)-4-[4-(5-methyl-2-phenyl-4-oxazolylmethoxy)benzyloxyimino]butyrate (460 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain Z-4-(2-furyl)-4-[4-(5-methyl-2-phenyl-4-oxazolylmethoxy)benzyloxyimino]butyric acid (402 mg, yield 93%) as colorless crystals. m.p. 131–133° C.

Example 69

After a mixture of 4-(5-methyl-2-phenyl-4-oxazolylmethoxy)benzyloxyamine (500 mg), ethyl 4-oxo-4-(4-pyridyl)butyrate (367 mg), acetic acid (0.276 ml), sodium acetate (264 mg) and ethanol (20 ml) was heated to reflux for 15 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl 4-[4-(5-methyl-2-phenyl-4-oxazolylmethoxy)benzyloxyimino]-4-(4-pyridyl)butyrate (740 mg, yield 92%) as a colorless oil from an ethyl acetate-hexane (3:2, v/v)-eluted fraction.

NMR (CDCl$_3$) δ: 1.16–1.31 (3H, m), 2.44 (3H, s), 2.48–4.63 (2H, m), 2.77–2.86 (0.5H, m), 3.02 (1.5H, t, J=7.9 Hz), 4.02–4.18 (2H, m), 5.00 (2.5H, s like), 5.20 (1.5H, s), 6.95–7.22 (2H, m), 7.20–7.56 (7H, m), 7.99–8.05 (2H, m), 8.59–8.66 (2H, m).

Example 70

A 1N aqueous saturated solution of sodium hydroxide (5 ml) was added to a solution of ethyl 4-[4-(5-methyl-2-phenyl-4-oxazolylmethoxy)benzyloxyimino]-4-(3-pyridyl)butyrate (520 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-methyl-2-phenyl-4-oxazolylmethoxy)benzyloxyimino]-4-(3-pyridyl)butyric acid (378 mg, yield 77%) as colorless crystals. m.p. 158–159° C.

Example 71

A 1N aqueous saturated solution of sodium hydroxide (5 ml) was added to a solution of ethyl 4-[4-(5-methyl-2-phenyl-4-oxazolylmethoxy)benzyloxyimino]-4-(4-pyridyl)butyrate (670 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-methyl-2-phenyl-4-oxazolylmethoxy)benzyloxyimino]-4-(4-pyridyl)butyric acid (475 mg, yield 75%) as colorless crystals. m.p. 161–162° C.

Example 72

A 1N aqueous saturated solution of sodium hydroxide (5 ml) was added to a solution of ethyl E-4-(2-furyl)-4-[4-(5-methyl-2-phenyl-4-oxazolylmethoxy)benzyloxyimino]butyrate (190 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-(2-furyl)-4-[4-(5-methyl-2-phenyl-4-oxazolylmethoxy)benzyloxyimino]butyric acid (140 mg, yield 78%) as colorless crystals. m.p. 124–125° C.

Example 73

After a mixture of 4-(5-methyl-2-phenyl-4-oxazolylmethoxy)benzyloxyamine (500 mg), methyl 9-oxo-9-phenylnonanoate (464 mg), 1N hydrochloric acid (3 ml), sodium acetate (264 mg) and methanol (20 ml) was heated to reflux for 72 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain an oil from an ethyl acetate-hexane (1:6, v/v)-eluted fraction. This was dissolved in tetrahydrofuran (10 ml)-methanol (5 ml), a 1N aqueous saturated solution of sodium hydroxide (5 ml) was added and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-9-[4-

(5-methyl-2-phenyl-4-oxazolylmethoxy)benzyloxyimino]-9-phenylnonanoic acid (323 mg, yield 37%) as colorless crystals. m.p. 67–68° C.

Example 74

After a mixture of 3-(5-methyl-2-phenyl-4-oxazolylmethoxy)benzyloxyamine (600 mg), methyl 4-oxo-4-phenylbutyrate (371 mg), acetic acid (0.331 ml), sodium acetate (317 mg) and methanol (20 ml) was heated to reflux for 40 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain methyl E-4-[3-(5-methyl-2-phenyl-4-oxazolylmethoxy)benzyloxyimino]-4-phenylbutyrate (570 mg, yield 61%) as a colorless oil from an ethyl acetate-hexane (1:4, v/v)-eluted fraction.

NMR ($CDCl_3$) δ: 2.43 (3H, s), 2.53–2.62 (2H, m), 3.04–3.13 (2H, m), 3.62 (3H, s), 5.01 (2H, s), 5.22 (2H, s), 6.94–7.08 (3H, m), 7.28–7.48 (7H, m), 7.60–7.66 (2H, m), 7.97–8.05 (2H, m).

Example 75

After a mixture of 3-(5-methyl-2-phenyl-4-oxazolylmethoxy)benzyloxyamine (600 mg), ethyl 6-oxo-6-phenylhexanoate (452 mg), acetic acid (0.331 ml), sodium acetate (317 mg) and ethanol (20 ml) was heated to reflux for 15 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl E-6-[3-(5-methyl-2-phenyl-4-oxazolylmethoxy)benzyloxyimino]-6-phenylhexanoate (590 mg, yield 58%) as a colorless oil from an ethyl acetate-hexane (2:9, v/v)-eluted fraction.

NMR ($CDCl_3$) δ: 1.21 (3H, t, J=7.1 Hz), 1.47–1.80 (4H, m), 2.29 (2H, t, J=7.5 Hz), 2.43 (3H, s), 2.80 (2H, t, J=7.5 Hz), 4.08 (2H, q, J=7.1 Hz), 5.01 (2H, s), 5.20 (2H, s), 6.93–7.08 (3H, m), 7.25–7.47 (7H, m), 7.58–7.64 (2H, m), 7.97–8.05 (2H, m).

Example 76

A 1N aqueous saturated solution of sodium hydroxide (5 ml) was added to a solution of ethyl E-6-[3-(5-methyl-2-phenyl-4-oxazolylmethoxy)benzyloxyimino]-6-phenylhexanoate (520 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain E-6-[3-(5-methyl-2-phenyl-4-oxazolylmethoxy)benzyloxyimino]-6-phenylhexanoic acid (432 mg, yield 88%) as colorless crystals. m.p. 114–115° C.

Example 77

A 1N aqueous saturated solution of sodium hydroxide (5 ml) was added to a solution of methyl E-4-[3-(5-methyl-2-phenyl-4-oxazolylmethoxy)benzyloxyimino]-4-phenylbutyrate (500 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain E-4-[3-(5-methyl-2-phenyl-4-oxazolylmethoxy)benzyloxyimino]-4-phenylbutyric acid (395 mg, yield 82%) as colorless crystals. m.p. 108–109° C.

Example 78

After a mixture of 4-(5-methyl-2-phenyl-4-oxazolylmethoxy)benzyloxyamine (600 mg), ethyl 7-oxo-7-phenylheptanoate (959 mg), acetic acid (0.331 ml), sodium acetate (317 mg) and ethanol (20 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl E-7-[4-(5-methyl-2-phenyl-4-oxazolylmethoxy)benzyloxyimino]-7-phenylheptanoate (800 mg, yield 72%) as a colorless oil from an ethyl acetate-hexane (1:5, v/v)-eluted fraction.

NMR ($CDCl_3$) δ: 1.08–1.70 (9H, m), 2.24 (2H, t, J=7.5 Hz), 2.44 (3H, s), 2.76 (2H, t, J=7.5 Hz), 4.11 (2H, q, J=7.1 Hz), 5.00 (2H, s), 5.15 (2H, s), 7.02 (2H, d, J=8.8 Hz), 7.33–7.48 (8H, m), 7.57–7.63 (2H, m), 7.99–8.05 (2H, m).

Example 79

After a mixture of 4-(5-methyl-2-phenyl-4-oxazolylmethoxy)benzyloxyamine (1.50 g), ethyl 8-oxo-8-phenyloctanoate (2.54 g), acetic acid (0.830 ml), sodium acetate (793 mg) and ethanol (40 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain ethyl E-8-[4-(5-methyl-2-phenyl-4-oxazolylmethoxy)benzyloxyimino]-8-phenyloctanoate (2.02 g, yield 76%) as a colorless oil from an ethyl acetate-hexane (1:5, v/v)-eluted fraction.

NMR ($CDCl_3$) δ: 1.18–1.65 (11H, m), 2.25 (2H, t, J=7.5 Hz), 2.44 (3H, s), 2.75 (2H, t, J=7.5 Hz), 4.12 (2H, q, J=7.1 Hz), 5.00 (2H, s), 5.15 (2H, s), 7.01 (2H, d, J=8.8 Hz), 7.33–7.46 (8H, m), 7.58–7.64 (2H, m), 7.99–8.05 (2H, m).

Example 80

Ethyl Z-8-[4-(5-methyl-2-phenyl-4-oxazolylmethoxy)benzyloxyimino]-8-phenyloctanoate (408 mg, yield 15%) was obtained as a colorless oil from a fraction which eluted following the E-compound in Example 79.

NMR ($CDCl_3$) δ: 1.20–1.65 (11H, m), 2.25 (2H, t, J=7.5 Hz), 2.43 (3H, s), 2.50 (2H, t, J=7.2 Hz), 4.12 (2H, q, J=7.1 Hz), 4.99 (2H, s), 5.02 (2H, s), 6.97 (2H, d, J=8.6 Hz), 7.25 (2H, d, J=8.6 Hz), 7.27–7.48 (8H, m), 7.99–8.04 (2H, m).

Example 81

A 1N aqueous saturated solution of sodium hydroxide (5 ml) was added to a solution of ethyl E-8-[4-(5-methyl-2-phenyl-4-oxazolylmethoxy)benzyloxyimino]-8-phenyloctanoate (660 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-[4-(5-methyl-2-phenyl-4-oxazolylmethoxy) benzyloxyimino]-8-phenyloctanoic acid (580 mg, yield 92%) as colorless crystals. m.p. 116–117° C.

Example 82

After a mixture of 4-(5-methyl-2-phenyl-4-oxazolylmethoxy)benzyloxyamine (600 mg), 6-oxo-6-phenylhexanamide (396 mg), acetic acid (0.331 ml), sodium acetate (317 mg) and ethanol (20 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain crystals from an ethyl acetate-hexane (3:1, v/v)-eluted fraction. The crystals were recrystallized from ethyl acetate-hexane to obtain E-6-[4-(5-methyl-2-phenyl-4-oxazolylmethoxy)benzyloxyimino]-6-phenylhexanamide (651 mg, yield 68%) as colorless crystals. m.p. 95–96° C.

Example 83

A mixture of 4-(chloromethyl)-2-(2-furyl)-5-methyloxazole (340 mg), ethyl E-8-(4-hydroxybenzyloxyimino)-8-phenyloctanoate (600 mg), potassium carbonate (432 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-8-[4-[2-(2-furyl)-5-methyl-4-oxazolylmethoxy]benzyloxyimino]-8-phenyloctanoate (717 mg, yield 84%) as a colorless oil from an ethyl acetate-hexane (2:9, v/v)-eluted fraction.

NMR (CDCl$_3$) δ: 1.20–1.65 (11H, m), 2.25 (2H, t, J=7.5 Hz), 2.42 (3H, s), 2.70–2.79 (2H, m), 4.11 (2H, q, J=7.1 Hz), 5.00 (2H, s), 5.15 (2H, s), 6.51–6.54 (1H, m), 6.96–7.03 (3H, m), 7.31–7.40 (5H, m), 7.53–7.56 (1H, m), 7.58–7.64 (2H, m).

Example 84

After a mixture of 4-(5-methyl-2-phenyl-4-oxazolylmethoxy)benzyloxyamine (1.00 g), methyl 4-oxo-4-phenylbutyrate (619 mg), acetic acid (0.553 ml), sodium acetate (528 mg) and methanol (20 ml) was heated to reflux for 19 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-[4-(5-methyl-2-phenyl-4-oxazolylmethoxy)benzyloxyimino]-4-phenylbutyrate (1.18 g, yield 76%) as a colorless oil from an ethyl acetate-hexane (2:9, v/v)-eluted fraction.

NMR (CDCl$_3$) δ: 2.44 (3H, s), 2.50–2.60 (2H, m), 3.02–3.11 (2H, m), 3.62 (3H, s), 5.01 (2H, s), 5.17 (2H, s), 7.01 (2H, d, J=8.8 Hz), 7.33–7.48 (8H, m), 7.60–7.66 (2H, m), 7.99–8.06 (2H, m).

Example 85

Methyl Z-4-[4-(5-methyl-2-phenyl-4-oxazolylmethoxy) benzyloxyimino]-4-phenylbutyrate (222 mg, yield 14%) was obtained as a colorless oil from a fraction which eluted following the E-compound in Example 84.

NMR (CDCl$_3$) δ: 2.43 (3H, s), 2.57 (2H, t, J=7.0 Hz), 2.84 (2H, t, J=7.0 Hz), 3.62 (3H, s), 5.00 (4H, s like), 6.98 (2H, d, J=8.8 Hz), 7.26 (2H, d, J=8.8 Hz), 7.30–7.48 (8H, m), 7.99–8.05 (2H, m).

Example 86

A mixture of 5-(chloromethyl)-3-phenylisoxazole (238 mg), methyl E-4-(4-hydroxybenzyloxyimino)-4-phenylbutyrate (350 mg), potassium carbonate (310 mg) and N,N-dimethylformamide (10 ml) was stirred at room temperature for 13 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-phenyl-4-[4-(3-phenyl-5-isoxazolylmethoxy) benzyloxyimino]butyrate (358 mg, yield 62%) as a colorless oil from an ethyl acetate-hexane (1:4, v/v)-eluted fraction.

NMR (CDCl$_3$) δ: 2.50–2.60 (2H, m), 3.02–3.11 (2H, m), 3.62 (3H, s), 5.17 (2H, s), 5.22 (2H, s), 6.66 (1H, s), 6.99 (2H, d, J=8.8 Hz), 7.34–7.49 (8H, m), 7.59–7.65 (2H, m), 7.78–7.84 (2H, m).

Example 87

Lithium hydroxide monohydrate (58.3 mg) was added to a solution of methyl E-4-phenyl-4-[4-(3-phenyl-5-isoxazolylmethoxy)benzyloxyimino]butyrate (326 mg) in tetrahydrofuran (6 ml)-water (4 ml) and stirred at room temperature for 2 hours. 1N hydrochloric acid (1.4 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-phenyl-4-[4-(3-phenyl-5-isoxazolylmethoxy)benzyloxyimino]butyric acid (306 mg, yield 97%) as colorless crystals. m.p. 96–97° C.

Example 88

A mixture of 3-(chloromethyl)-5-phenylisoxazole (340 mg), methyl E-4-(4-hydroxybenzyloxyimino)-4-phenylbutyrate (500 mg), potassium carbonate (442 mg) and N,N-dimethylformamide (10 ml) was stirred at room temperature for 72 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-phenyl-4-[4-(5-phenyl-3-isoxazolylmethoxy) benzyloxyimino]butyrate (472 mg, yield 63%) as a colorless oil from an ethyl acetate-hexane (2:9, v/v)-eluted fraction.

NMR (CDCl$_3$) δ: 2.50–2.59 (2H, m), 3.01–3.11 (2H, m), 3.62 (3H, s), 5.16 (2H, s), 5.21 (2H, s), 6.66 (1H, s), 7.01 (2H, d, J=8.8 Hz), 7.34–7.53 (8H, m), 7.57–7.65 (2H, m), 7.74–7.82 (2H, m).

Example 89

A mixture of 4-(chloromethyl)-5-methyl-2-phenylthiazol (394 mg), methy E-4-(4-hydroxybenzyloxyimino)-4-phenylbutyrate (500 mg), potassium carbonate (442 mg) and N,N-dimethylormamide (10 ml) was stirred at room temperature for 72 hours. Water was added to the reaction mixture and extracted with ethyl acetate. The ethyl acetate layer was subjected to silica gel chromatography to obtain methy E-4-[4-(5-methyl-2-phenyl-4-thiazolylmethoxy) benzyloxyimino]-4-phenylbutyrate (570 mg, yield 71%) as a colorless oil from an ethyl acetate-hexane (1:5, v/v)-eluted fraction.

NMR (CDCl$_3$) δ: 2.50–2.60 (5H, m), 3.02–3.11 (2H, m), 3.62 (3H, s), 5.17 (2H, s), 5.18 (2H, s), 7.04 (2H, d, J=8.6 Hz), 7.33–7.51 (8H, m), 7.58–7.66 (2H, m), 7.85–7.93 (2H, m).

Example 90

Lithium hydroxide monohydrate (73.5 mg) was added to a solution of methyl E-4-phenyl-4-[4-(5-phenyl-3-isoxazolylmethoxy)benzyloxyimino]butyrate (412 mg) in tetrahydrofuran (6 ml)-water (4 ml)-methanol (4 ml) and stirred at room temperature for 2 hours. 1N hydrochloric acid (1.8 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-phenyl-4-[4-(5-phenyl-3-isoxazolylmethoxy) benzyloxyimino]butyric acid (320 mg, yield 80%) as colorless crystals. m.p. 100–101° C.

Example 91

Lithium hydroxide monohydrate (83.6 mg) was added to a solution of methyl E-4-[4-(5-methyl-2-phenyl-4-thiazolylmethoxy)benzyloxyimino]-4-phenylbutyrate (500 mg) in tetrahydrofuran (10 ml)-water (4 ml)-methanol (8 ml) and stirred at room temperature for 2 hours. 1N hydrochloric acid (2.1 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(5-methyl-2-phenyl-4-thiazolylmethoxy)benzyloxyimino]-4-phenylbutyric acid (363 mg, yield 75%) as colorless crystals. m.p. 99–100° C.

Example 92

A mixture of 4-(chloromethyl)-2-(2-furyl)-5-methyloxazole (348 mg), methyl E-4-(4-hydroxybenzyloxyimino)-4-phenylbutyrate (500 mg), potassium carbonate (442 mg) and N,N-dimethylformamide (10 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-[4-[2-(2-furyl)-5-methyl-4-oxazolylmethoxy]benzyloxyimino]-4-phenylbutyrate (507 mg, yield 67%) as a colorless oil from an ethyl acetate-hexane (1:3, v/v)-eluted fraction.

NMR (CDCl$_3$) δ: 2.42 (3H, s), 2.50–2.59 (2H, m), 3.01–3.11 (2H, m), 3.62 (3H, s), 5.00 (2H, s), 5.16 (2H, s), 6.51–6.54 (1H, m), 6.95–7.02 (3H, m), 7.28–7.40 (5H, m), 7.52–7.55 (1H, m), 7.59–7.66 (2H, m).

Example 93

A mixture of 4-(chloromethyl)-5-methyl-2-(2-thienyl) oxazole (376 mg), methyl E-4-[(4-hydroxybenzyloxy) imino]-4-phenylbutyrate (500 mg), potassium carbonate (442 mg) and N,N-dimethylformamide (10 ml) was stirred at room temperature for 40 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-[4-[5-methyl-2-(2-thenyl)-4-oxazolylmethoxy] benzyloxyimino]-4-phenylbutyrate (495 mg, yield 63%) as a colorless oil from an ethyl acetate-hexane (1:5, v/v)-eluted fraction.

NMR (CDCl$_3$) δ: 2.41 (3H, s), 2.50–2.60 (2H, m), 3.02–3.11 (2H, m), 3.63 (3H, s), 4.98 (2H, s), 5.16 (2H, s), 6.99 (2H, d, J=8.8 Hz), 7.10 (1H, dd, J=3.6, 5.0 Hz), 7.32–7.42 (6H, m), 7.59–7.66 (3H, m).

Example 94

Lithium hydroxide monohydrate (76.0 mg) was added to a solution of methyl E-4-[4-[2-(2-furyl)-5-methyl-4-oxazolylmethoxy]benzyloxyimino]-4-phenylbutyrate (430 mg) in tetrahydrofuran (6 ml)-water (4 ml)-methanol (4 ml) and stirred at room temperature for 2 hours. 1N hydrochloric acid (1.9 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-[2-(2-furyl)-5-methyl-4-oxazolylmethoxy] benzyloxyimino]-4-phenylbutyric acid (328 mg, yield 79%) as colorless crystals. m.p. 124–125° C.

Example 95

A mixture of 4-(chloromethyl)-5-methyl-2-(2-thienyl) oxazole (368 mg), ethyl E-8-(4-hydroxybenzyloxyimino)-8-phenyloctanoate (600 mg), potassium carbonate (432 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-8-[4-[5-methyl-2-(2-thienyl)-4-oxazolylmethoxy] benzyloxyimino]-8-phenyloctanoate (762 mg, yield 95%) as a colorless oil from an ethyl acetate-hexane (1:5, v/v)-eluted fraction.

NMR (CDCl$_3$) δ: 1.20–1.65 (11H, m), 2.25 (2H, t, J=7.3 Hz), 2.41 (3H, s), 2.70–2.79 (2H, m), 4.11 (2H, q, J=7.1 Hz), 4.98 (2H, s), 5.15 (2H, s), 6.99 (2H, d, J=8.8 Hz), 7.07–7.12 (1H, m), 7.30–7.42 (6H, m), 7.58–7.65 (3H, m).

Example 96

A mixture of benzyl bromide (0.209 ml), methyl E-4-(4-hydroxybenzyloxyimino)-4-phenylbutyrate (500 mg), potassium carbonate (442 mg) and N,N-dimethylformamide (10 ml) was stirred at room temperature for 15 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-(4-benzoloxybenzyloxyimino)-4-phenylbutyrate (400 mg, yield 62%) as a colorless oil from an ethyl acetate-hexane (1:7, v/v)-eluted fraction.

NMR (CDCl$_3$) δ: 2.50–2.59 (2H, m), 3.01–3.10 (2H, m), 3.62 (3H, s), 5.07 (2H, s), 5.15 (2H, s), 6.97 (2H, d, J=8.8 Hz), 7.30–7.46 (10H, m), 7.60–7.66 (2H, m).

Example 97

Lithium hydroxide monohydrate (73.6 mg) was added to a solution of methyl E-4-[4-[5-methyl-2-(2-thienyl)-4- oxazolylmethoxy]benzyloxyimino]-4-phenylbutyrate (430 mg) in tetrahydrofuran (6 ml)-water (4 ml)-methanol (4 ml) and stirred at room temperature for 2 hours. 1N hydrochloric acid (1.8 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-[5-methyl-2-(2-thienyl)-4-oxazolylmethoxy] benzyloxyimino]-4-phenylbutyric acid (366 mg, yield 88%) as colorless crystals. m.p. 142–143° C.

Example 98

Lithium hydroxide monohydrate (70.7 mg) was added to a solution of methyl E-4-(4-benzyloxybenzyloxyimino)-4-phenylbutyrate (340 mg) in tetrahydrofuran (6 ml)-water (4 ml)-methanol (4 ml) and stirred at room temperature for 2 hours. 1N hydrochloric acid (1.8 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-(4-benzyloxybenzyloxyimino)-4-phenylbutyric acid (238 mg, yield 72%) as colorless crystals. m.p. 86–87° C.

Example 99

A mixture of 2-chloromethylimidazo[1,2-a]pyridine (293 mg), methyl E-4-(4-hydroxybenzyloxyimino)-4-phenylbutyrate (500 mg), potassium carbonate (442 mg) and N,N-dimethylformamide (10 ml) was stirred at room temperature for 17 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-[4-(imidazo[1,2-a]pyridin-2-ylmethoxy) benzyloxyimino]-4-phenylbutyrate (321 mg, yield 45%) as a colorless oil from an ethyl acetate-hexane (3:2, v/v)-eluted fraction.

NMR (CDCl$_3$) δ: 2.50–2.59 (2H, m), 3.01–3.10 (2H, m), 3.62 (3H, s), 5.16 (2H, s), 5.30 (2H, s), 6.78 (1H, dt, J=1.0, 6.8 Hz), 7.02 (2H, d, J=8.8 Hz), 7.13–7.40 (7H, m), 7.56–7.66 (3H, m), 8.08 (1H, d, J=6.8 Hz).

Example 100

A mixture of 4-(chloromethyl)-2-phenyloxazole (250 mg), methyl E-4-(4-hydroxybenzyloxyimino)-4-phenylbutyrate (369 mg), potassium carbonate (325 mg) and N,N-dimethylformamide (7 ml) was stirred at room temperature for 17 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-phenyl-4-[4-(2-phenyl-4-oxazolylmethoxy) benzyloxyimino]butyrate (320 mg, yield 58%) as a colorless oil from an ethyl acetate-hexane (2:9, v/v)-eluted fraction.

NMR (CDCl$_3$) δ: 2.50–2.60 (2H, m), 3.02–3.11 (2H, m), 3.62 (3H, s), 5.10 (2H, s), 5.17 (2H, s), 7.01 (2H, d, J=8.8 Hz), 7.32–7.40 (5H, m), 7.41–7.49 (3H, m), 7.60–7.66 (2H, m), 7.74 (1H, s), 8.03–8.09 (2H, m).

Example 101

Lithium hydroxide monohydrate (53.0 mg) was added to a solution of methyl E-4-[4-(imidazo[1,2-a]pyridin-2-ylmethoxy)benzyloxyimino]-4-phenylbutyrate (280 mg) in tetrahydrofuran (6 ml)-water (4 ml)-methanol (4 ml) and stirred at room temperature for 2 hours. 1N hydrochloric acid (1.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-[4-(imidazo[1,2-a]pyridin-2-ylmethoxy)benzyloxyimino]-4-phenylbutyric acid (206 mg, yield 76%) as colorless crystals. m.p. 180–182° C.

Example 102

Lithium hydroxide monohydrate (49.9 mg) was added to a solution of methyl E-4-phenyl-4-[4-(2-phenyl-4-oxazolylmethoxy)benzyloxyimino]butyrate (280 mg) in tetrahydrofuran (6 ml)-water (4 ml)-methanol (4 ml) and stirred at room temperature for 2 hours. 1N hydrochloric acid (1.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-phenyl-4-[4-(2-phenyl-4-oxazolylmethoxy) benzyloxyimino]butyric acid (237 mg, yield 87%) as colorless crystals. m.p. 144–145° C.

Example 103

A mixture of 2-chloromethylquinoline hydrochloride (488 mg), methyl E-4-(4-hydroxybenzyloxyimino)-4-phenylbutyrate (650 mg), potassium carbonate (1.00 g) and N,N-dimethylformamide (10 ml) was stirred at room temperature for 13 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-phenyl-4-[4-(2-quinolinylmethoxy) benzyloxyimino]butyrate (655 mg, yield 70%) as a colorless oil from an ethyl acetate-hexane (1:4, v/v)-eluted fraction.

NMR (CDCl$_3$) δ: 2.49–2.58 (2H, m), 3.01–3.10 (2H, m), 3.61 (3H, s), 5.15 (2H, s), 5.40 (2H, s), 7.02 (2H, d, J=8.4 Hz), 7.31–7.38 (5H, m), 7.50–7.85 (6H, m), 8.09 (1H, d, J=8.4 Hz), 8.19 (1H, d, J=8.4 Hz).

Example 104

Lithium hydroxide monohydrate (108 mg) was added to a solution of methyl E-4-phenyl-4-[4-(2-quinolinylmethoxy)benzyloxyimino]butyrate (585 mg) in tetrahydrofuran (6 ml)-water (4 ml)-methanol (4 ml) and stirred at room temperature for 2 hours. 1N hydrochloric acid (2.6 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-4-phenyl-4-[4-(2-quinolinylmethoxy)benzyloxyimino]butyric acid (469 mg, yield 83%) as colorless crystals. m.p. 133–134° C.

Example 105

A mixture of 4-(chloromethyl)-2-phenylthiazole (368 mg), methyl E-4-(4-hydroxybenzyloxyimino)-4-phenylbutyrate (500 mg), potassium carbonate (442 mg) and N,N-dimethylformamide (10 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-4-phenyl-4-[4-(2-phenyl-4-thiazolylmethoxy)benzyloxyimino]butyrate (494 mg, yield 63%) as a colorless oil from an ethyl acetate-hexane (2:9, v/v)-eluted fraction.

NMR (CDCl$_3$) δ: 2.50–2.60 (2H, m), 3.02–3.11 (2H, m), 3.62 (3H, s), 5.17 (2H, s), 5.28 (2H, s), 7.02 (2H, d, J=8.8 Hz), 7.31–7.49 (9H, m), 7.59–7.65 (2H, m), 7.93–7.99 (2H, m).

Example 106

Oxalyl chloride (0.156 ml) and N,N-dimethylformamide (catalytic amount) were added to a solution of E-4-[4-(5-methyl-2-phenyl-4-oxazolylmethoxy)benzyloxyimino]-4-phenylbutyric acid (700 mg) in tetrahydrofuran (10 ml) at room temperature, which was stirred at room temperature for 30 minutes and concentrated. The residue was dissolved in tetrahydrofuran (10 ml) and added dropwise to a mixture of a 25% aqueous ammonia (15 ml) and ethyl acetate (20 ml) at 0° C. After stirring at room temperature for 1 hour, water was added and extracted with ethyl acetate. The ethyl acetate layer was washed with an aqueous saturated solution of sodium chloride, dried (MgSO$_4$) and concentrated. The remaining crystals were recrystallized from ethyl acetate to obtain E-4-[4-(5-methyl-2-phenyl-4-oxazolylmethoxy)benzyloxyimino]-4-phenylbutyramide (315 mg, yield 45%) as colorless crystals. m.p. 164–165° C.

Example 107

Sodium methoxide (108 mg) was added to a solution of E-4-[4-(5-methyl-2-phenyl-4-oxazolylmethoxy)benzyloxyimino]-4-phenylbutyric acid (941 mg) in methanol (5 ml), which was stirred at room temperature for 1 hour and concentrated. The remaining crystals were recrystallized from methanol-diethyl ether to obtain sodium E-4-[4-(5-methyl-2-phenyl-4-oxazolylmethoxy)benzyloxyimino]-4-phenylbutyrate (456 mg, yield 46%) as colorless crystals. m.p. 64–70° C.

Example 108

Lithium hydroxide monohydrate (54.8 mg) was added to a solution of methyl E-4-phenyl-4-[4-(2-phenyl-4-thiazolylmethoxy)benzyloxyimino]butyrate (424 mg) in tetrahydrofuran (10 ml)-water (4 ml)-methanol (4 ml) and stirred at room temperature for 2 hours. 1N hydrochloric acid (1.4 ml) was added to the reaction mixture and extracted with ethyl acetate. The ethyl acetate layer was washed with an aqueous saturated solution of sodium chloride, dried (MgSO$_4$) and concentrated. The remaining crystals were recrystallized from ethyl acetate-hexane to obtain E-4-phenyl-4-[4-(2-phenyl-4-thiazolylmethoxy)benzyloxyimino]butyric acid (369 mg, yield 90%) as colorless crystals. m.p. 104–105° C.

Example 109

After a mixture of 4-(5-methyl-2-phenyl-4-oxazolylmethoxy)benzyloxyamine (600 mg), ethyl 2,2-dimethyl-3-oxo-3-phenylpropionate (468 mg), acetic acid (0.331 ml), sodium acetate (317 mg) and ethanol (20 ml) was heated to reflux for 5 days, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl Z-2,2-dimethyl-3-[4-(5-methyl-2-phenyl-4-oxazolylmethoxy)benzyloxyimino]-3-phenylpropionate (273 mg, yield 28%) as a colorless oil from an ethyl acetate-hexane (2:9, v/v)-eluted fraction.

NMR (CDCl$_3$) δ: 1.11 (3H, t, J=7.1 Hz), 1.31 (6H, s), 2.44 (3H, s), 3.96 (2H, q, J=7.1 Hz), 5.00 (2H, s), 5.07 (2H, s), 7.00 (2H, d, J=8.6 Hz), 7.26–7.46 (10H, m), 8.00–8.06 (2H, m).

Example 110

Potassium hydroxide (1.83 g) was added to a solution of ethyl Z-2,2-dimethyl-3-[4-(5-methyl-2-phenyl-3-oxazolylmethoxy)benzyloxyimino]-3-phenylpropionate (265 mg) in tetrahydrofuran (3 ml)-water (3 ml)-methanol (6 ml), the mixture was heated to reflux for 3 days and cooled to room temperature. Dilute hydrochloric acid was added to the reaction mixture and extracted with ethyl acetate. The ethyl acetate layer was washed with an aqueous saturated solution of sodium chloride, dried (MgSO$_4$) and concentrated. The remaining crystals were recrystallized from ethyl acetate-hexane to obtain Z-2,2-dimethyl-3-[4-(5-methyl-2-phenyl-4-oxazolylmethoxy)benzyloxyimino]-3-phenylpropionic acid (130 mg, yield 52%) as pale-yellow crystals. m.p. 142–143° C. (decomposition).

Example 111

A mixture of E-3-[4-(5-methyl-2-phenyl-4-oxazolylmethoxy)benzyloxyimino]-3-phenylpropionic acid (600 mg), 1-hydroxybenzotriazole ammonia complex (260 mg), 1-ethyl-3-(3-dimethylaminopropyl)carbodiimide hydrochloride (328 mg) and N,N-dimethylformamide (5 ml) was stirred at room temperature for 15 hours. Water was added to the reaction mixture and extracted with ethyl acetate. The ethyl acetate layer was washed successively with an aqueous solution of potassium carbonate and an aqueous saturated solution of sodium chloride, dried (MgSO$_4$) and concentrated. The remaining crystals were recrystallized from tetrahydrofuran-hexane to obtain E-3-[4-(5-methyl-2-phenyl-4-oxazolylmethoxy)benzyloxyimino]-3-phenylpropanamide (512 mg, yield 86%) as colorless crystals. m.p. 164–165° C.

Example 112

Oxalyl chloride (0.156 ml) and N,N-dimethylformamide (catalytic amount) were added to a solution of E-4-[4-(5-methyl-2-phenyl-4-oxazolylmethoxy)benzyloxyimino]-4-phenylbutyric acid (700 mg) in tetrahydrofuran (10 ml) at room temperature, which was stirred at room temperature for 30 minutes and concentrated. The residue was dissolved in tetrahydrofuran (5 ml) and added dropwise to a mixture of a 40% aqueous dimethylamine (20 ml) and ethyl acetate (20 ml) at 0° C. After stirred at room temperature for 2 hours, water was added and extracted with ethyl acetate. The ethyl acetate layer was washed with an aqueous saturated solution of sodium chloride, dried (MgSO$_4$) and concentrated. The residue was subjected to silica gel chromatography to obtain E-N,N-dimethyl-4-[4-(5-methyl-2-phenyl-4-oxazolylmethoxy)benzyloxyimino]-4-phenylbutanamide (511 mg, yield 69%) as a colorless oil from an ethyl acetate-hexane (2:1, v/v).

NMR (CDCl$_3$) δ: 2.43–2.55 (5H, m), 2.83 (3H, s), 2.88 (3H, s), 3.01–3.10 (2H, m), 5.00 (2H, s), 5.17 (2H, s), 7.01 (2H, d, J=8.6 Hz), 7.30–7.48 (8H, m), 7.63–7.71 (2H, m), 7.97–8.05 (2H, m).

Example 113

Oxalyl chloride (0.156 ml) and N,N-dimethylformamide (catalytic amount) were added to a solution of E-4-[4-(5-methyl-2-phenyl-4-oxazolylmethoxy)benzyloxyimino]-4-phenylbutyric acid (700 mg) in tetrahydrofuran (10 ml) at room temperature, which was stirred at room temperature for 30 minutes and concentrated. The residue was dissolved in tetrahydrofuran (5 ml) and added dropwise to a mixture of a 40% aqueous methylamine (20 ml) and ethyl acetate (30 ml) at 0° C. After stirred at room temperature for 1 hour, water was added and extracted with ethyl acetate. The ethyl acetate layer was washed with an aqueous saturated solution of sodium chloride, dried ($MgSO_4$) and concentrated. The remaining crystals were recrystallized from ethyl acetate-hexane to obtain E-N-methyl-4-[4-(5-methyl-2-phenyl-4-oxazolylmethoxy)benzyloxyimino]-4-phenylbutaneamide-(466 mg, yield 65%) as colorless crystals. m.p. 141–142° C.

Example 114

Lithium hydroxide monohydrate (44.6 mg) was added to a solution of E-4-[4-(5-methyl-2-phenyl-4-oxazolylmethoxy)benzyloxyimino]-4-phenylbutyric acid (500 mg) in methanol (10 ml), which was stirred at room temperature for 30 minutes and concentrated. The remaining crystals were recrystallized from methanol-diethyl ether to obtain lithium E-4-[4-(5-methyl-2-phenyl-4-oxazolylmethoxy)benzyloxyimino]-4-phenylbutyrate (485 mg, yield 96%) as colorless crystals. m.p. 201–203° C.

Example 115

A 1N aqueous saturated solution of sodium hydroxide (5 ml) was added to a solution of ethyl E-7-[4-(5-methyl-2-phenyl-4-oxazolylmethoxy)benzyloxyimino]-7-phenylheptanoate (730 mg) in tetrahydrofuran (10 ml)-methanol (5 ml) and stirred at room temperature for 1 hour. 1N hydrochloric acid (5.5 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain E-7-[4-(5-methyl-2-phenyl-4-oxazolylmethoxy)benzyloxyimino]-7-phenylheptanoic acid (569 mg, yield 82%) as colorless crystals. m.p. 84–85° C.

Example 116

Lithium hydroxide monohydrate (159 mg) was added to a solution of ethyl Z-8-[4-(5-methyl-2-phenyl-4-oxazolylmethoxy)benzyloxyimino]-8-phenyloctanoate (340 mg) in tetrahydrofuran (6 ml)-water (4 ml)-methanol (4 ml) and stirred at room temperature for 1 hour. 1N hydrochloric acid (3.8 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain Z-8-[4-(5-methyl-2-phenyl-4-oxazolylmethoxy)benzyloxyimino]-8-phenyloctanoic acid (293 mg, yield 91%) as colorless crystals. m.p. 88–89° C.

Example 117

After a mixture of 4-(5-methyl-2-phenyl-4-oxazolylmethoxy)benzyloxyamine (600 mg), methyl 8-(4-methoxyphenyl)-8-oxooctanoate (538 mg), acetic acid (0.331 ml), sodium acetate (317 mg) and methanol (20 ml) was heated to reflux for 16 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain methyl E-8-(4-methoxyphenyl)-8-[4-(5-methyl-2-phenyl-4-oxazolylmethoxy)benzyloxyimino]octanoate (650 mg, yield 59%) as a colorless oil from an ethyl acetate-hexane (2:7, v/v)-eluted fraction.

NMR ($CDCl_3$) δ: 1.20–1.65 (8H, m), 2.26 (2H, t, J=7.5 Hz), 2.44 (3H, s), 2.72 (2H, t, J=7.7 Hz), 3.65 (3H, s), 3.82 (3H, s), 5.00 (2H, s), 5.13 (2H, s), 6.88 (2H, d, J=8.8 Hz), 7.01 (2H, d, J=8.8 Hz), 7.35 (2H, d, J=8.8 Hz), 7.39–7.48 (3H, m), 7.56 (2H, d, J=8.8 Hz), 7.99–8.05 (2H, m).

Example 118

Lithium hydroxide monohydrate (128 mg) was added to a solution of methyl E-8-(4-methoxyphenyl)-8-[4-(5-methyl-2-phenyl-4-oxazolylmethoxy)benzyloxyimino] octanoate (580 mg) in tetrahydrofuran (10 ml)-water (4 ml)-methanol (4 ml) and stirred at room temperature for 1 hour. 1N hydrochloric acid (3.1 ml) was added to the reaction mixture and extracted with ethyl acetate. The ethyl acetate layer was washed with an aqueous saturated solution of sodium chloride, dried ($MgSO_4$) and concentrated. The residue was recrystallized from ethyl acetate-hexane to obtain E-8-(4-methoxyphenyl)-8-[4-(5-methyl-2-phenyl-4-oxazolylmethoxy)benzyloxyimino]octanoic acid (528 mg, yield 93%) as colorless crystals. m.p. 69–70° C.

Example 119

After a mixture of 4-(5-methyl-2-phenyl-4-oxazolylmethoxy)benzyloxyamine (600 mg), 8-(4-chlorophenyl)-8-oxooctanoic acid (546 mg), acetic acid (0.331 ml), sodium acetate (317 mg) and methanol (20 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried ($MgSO_4$) and concentrated. The residue was subjected to silica gel chromatography to obtain methyl E-8-(4-chlorophenyl)-8-[4-(5-methyl-2-phenyl-4-oxazolylmethoxy)benzyloxyimino]octanoate (828 mg, yield 75%) as a colorless oil from an ethyl acetate-hexane (1:6, v/v)-eluted fraction.

NMR ($CDCl_3$) δ: 1.20–1.65 (8H, m), 2.26 (2H, t, J=7.5 Hz), 2.44 (3H, s), 2.67–2.76 (2H, m), 3.65 (3H, s), 5.00 (2H, s), 5.14 (2H, s), 7.01 (2H, d, J=8.8 Hz), 7.29–7.37 (4H, m), 7.40–7.47 (3H, m), 7.55 (2H, d, J=8.8 Hz), 7.99–8.05 (2H, m).

Example 120

Methyl Z-8-(4-chlorophenyl)-8-[4-(5-methyl-2-phenyl-4-oxazolylmethoxy)benzyloxyimino]octanoate (215 mg, yield 19%) as a colorless oil was obtained from a fraction which eluted following the E-compound in Example 119.

NMR ($CDCl_3$) δ: 1.20–1.65 (8H, m), 2.27 (2H, t, J=7.4 Hz), 2.41–2.53 (5H, m), 3.65 (3H, s), 4.99 (2H, s), 5.01 (2H, s), 6.98 (2H, d, J=8.8 Hz), 7.22–7.37 (6H, m), 7.40–7.46 (3H, m), 7.99–8.05 (2H, m).

Example 121

After a mixture of 4-(5-methyl-2-phenyl-4-oxazolylmethoxy)benzyloxyamine (600 mg), 8-(4-fluorophenyl)-8-oxooctanoic acid (514 mg), acetic acid (0.331 ml), sodium acetate (317 mg) and methanol (20 ml) was heated to reflux for 18 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-8-(4-fluorophenyl)-8-[4-(5-methyl-2-phenyl-4-oxazolylmethoxy)benzyloxyimino]octanoate (771 mg, yield 71%) as a colorless oil from an ethyl acetate-hexane (1:6, v/v)-eluted fraction.

NMR (CDCl$_3$) δ: 1.20–1.65 (8H, m), 2.26 (2H, t, J=7.5 Hz), 2.44 (3H, s), 2.68–2.76 (2H, m), 3.65 (3H, s), 5.00 (2H, s), 5.14 (2H, s), 6.97–7.10 (4H, m), 7.35 (2H, d, J=8.8 Hz), 7.39–7.48 (3H, m), 7.54–7.63 (2H, m), 7.97–8.05 (2H, m).

Example 122

Methyl Z-8-(4-fluorophenyl)-8-[4-(5-methyl-2-phenyl-4-oxazolylmethoxy)benzyloxyimino]octanoate (205 mg, yield 19%) as a colorless oil was obtained from a fraction which eluted following the E-compound in Example 121.

NMR (CDCl$_3$) δ: 1.20–1.65 (8H, m), 2.27 (2H, t, J=7.5 Hz), 2.43 (3H, s), 2.45–2.53 (2H, m), 3.65 (3H, s), 4.99 (2H, s), 5.01 (2H, s), 6.95–7.09 (4H, m), 7.23–7.46 (7H, m), 7.98–8.04 (2H, m).

Example 123

Lithium hydroxide monohydrate (160 mg) was added to a solution of methyl E-8-(4-chlorophenyl)-8-[4-(5-methyl-2-phenyl-4-oxazolylmethoxy)benzyloxyimino]octanoate (730 mg) in tetrahydrofuran (10 ml)-water (4 ml)-methanol (4 ml) and stirred at room temperature for 3 hours. 1N hydrochloric acid (3.9 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-(4-chlorophenyl)-8-[4-(5-methyl-2-phenyl-4-oxazolylmethoxy)benzyloxyimino]octanoic acid (632 mg, yield 89%) as colorless crystals. m.p. 90–91° C.

Example 124

Lithium hydroxide monohydrate (43.7 mg) was added to a solution of methyl Z-8-(4-chlorophenyl)-8-[4-(5-methyl-2-phenyl-4-oxazolylmethoxy)benzyloxyimino]octanoate (200 mg) in tetrahydrofuran (10 ml)-water (4 ml)-methanol (4 ml) and stirred at room temperature for 3 hours. 1N hydrochloric acid (1.1 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain Z-8-(4-chlorophenyl)-8-[4-(5-methyl-2-phenyl-4-oxazolylmethoxy)benzyloxyimino]octanoic acid (169 mg, yield 87%) as colorless crystals. m.p. 54–57° C.

Example 125

Lithium hydroxide monohydrate (157 mg) was added to a solution of methyl E-8-(4-fluorophenyl)-8-[4-(5-methyl-2-phenyl-4-oxazolylmethoxy)benzyloxyimino]octanoate (700 mg) in tetrahydrofuran (10 ml)-water (4 ml)-methanol (4 ml) and stirred at room temperature for 3 hours. 1N hydrochloric acid (3.8 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-(4-fluorophenyl)-8-[4-(5-methyl-2-phenyl-4-oxazolylmethoxy)benzyloxyimino]octanoic acid (608 mg, yield 89%) as colorless crystals. m.p. 79–80° C.

Example 126

Lithium hydroxide monohydrate (42.8 mg) was added to a solution of methyl Z-8-(4-fluorophenyl)-8-[4-(5-methyl-2-phenyl-4-oxazolylmethoxy)benzyloxyimino]octanoate (190 mg) in tetrahydrofuran (10 ml)-water (4 ml)-methanol (4 ml) and stirred at room temperature for 3 hours. 1N hydrochloric acid (1.1 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain Z-8-(4-fluorophenyl)-8-[4-(5-methyl-2-phenyl-4-oxazolylmethoxy)benzyloxyimino]octanoic acid (59 mg, yield 32%) as colorless crystals. m.p. 56–57° C.

Example 127

A mixture of 3-chloromethyl-5-phenyl-1,2,4-oxadiazole (335 mg), ethyl E-8-(4-hydroxybenzyloxyimino)-8-phenyloctanoate (600 mg), potassium carbonate (432 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-8-phenyl-8-[4-(5-phenyl-1,2,4-oxadiazol-3-ylmethoxy)benzyloxyimino]octanoate (267 mg, yield 32%) as a colorless oil from an ethyl acetate-hexane (1:5, v/v)-eluted fraction.

NMR (CDCl$_3$) δ: 1.20–1.65 (11H, m), 2.24 (2H, t, J=7.5 Hz), 2.70–2.79 (2H, m), 4.11 (2H, q, J=7.11 Hz), 5.15 (2H, s), 5.26 (2H, s), 7.05 (2H, d, J=8.8 Hz), 7.30–7.40 (5H, m), 7.48–7.66 (5H, m), 8.17 (2H, d, J=8.2 Hz).

Example 128

Lithium hydroxide monohydrate (54.9 mg) was added to a solution of ethyl E-8-phenyl-8-[4-(5-phenyl-1,2,4-oxadiazol-3-ylmethoxy)benzyloxyimino]octanoate (236 mg) in tetrahydrofuran (6 ml)-water (4 ml)-ethanol (4 ml) and stirred at room temperature for 4 hours. 1N hydrochloric acid (1.4 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-phenyl-8-[4-(5-phenyl-1,2,4-oxadiazol-3-ylmethoxy)benzyloxyimino]octanoic acid (208 mg, yield 93%) as colorless crystals. m.p. 76–77° C.

Example 129

Lithium hydroxide monohydrate (143 mg) was added to a solution of ethyl E-8-[4-[2-(2-furyl)-5-methyl-4-oxazolylmethoxy]benzyloxyimino]-8-phenyloctanoate (618 mg) in tetrahydrofuran (6 ml)-water (4 ml)-ethanol (4 ml) and stirred at room temperature for 4 hours. 1N hydrochloric acid (3.5 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-[4-[2-(2-furyl)-5-methyl-4-oxazolylmethoxy]benzyloxyimino]-8-phenyloctanoic acid (523 mg, yield 90%) as colorless crystals. m.p. 75–77° C.

Example 130

Lithium hydroxide monohydrate (153 mg) was added to a solution of ethyl E-8-[4-[5-methyl-2-(2-thienyl)-4-oxazolylmethoxy]benzyloxyimino]-8-phenyloctanoate (682 mg) in tetrahydrofuran (6 ml)-water (4 ml)-ethanol (4 ml) and stirred at room temperature for 4 hours. 1N hydrochloric acid (3.7 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-8-[4-[5-methyl-2-(2-thienyl)-4-oxazolylmethoxy]benzyloxyimino]-8-phenyloctanoic acid (567 mg, yield 87%) as colorless crystals. m.p. 106–108° C.

Example 131

A mixture of 4-chloromethyl-2-(2-furyl)-5-methyloxazole (368 mg), ethyl E-6-(4-hydroxybenzyloxyimino)-6-phenylhexanoate (600 mg), potassium carbonate (467 mg) and N,N-dimethylformamide (7 ml) was stirred at room temperature for 13 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-[4-[2-(2-furyl)-5-methyl-4-oxazolylmethoxy]benzyloxyimino]-6-phenylhexanoate (770 mg, yield 88%) as a colorless oil from an ethyl acetate-hexane (2:7, v/v)-eluted fraction.

NMR (CDCl$_3$) δ: 1.22 (3H, t, J=7.1 Hz), 1.45–1.75 (4H, m), 2.28 (2H, t, J=7.1 Hz), 2.42 (3H, s), 2.73–2.82 (2H, m), 4.09 (2H, q, J=7.1 Hz), 5.00 (2H, s), 5.15 (2H, s), 6.51–6.54 (1H, m), 6.95–7.03 (3H, m), 7.30–7.39 (5H, m), 7.53–7.64 (3H, m).

Example 132

Lithium hydroxide monohydrate (163 mg) was added to a solution of ethyl E-6-[4-[2-(2-furyl)-5-methyl-4-oxazolylmethoxy]benzyloxyimino]-6-phenylhexanoate (670 mg) in tetrahydrofuran (6 ml)-water (4 ml)-ethanol (4 ml) and stirred at room temperature for 4 hours. 1N hydrochloric acid (3.9 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-6-[4-[2-(2-furyl)-5-methyl-4-oxazolylmethoxy]benzyloxyimino]-6-phenylhexanoic acid (625 mg, yield 98%) as colorless crystals. m.p. 112–113° C.

Example 133

A mixture of 4-chloromethyl-5-methyl-2-(2-thienyl)oxazole (397 mg), ethyl E-6-(4-hydroxybenzyloxyimino)-6-phenylhexanoate (600 mg), potassium carbonate (467 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-[4-[5-methyl-2-(2-thienyl)-4-oxazolylmethoxy]benzyloxyimino]-6-phenylhexanoate (856 mg, yield 95%) as a colorless oil from an ethyl acetate-hexane (1:4, v/v)-eluted fraction.

NMR (CDCl$_3$) δ: 1.22 (3H, t, J=7.1 Hz), 1.45–1.75 (4H, m), 2.28 (2H, t, J=7.1 Hz), 2.41 (3H, s), 2.77 (2H, t, J=7.4 Hz), 4.09 (2H, q, J=7.1 Hz), 4.98 (2H, s), 5.15 (2H, s), 6.99 (2H, d, J=8.8 Hz), 7.09 (1H, dd, J=3.6, 5.0 Hz), 7.31–7.42 (6H, m), 7.58–7.65 (3H, m).

Example 134

A mixture of 3-chloromethyl-5-phenyl-1,2,4-oxadiazole (362 mg), ethyl E-6-(4-hydroxybenzyloxyimino)-6-phenylhexanoate (600 mg), potassium carbonate (467 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-phenyl-6-[4-(5-phenyl-1,2,4-oxadiazol-3-ylmethoxy)benzyloxyimino]hexanoate (649 mg, yield 75%) as a colorless oil from an ethyl acetate-hexane (1:4, v/v)-eluted fraction.

NMR (CDCl$_3$) δ: 1.22 (3H, t, J=7.1 Hz), 1.45–1.75 (4H, m), 2.28 (2H, t, J=7.2 Hz), 2.77 (2H, t, J=7.5 Hz), 4.09 (2H, q, J=7.1 Hz), 5.16 (2H, s), 5.27 (2H, s), 7.06 (2H, d, J=8.8 Hz), 7.31–7.40 (5H, m), 7.49–7.66 (5H, m), 8.14–8.20 (2H, m).

Example 135

Lithium hydroxide monohydrate (177 mg) was added to a solution of ethyl E-6-[4-[5-methyl-2-(2-thienyl)-4-oxazolylmethoxy]benzyloxyimino]-6-phenylhexanoate (747 mg) in tetrahydrofuran (6 ml)-water (4 ml)-ethanol (4 ml) and stirred at room temperature for 4 hours. 1N hydrochloric acid (4.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-6-[4-[5-methyl-2-(2-thienyl)-4-oxazolylmethoxy]benzyloxyimino]-6-phenylhexanoic acid (653 mg, yield 92%) as colorless crystals. m.p. 101–102° C.

Example 136

Lithium hydroxide monohydrate (134 mg) was added to a solution of ethyl E-6-phenyl-6-[4-(5-phenyl-1,2,4-oxadiazol-3-ylmethoxy)benzyloxyimino]hexanoate (545 mg) in tetrahydrofuran (6 ml)-water (4 ml)-ethanol (4 ml) and stirred at room temperature for 4 hours. 1N hydrochloric acid (3.3 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-6-phenyl-6-[4-(5-phenyl-1,2,4-oxadiazol-3-ylmethoxy)benzyloxyimino]hexanoic acid (465 mg, yield 90%) as colorless crystals. m.p. 88–89° C.

Example 137

A mixture of 5-chloromethyl-3-phenyl-1,2,4-oxadiazole (362 mg), ethyl E-6-(4-hydroxybenzyloxyimino)-6-phenylhexanoate (600 mg), potassium carbonate (467 mg) and N,N-dimethylformamide (7 ml) was stirred at room temperature for 18 hours. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain ethyl E-6-phenyl-6-[4-(3-phenyl-1,2,4-oxadiazol-5-ylmethoxy)benzyloxyimino]hexanoate (789 mg, yield 92%) as a colorless oil from an ethyl acetate-hexane (2:9, v/v)-eluted fraction.

NMR (CDCl$_3$) δ: 1.22 (3H, t, J=7.11 Hz), 1.45–1.75 (4H, m), 2.28 (2H, t, J=7.4 Hz), 2.77 (2H, t, J=7.4 Hz), 4.09 (2H, q, J=7.1 Hz), 5.16 (2H, s), 5.36 (2H, s), 7.02 (2H, d, J=8.6 Hz), 7.28–7.65 (10H, m), 8.06–8.15 (2H, m).

Example 138

Lithium hydroxide monohydrate (194 mg) was added to a solution of ethyl E-6-phenyl-6-[4-(3-phenyl-1,2,4-oxadiazol-5-ylmethoxy)benzyloxyimino]hexanoate (790 mg) in tetrahydrofuran (6 ml)-water (4 ml)-ethanol (4 ml) and stirred at room temperature for 4 hours. 1N hydrochloric acid (4.7 ml) was added to the reaction mixture and extracted with ethyl acetate. The ethyl acetate layer was washed with an aqueous saturated solution of sodium chloride, dried (MgSO$_4$) and concentrated. The residue was recrystallized from ethyl acetate-hexane to obtain E-6-phenyl-6-[4-(3-phenyl-1,2,4-oxadiazol-5-ylmethoxy)benzyloxyimino]hexanoic acid (637 mg, yield 85%) as colorless crystals. m.p. 91–92° C.

Example 139

After a mixture of 4-(5-methyl-2-phenyl-4-oxazolylmethoxy)benzyloxyamine (1.00 g), 4-oxo-4-phenylbutanamide (571 mg), acetic acid (0.553 ml), sodium acetate (528 mg) and ethanol (20 ml) was heated to reflux for 10 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography and concentrated a portion from an ethyl acetate-hexane (3:1, v/v)-eluted fraction which eluted following the E-compound, to obtain crystals. The crystals were recrystallized from ethanol to obtain Z-4-[4-(5-methyl-2-phenyl-4-oxazolylmethoxy)benzyloxyimino]-4-phenylbutanamide (120 mg, yield 8%) as colorless crystals. m.p. 110–112° C.

Example 140

After a mixture of 4-(5-methyl-2-phenyl-4-oxazolylmethoxy)benzyloxyamine (467 mg), methyl 2,2-dimethyl-6-oxo-6-phenylhexanoate (340 mg), acetic acid (0.259 ml), sodium acetate (248 mg) and methanol (15 ml) was heated to reflux for 15 hours, the mixture was cooled to room temperature. Water was added to the reaction mixture and extracted with ethyl acetate. The ethyl acetate layer was washed with an aqueous saturated solution of sodium chloride, dried (MgSO$_4$) and concentrated. The residue was subjected to silica gel chromatography to obtain methyl E-2,2-dimethyl-6-[4-(5-methyl-2-phenyl-4-oxazolylmethoxy)benzyloxyimino]-6-phenylhexanoate (348 mg, yield 47%) as a colorless oil from an ethyl acetate-hexane (1:5, v/v)-eluted fraction.

NMR (CDCl$_3$) δ: 1.10 (6H, s), 1.35–1.65 (4H, m), 2.44 (3H, s), 2.73 (2H, t, J=7.3 Hz), 3.55 (3H, s), 5.00 (2H, s), 5.15 (2H, s), 7.02 (2H, d, J=8.8 Hz), 7.33–7.48 (8H, m), 7.57–7.63 (2H, m), 7.99–8.05 (2H, m).

Example 141

A 4N aqueous solution of potassium hydroxide (5 ml) was added to a solution of methyl E-2,2-dimethyl-6-[4-(5-methyl-2-phenyl-4-oxazolylmethoxy)benzyloxyimino]-6-phenylhexanoate (340 mg) in tetrahydrofuran (5 ml)-methanol (5 ml), which was heated to reflux for 2 hours and cooled to room temperature. Dilute hydrochloric acid was added to the reaction mixture to neutralize and extracted with ethyl acetate. The ethyl acetate layer was washed with an aqueous saturated solution of sodium chloride, dried (MgSO$_4$) and concentrated. The residue was subjected to silica gel chromatography to obtain E-2,2-dimethyl-6-[4-(5-methyl-2-phenyl-4-oxazolylmethoxy)benzyloxyimino]-6-phenylhexanoic acid (275 mg, yield 83%) as colorless crystals. m.p. 111–112° C.

Example 142

Oxalyl chloride (0.126 ml) and N,N-dimethylformamide (catalytic amount) were added to a solution of E-6-[4-(5-methyl-2-phenyl-4-oxazolylmethoxy)benzyloxyimino]-6-phenylhexanoate (600 mg) in tetrahydrofuran (5 ml) at room temperature, which was stirred at room temperature for 30 minutes and concentrated. The residue was dissolved in tetrahydrofuran (10 ml) and methanesulfonamide (137 mg) and N,N-dimethylaminopyridine (293 mg) were added. After the reaction mixture was stirred at room temperature for 18 hours, 1N hydrochloric acid was added and extracted with ethyl acetate. The ethyl acetate layer was washed with an aqueous saturated solution of sodium chloride, dried (MgSO$_4$) and concentrated. The residue was subjected to silica gel chromatography to obtain crystals from an ethyl acetate-hexane (1:1, v/v)-eluted fraction. The crystals were recrystallized from ethyl acetate-hexane to obtain E-N-methanesulfonyl-6-[4-(5-methyl-2-phenyl-4-oxazolylmethoxy)benzyloxyimino]-6-phenylhexanamide (458 mg, yield 66%) as colorless crystals. m.p. 130–132° C.

Example 143

To a stirred solution of 4-(2-chloromethylphenoxymethyl)-5-methyl-2-phenyloxazole (1.50 g) and methyl E-4-hydroxyimino-4-phenylbutyrate (990 mg) in N,N-dimethylformamide (40 ml) was added sodium hydride (60% in oil, 200 mg) at 0° C. After stirring for 2 hours, the reaction mixture was poured into water, neutralized with 2N hydrochloric acid, and extracted with ethyl acetate. The extract was washed with water, dried (MgSO$_4$), and concentrated. The residue was purified by column chromatography on silica gel. Elution with ethyl acetate-hexane (1:4, v/v) gave methyl E-4-[2-(5-methyl-2-phenyl-4-oxazolylmethoxy)benzyloxyimino]-4-phenylbutyrate (1.65 g, yield 71%) as a colorless oil.

NMR (CDCl$_3$) δ: 2.43 (3H, s), 2.5–2.65 (2H, m), 3.0–3.15 (2H, m), 3.61 (3H, s), 5.07 (2H, s), 5.33 (2H, s), 6.98 (1H, dd, J=7.5, 1.0 Hz), 7.25–7.5 (8H, m), 7.55–7.7 (2H, m), 7.95–8.1 (2H, m).

Example 144

A mixture of methyl E-4-[2-(5-methyl-2-phenyl-4-oxazolylmethoxy)benzyloxyimino]-4-phenylbutyrate (1.60 g), methanol (5 ml), tetrahydrofuran (10 ml) and 1N aqueous sodium hydroxide (5 ml) was stirred at room temperature for 2 hours. The reaction mixture was poured into water, acidified with 2N hydrochloric acid, and extracted with ethyl acetate. The extract was washed with water, dried (MgSO$_4$), and concentrated to give E-4-[2-(5-methyl-2-phenyl-4- oxazolylmethoxy)benzyloxyimino]-4-phenylbutyric acid (1.42 g, yield 91%) as crystals. Recrystallization from ethyl acetate-hexane gave colorless needles. m.p. 116–117° C.

Example 145

To a stirred solution of 4-(4-chloromethyl-2,6-dimethoxyphenoxymethyl)-5-methyl-2-phenyloxazole (1.00 g) and methyl E-4-hydroxyimino-4-phenylbutyrate (585 mg) in N,N-dimethylformamide (40 ml) was added sodium hydride (60% in oil, 115 mg) at 0° C. After stirring for 2 hours, the reaction mixture was poured into water, neutralized with 2N hydrochloric acid, and extracted with ethyl acetate. The extract was washed with water, dried (MgSO$_4$), and concentrated. The residue was purified by column chromatography on silica gel. Elution with ethyl acetate-hexane (1:3, v/v) gave methyl E-4-[3,5-dimethoxy-4-(5-methyl-2-phenyl-4-oxazolylmethoxy)benzyloxyimino]-4-phenylbutyrate (970 mg, yield 65%) as a colorless oil.

NMR (CDCl$_3$) δ: 2.32 (3H, s), 2.5–2.65 (2H, m), 3.05–3.15 (2H, m), 3.63 (3H, s), 3.84 (6H, s), 4.97 (2H, s), 5.16 (2H, s), 6.63 (2H, s), 7.3–7.5 (6H, m), 7.6–7.7 (2H, m), 7.95–8.05 (2H, m).

Example 146

A mixture of methyl E-4-[3,5-dimethoxy-4-(5-methyl-2-phenyl-4-oxazolylmethoxy)benzyloxyimino]-4-phenylbutyrate (970 mg), methanol (5 ml), tetrahydrofuran (10 ml) and 1N aqueous sodium hydroxide (5 ml) was stirred at room temperature for 1 hour. The reaction mixture was poured into water, acidified with 2N hydrochloric acid, and extracted with ethyl acetate. The extract was washed with water, dried (MgSO$_4$), and concentrated to give E-4-[3,5-dimethoxy-4-(5-methyl-2-phenyl-4-oxazolylmethoxy)benzyloxyimino]-4-phenylbutyric acid (880 mg, yield 93%) as crystals. Recrystallization from ethyl acetate-isopropyl ether gave colorless needles. m.p. 89–90° C.

Example 147

To a stirred solution of 4-(4-chloromethyl-2-methoxyphenoxymethyl)-2-(2-furyl)-5-methyloxazole (1.65 g) and methyl E-4-hydroxyimino-4-phenylbutyrate (1.04 g) in N,N-dimethylformamide (20 ml) was added sodium hydride (60% in oil, 200 mg) at 0° C. After stirring for 1 hour, the reaction mixture was poured into water, neutralized with 1N hydrochloric acid, and extracted with ethyl acetate. The extract was washed with water, dried (MgSO$_4$), and concentrated. The residue was purified by column chromatography on silica gel. Elution with ethyl acetate-hexane (1:4, v/v) gave methyl E-4-[4-[2-(2-furyl)-5-methyl-4-oxazolylmethoxy]-3-methoxybenzyloxyimino]-4-phenylbutyrate (1.60 g, yield 64%) as crystals. Recrystallization from ethyl acetate-hexane gave pale yellow prisms. m.p. 67–69° C.

Example 148

A mixture of methyl E-4-[4-[2-(2-furyl)-5-methyl-4-oxazolylmethoxy]-3-methoxybenzyloxyimino]-4-phenylbutyrate (1.55 g, ethanol (10 ml) and 1N aqueous sodium hydroxide (5 ml) was stirred at room temperature for 2 hours. The reaction mixture was poured into water and acidified with 1N hydrochloric acid to give E-4-[4-[2-(2-furyl)-5-methyl-4-oxazolylmethoxy]-3-methoxybenzyloxyimino]-4-phenylbutyric acid as crystals (1.40 g, yield 93%). Recrystallization from ethanol-isopropyl ether gave colorless prisms. m.p. 131–132° C.

Example 149

In substantially the same manner as in example 147, 4-(4-chloromethyl-2-methoxyphenoxymethyl)-5-methyl-2-phenyloxazole was reacted with E-4-hydroxyimino-4-phenylbutyrate (1.10 g) to obtain methyl E-4-[3-methoxy-4-(5-methyl-2-phenyl-4-oxazolylmethoxy)benzyloxyimino]-4-phenylbutyrate (1.20 g, yield 44%) as crystals. Recrystallization from ethyl acetate-isopropyl ether gave pale-yellow prisms. m.p. 112–114° C.

Example 150

In substantially the same manner as in example 148, methyl E-4-[3-methoxy-4-(5-methyl-2-phenyl-4-oxazolylmethoxy)benzyloxyimino]-4-phenylbutyrate (1.00 g) was reacted with 1N aqueous sodium hydroxide to obtain E-4-[3-methoxy-4-(5-methyl-2-phenyl-4-oxazolylmethoxy)benzyloxyimino]-4-phenylbutyric acid (790 mg, yield 80%). Recrystallization from ethanol-isopropyl ether gave colorless prisms. m.p. 134–135° C.

| Pharmaceutical Composition Example 1 (Production of capsules) | |
|---|---|
| 1) compound (7) | 30 mg |
| 2) cellulose powder | 10 mg |
| 3) lactose | 19 mg |
| 4) magnesium stearic acid | 1 mg |
| Sum | 60 mg |

Components 1), 2), 3) and 4) are mixed and packed in gelatin capsules.

| Pharmaceutical Composition Example 2 (Production of tablets) | |
|---|---|
| 1) compound (7) | 30 g |
| 2) lactose | 50 g |
| 3) corn starch | 15 g |
| 4) carboxymethylcellulose calcium | 44 g |
| 5) magnesium stearic acid | 1 g |
| 1000 tablets     Sum | 140 g |

The entire amounts of Components 1), 2) and 3) and 30 g of Component 4) are milled with water, freeze-dried, and then pulverized. The pulverized powder is admixed with 14 g of Component 4) and 1 g of Component 5), and compacted into tablets. In this manner, 1000 tablets each of which containing 30 mg of compound (7) are produced.

EFFECTS OF THE INVENTION

A compound or a pharmaceutical composition according to the present invention has less toxicity, and can be used for the prevention or treatment of diabetes mellitus (e.g., insulin-dependent diabetes mellitus (type-1 diabetes mellitus), non-insulin-dependent diabetes mellitus (type-2 diabetes mellitus), pregnancy diabetes mellitus and the like), hyperlipemia (e.g., hypertriglycemia, hypercholesterolemia, hypoHDLemia and the like), insulin insensitivity, insulin resistance, and impaired glucose tolerance (IGT).

A compound or a pharmaceutical composition according to the present invention may also be used for the prevention or treatment of diabetic complications (e.g., neuropathy, nephropathy, retinopathy, cataract, microangiopathy, osteopenia and the like), obesity, osteoporosis, cachexia (e.g., carcinomatous cachexia, tuberculous cachexia, diabetic cachexia, hemophathic cachexia, endocrinopathic cachexia, infectious cachexia or cachexia induced by acquired immunodeficiency syndrome), fatty liver, hypertension, polycystic ovary syndrome, renal disorders (e.g., glomerular nephritis, glomerulosclerosis, nephrotic syndrome, hypertensive nephrosclerosis, terminal renal disorders and the like), muscular dystrophy, myocardiac infarction, angina pectoris, cerebral infarction, insulin resistance syndrome, syndrome X, hyperinsulinemia-induced sensory disorder, tumors (e.g., leukemia, breast cancer, prostate cancer, skin cancer and the like), inflammatory diseases (e.g., rheumatoid arthritis, spondylitis deformans, osteoarthritis, lumbago, gout, surgical wound inflammation and swelling remedy, neuralgia, pharyngolaryngitis, cystitis, hepatitis, pneumonia, pancreatitis and the like), arterial sclerosis (e.g., atherosclerosis and the like).

A compound according to the invention may also be employed as a pharmaceutical for controlling appetite or food intake, diet and anorexia.

What is claimed is:

1. A method for treating sydrome X which comprises administering a pharmaceutically effective amount of the compound represented by the formula of:

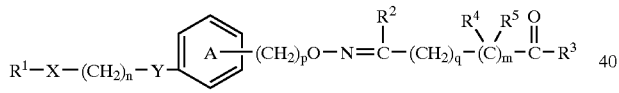

wherein $R^1$ is an optionally substituted thiazolyl, oxazolyl or oxadiazolyl group;

X is a bond, —CO—, —CH(OH)— or a group represented by —NR$^6$—
  wherein $R^6$ is a hydrogen atom or an optionally substituted alkyl group;

n is an integer of 1 to 3;

Y is an oxygen atom, a sulfur atom, —SO—, —SO$_2$— or a group represented by —NR$^7$—
  wherein $R^7$ is a hydrogen atom or an optionally substituted alkyl group;

ring A is a benzene ring optionally having additional one to three substituents;

p is an integer of 1 to 8;

$R^2$ is a hydrogen atom, an optionally substituted hydrocarbon group or an optionally substituted heterocyclic group; q is an integer of 0 to 6;

m is 0 or 1;

$R^3$ is a hydroxy group, OR$^8$ or NR$^9$R$^{10}$
  wherein $R^8$ is an optionally substituted hydrocarbon group and
  wherein $R^9$ and $R^{10}$ are the same or different groups which are selected from a hydrogen atom, an optionally substituted hydrocarbon group, an optionally substituted heterocyclic group and an optionally substituted acyl group or $R^9$ and $R^{10}$ combine together to form a ring;

$R^4$ and $R^5$ are the same or different groups which are selected from a hydrogen atom and an optionally substituted hydrocarbon group wherein $R^4$ may form a ring with $R^2$;

or a salt thereof.

2. A pharmaceutical composition comprising
(1) a compound represented by the formula of

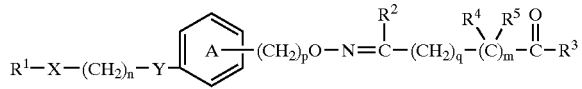

wherein $R^1$ is an optionally substituted thiazolyl, oxazolyl or oxadiazolyl group;

X is a bond, —CO—, —CH(OH)— or a group represented by —NR$^6$—
  wherein $R^6$ is a hydrogen atom or an optionally substituted alkyl group;

n is an integer of 1 to 3;

Y is an oxygen atom, a sulfur atom, —SO—, —SO$_2$— or a group represented by —NR$^7$—
  wherein $R^7$ is a hydrogen atom or an optionally substituted alkyl group;

ring A is a benzene ring optionally having additional one to three substituents;

p is an integer of 1 to 8;

$R^2$ is a hydrogen atom, an optionally substituted hydrocarbon group or an optionally substituted heterocyclic group;

q is an integer of 0 to 6;

m is 0 or 1;
R³ is a hydroxy group,
OR⁸ or NR⁹R¹⁰
  wherein R⁸ is an optionally substituted hydrocarbon group and wherein
  R⁹ and R¹⁰ are the same or different groups which are selected from a hydrogen atom, an optionally substituted hydrocarbon group, an optionally substituted heterocyclic group and an optionally substituted acyl group or R⁹ and R¹⁰ combine together to form a ring;
  R⁴ and R⁵ are the same or different groups which are selected from a hydrogen atom and an optionally substituted hydrocarbon group wherein R⁴ may form a ring with R²;
or a salt thereof;
  (2) one or more concomitant agents selected from the group consisting of a diabetes mellitus-treating agent, a diabetic complication-treating agent, an antihyperlipemic agent, a hypotensive agent, an anti-obesity agent, a diuretic, a chemotherapeutic agent and an immunotherapeutic agent; and
  (3) a pharmaceutically acceptable carrier.

3. The pharmaceutical composition according to claim 2 wherein the diabetes mellitus-treating agent is selected from the group consisting of an insulin formulation, an insulin sensitivity enhancing agent, an α-glucosidase inhibitor, a biguanide, a sulfonylurea, insulin secretion-promoting agent, amyrin agonist and phosphotyrosinphosphatase inhibitor.

4. The pharmaceutical composition according to claim 2 wherein the diabetic complication-treating agent is selected from the group consisting of an aldose reductase inhibitor, a neurotrophic factor, PKC inhibitor, AGE inhibitor, an active oxygen quenching agent and a cerebrovascular dilating agent.

5. The pharmaceutical composition according to claim 2 wherein the antihyperlipemic agent is selected from the group consisting of a statin-based compound, a squalene synthetase inhibitor and a fibrate compound.

6. The pharmaceutical composition according to claim 2 wherein the hypotensive agent is selected from the group consisting of an angiotensin converting enzyme inhibitor and an angiotensin II antagonist.

7. The pharmaceutical composition according to claim 2 wherein the anti-obesity agent is selected from the group consisting of central antiobesity agent, a pancreatic lipase inhibitor, β3 agonist, a peptide-based appetite-suppressing agent and a cholecystokinin agonist.

8. The pharmaceutical composition according to claim 2 wherein the diuretic is selected from the group consisting of a xanthine derivative, a thiazide formulation, antialdosterone formulation, a decarboxylase inhibitor, a chlorbenzenesulfonamide formulation, azosemide, isosorbide, ethacrynic acid, piretanide, bumetanide and furosemide.

9. The pharmaceutical composition according to claim 2 wherein the chemotherapeutic agent is selected from the group consisting of a alkylating agent, a metabolism antagonist, an anticancer antibiotic, a vegetable-derived anticancer agent, cisplatin, carboplatin and etoposide.

10. The pharmaceutical composition according to claim 2 wherein the immunotherapeutic agent is selected from the group consisting of a microorganism or bacterial component, a polysaccharide having immune potentiating activity, a cytokine obtained by a gene engineering technology and a colony stimulating factor.

11. A method for treating diabetes mellitus which comprises administering to a mammal in need thereof, (1) a pharmaceutically effective amount of the compound represented by the formula of

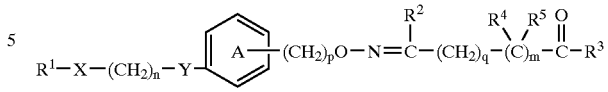

wherein R¹ is an optionally substituted thiazolyl, oxazolyl or oxadiazolyl group;
  X is a bond, —CO—, —CH(OH)— or a group represented by —NR⁶—
    wherein R⁶ is a hydrogen atom or an optionally substituted ailcyl group;
  n is an integer of 1 to 3;
  Y is an oxygen atom, a sulfur atom, —SO—, —SO₂— or a group represented by —NR⁷—
    wherein R⁷ is a hydrogen atom or an optionally substituted alkyl group;
  ring A is a benzene ring optionally having additional one to three substituents;
  p is an integer of 1 to 8;
  R² is a hydrogen atom, an optionally substituted hydrocarbon group or an optionally substituted heterocyclic group;
  q is an integer of 0 to 6;
  m is 0 or 1;
  R³ is a hydroxy group,
  OR⁸ or NR⁹R¹⁰
    wherein R⁸ is an optionally substituted hydrocarbon group and wherein
    R⁹ and R¹⁰ are the same or different groups which are selected from a hydrogen atom, an optionally substituted hydrocarbon group, an optionally substituted heterocyclic group and an optionally substituted acyl group or R⁹ and R¹⁰ combine together to form a ring;
    R⁴ and R⁵ are the same or different groups which are selected from a hydrogen atom and an optionally substituted hydrocarbon group wherein R⁴ may form a ring with R²;
or a salt thereof; in combination with
  (2) one or more concomitant agents selected from the group consisting of a diabetes mellitus-treating agent, a diabetic complication-treating agent, an antihyperlipemic agent, a hypotensive agent, an anti-obesity agent, a diuretic, a chemotherapeutic agent and an immunotherapeutic agent.

12. The method according to claim 11 wherein the diabetes mellitus-treating agent is selected from the group consisting of an insulin formulation, an insulin sensitivity enhancing agent, an α-glucosidase inhibitor, a Biguanide, a sulfonylurea, insulin secretion-promoting agent, amyrin agonist and phosphotyrosinphosphatase inhibitor.

13. The method according to claim 11 wherein the diabetic complication-treating agent is selected from the group consisting of an aldose reductase inhibitor, a neurotrophic factor, PKC inhibitor, AGE inhibitor, an active oxygen quenching agent and a cerebrovascular dilating agent.

14. The method according to claim 11 wherein the antihyperlipemic agent is selected from the group consisting of a statin-based compound, a squalene synthetase inhibitor and a fibrate compound.

15. The method according to claim 11 wherein the hypotensive agent is selected from the group consisting of an angiotensin converting enzyme inhibitor and an angiotensin II antagonist.

16. The method according to claim 11 wherein the anti-obesity agent is selected from the group consisting of central antiobesity agent, a pancreatic lipase inhibitor, β3 agonist, a peptide-based appetite-suppressing agent and a cholecystokinin agonist.

17. The method according to claim 11 wherein the diuretic is selected from the group consisting of a xanthine derivative, a thiazide formulation, antialdosterone formulation, a decarboxylase inhibitor, a chlorbenzenesulfonamide formulation, azosemide, isosorbide, ethacrynic acid, piretanide, bumetanide and furosemide.

18. The method according to claim 11 wherein the chemotherapeutic agent is selected from the group consisting of a alkylating agent, a metabolism antagonist, an anticancer antibiotic, a vegetable-derived anticancer agent, cisplatin, carboplatin and etoposide.

19. The method according to claim 11 wherein the immunotherapeutic agent is selected from the group consisting of a microorganism or bacterial component, a polysaccharide having immune potentiating activity, a cytokine obtained by a gene engineering technology and a colony stimulating factor.

* * * * *

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
gtgggtaccg aaatgaccat ggttgacaca gag                                   33

<210> SEQ ID NO 2
<211> LENGTH: 33
<212> TYPE: DNA
<213> ORGANISM: Artificial
<220> FEATURE:
<223> OTHER INFORMATION: primer

<400> SEQUENCE: 2
ggggtcgacc aggactctct gctagtacaa gtc                                   33

<210> SEQ ID NO 3
<211> LENGTH: 33
<212> TYPE: DNA
<213> ORGANISM: Artificial
<220> FEATURE:
<223> OTHER INFORMATION: primer for pcr

<400> SEQUENCE: 3
ttagaattcg acatggacac caaacatttc ctg                                   33

<210> SEQ ID NO 4
<211> LENGTH: 33
<212> TYPE: DNA
<213> ORGANISM: Artificial
<220> FEATURE:
<223> OTHER INFORMATION: primer for pcr

<400> SEQUENCE: 4
cccctcgagc taagtcattt ggtgcggcgc ctc                                   33

<210> SEQ ID NO 5
<211> LENGTH: 36
<212> TYPE: DNA
<213> ORGANISM: Artificial
<220> FEATURE:
<223> OTHER INFORMATION: primer for pcr

<400> SEQUENCE: 5
tcgacagggg accaggacaa aggtcacgtt cgggag                                36
```

```
<210> SEQ ID NO 6
<211> LENGTH: 36
<212> TYPE: DNA
<213> ORGANISM: Artificial
<220> FEATURE:
<223> OTHER INFORMATION: primer for pcr

<400> SEQUENCE: 6
tcgactcccg aacgtgacct ttgtcctggt cccctg                               36

<210> SEQ ID NO 7
<211> LENGTH: 28
<212> TYPE: DNA
<213> ORGANISM: Artificial
<220> FEATURE:
<223> OTHER INFORMATION: primer for pcr

<400> SEQUENCE: 7
cccagatctc cccagcgtct tgtcattg                                        28

<210> SEQ ID NO 8
<211> LENGTH: 28
<212> TYPE: DNA
<213> ORGANISM: Artificial
<220> FEATURE:
<223> OTHER INFORMATION: primer for pcr

<400> SEQUENCE: 8
tcaccatggt caagctttta agcgggtc                                        28
```